(12) United States Patent
Hamprecht et al.

(10) Patent No.: US 8,633,182 B2
(45) Date of Patent: Jan. 21, 2014

(54) INDANYLOXYPHENYLCYCLOPROPANE-CARBOXYLIC ACIDS

(71) Applicants: Dieter Hamprecht, Pozzolengo (IT); Sara Frattini, Castelleone (IT); Iain Lingard, Monza (IT); Stefan Peters, Biberach an der Riss (DE)

(72) Inventors: Dieter Hamprecht, Pozzolengo (IT); Sara Frattini, Castelleone (IT); Iain Lingard, Monza (IT); Stefan Peters, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/900,121

(22) Filed: May 22, 2013

(65) Prior Publication Data

US 2013/0324514 A1    Dec. 5, 2013

(30) Foreign Application Priority Data

May 30, 2012    (EP) .................................... 12170057

(51) Int. Cl.

| | | |
|---|---|---|
| A61K 31/397 | (2006.01) |
| C07D 213/02 | (2006.01) |
| A61K 31/44 | (2006.01) |
| C07D 215/00 | (2006.01) |
| A61K 31/47 | (2006.01) |
| C07D 217/00 | (2006.01) |
| C07D 249/08 | (2006.01) |
| A61K 31/4196 | (2006.01) |
| C07D 271/06 | (2006.01) |
| A61K 31/4245 | (2006.01) |
| C07D 263/30 | (2006.01) |
| A61K 31/421 | (2006.01) |
| C07D 231/56 | (2006.01) |
| A61K 31/416 | (2006.01) |
| C07D 209/04 | (2006.01) |
| A61K 31/4164 | (2006.01) |
| C07D 231/54 | (2006.01) |
| C07D 231/10 | (2006.01) |
| A61K 31/415 | (2006.01) |
| C07D 257/04 | (2006.01) |
| A61K 31/41 | (2006.01) |
| C07D 275/02 | (2006.01) |
| A61K 31/425 | (2006.01) |
| C07D 335/02 | (2006.01) |
| A61K 31/382 | (2006.01) |
| C07D 311/00 | (2006.01) |
| A61K 31/341 | (2006.01) |
| C07D 315/00 | (2006.01) |
| A61K 31/351 | (2006.01) |
| A61K 31/40 | (2006.01) |
| C07D 333/02 | (2006.01) |
| A61K 31/381 | (2006.01) |

(52) U.S. Cl.
USPC ...... 514/210.01; 546/147; 546/170; 546/342; 548/131; 548/214; 548/236; 548/253; 548/268.8; 548/341.5; 548/362.5; 548/376.1; 548/510; 548/572; 548/950; 549/28; 549/79; 549/427; 549/499; 514/277; 514/307; 514/311; 514/364; 514/372; 514/374; 514/381; 514/383; 514/385; 514/406; 514/415; 514/432; 514/438; 514/451; 514/461

(58) Field of Classification Search
USPC ............ 514/210.01, 277, 307, 311, 364, 372, 514/374, 381, 383, 385, 406, 415, 432, 438, 514/451, 461; 546/147, 170, 342; 548/131, 548/214, 236, 253, 268.8, 341.5, 362.5, 548/376.1, 510, 572, 950; 549/28, 79, 427, 549/499

See application file for complete search history.

(56) References Cited

U.S. PATENT DOCUMENTS 8,389,580 B2 *    3/2013    McCafferty et al. .......... 514/647

* cited by examiner

*Primary Examiner* — Samantha Shterengarts
(74) *Attorney, Agent, or Firm* — Michael P. Morris; Timothy X. Witkowski

(57) ABSTRACT

The present invention relates to compounds of general formula I,

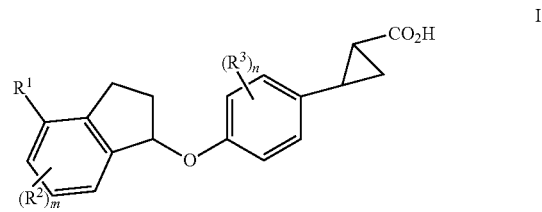

wherein the groups $R^1$, $R^2$, $R^3$, m and n are defined as in claim 1, which have valuable pharmacological properties, in particular bind to the GPR40 receptor and modulate its activity. The compounds are suitable for treatment and prevention of diseases which can be influenced by this receptor, such as metabolic diseases, in particular diabetes type 2. Furthermore, the invention relates to novel intermediates, useful for the synthesis of compounds of formula I.

17 Claims, No Drawings

INDANYLOXYPHENYLCYCLOPROPANE-CARBOXYLIC ACIDS

This application claims priority to European Patent Application No. 12170057.9, filed May 30, 2012, the contents of which are hereby incorporated by reference in its entirety.

FIELD OF THE INVENTION

The present invention relates to novel indanyloxyphenylcyclopropanecarboxylic acids, that are agonists of the G-protein coupled receptor 40 (GPR40, also known as free fatty acid receptor FFAR 1), to processes for their preparation, to pharmaceutical compositions containing these compounds and to their medical use for the prophylaxis and/or treatment of diseases which can be influenced by the modulation of the function of GPR40. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

The free fatty acid receptor GPR40 (also referred to as either FFAR, FFAR1, or FFA1) is a cell-surface receptor and a member of the gene superfamily of G-protein coupled receptors, which was first identified as a so-called orphan receptor, i.e. a receptor without a known ligand, based on the predicted prescence of seven putative transmembrane regions in the corresponding protein (Sawzdargo et al. (1997) Biochem. Biophys. Res. Commun. 239: 543-547). GPR40 is found to be highly expressed in several particular cell types: the pancreatic β cells and insulin-secreting cell lines, as well as in enteroendocrine cells, taste cells, and is reported to be expressed in immune cells, splenocytes, and in the human and monkey brain. Meanwhile, fatty acids of varying chain lengths are thought to represent the endogenous ligands for GPR40, activation of which is linked primarily to the modulation of the Gq family of intra-cellular signaling G proteins and concomitant induction of elevated calcium levels, although activation of Gs- and Gi-proteins to modulate intracellular levels of cAMP have also been reported. GPR40 is activated especially by long-chain FFA, particularly oleate, as well as the PPAR-gamma agonist rosiglitazone.

It has been recognized that the fatty acids that serve as activators for GPR40 augment the elevated plasma glucose-induced secretion of insulin through GPR40 receptors that are expressed in the insulin secreting cells (Itoh et al. (2003) Nature 422: 173-176; Briscoe et al. (2003) J. Biol. Chem. 278: 11303-11311; Kotarsky et al. (2003) Biochem. Biophys. Res. Commun. 301: 406-410). Despite initial controversy, the use of GPR40 agonist appears to be the appropriate for increasing insulin release for the treatment of diabetes (see e.g. Diabetes 2008, 57, 2211; J. Med. Chem. 2007, 50, 2807). Typically, long term diabetes therapy leads to the gradual diminution of islet activity, so that after extended periods of treatment Type 2 diabetic patients need treatment with daily insulin injections instead. GPR40 agonists may have the potential to restore or preserve islet function, therefore, GPR40 agonists may be beneficial also in that that they may delay or prevent the diminution and loss of islet function in a Type 2 diabetic patient.

It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Further studies indicating that the GPR40 modulatory role on the release of incretins from the enteroendocrine cells, including CCK, GLP-1, GIP, PYY, and possibly others, suggest that GPR40 modulators may contribute to enhanced insulin release from the pancreatic beta cells also indirectly by e.g. a synergistic effect of GLP-1 and possibly GIP on the insulin release, and the other release incretins may also contribute to an overall beneficial contribution of GPR40 modulation on metabolic diseases. The indirect contributions of GPR40 modulation on insulin release through the elevation of plasma levels of incretins may be further augmented by the coadministration of inhibitors of the enzymes responsible for the incretin degradation, such as inhibitors of DPP-4.

Insulin imbalances lead to conditions such as type II diabetes mellitus, a serious metabolic disease. The modulation of the function of GPR40 in modulating insulin secretion indicates the therapeutic agents capable of modulating GPR40 function could be useful for the treatment of disorders such as diabetes and conditions associated with the disease, including insulin resistance, obesity, cardiovascular disease and dyslipidemia.

OBJECT OF THE PRESENT INVENTION

The object of the present invention is to provide new compounds, hereinafter described as compounds of formula I, in particular new indanyloxyphenylcyclopropanecarboxylic acids, which are active with regard to the G-protein-coupled receptor GPR40, notably are agonists of the G-protein-coupled receptor GPR40.

A further object of the present invention is to provide new compounds, in particular new indanyloxyphenylcyclopropanecarboxylic acids, which have an activating effect on the G-protein-coupled receptor GPR40 in vitro and/or in vivo and possess suitable pharmacological and pharmacokinetic properties to use them as medicaments.

A further object of the present invention is to provide effective GPR40 agonists, in particular for the treatment of metabolic disorders, for example diabetes, dyslipidemia and/or obesity.

A further object of the present invention is to provide methods for treating a disease or condition mediated by the activation the G-protein-coupled receptor GPR40 in a patient.

A further object of the present invention is to provide a pharmaceutical composition comprising at least one compound according to the invention.

A further object of the present invention is to provide a combination of at least one compound according to the invention with one or more additional therapeutic agents.

A further object of the present invention is to provide novel homochiral intermediates, identified as intermediates XIVa, XIVb, and XVa, XVb in scheme 7 hereinafter, useful for the synthesis of compounds of formula I.

A further object of the present invention is to provide a enantioselective synthesis of the novel homochiral intermediates useful for the synthesis of compounds of formula I.

Further objects of the present invention become apparent to the one skilled in the art by the description hereinbefore and in the following and by the examples.

GPR40 modulators are known in the art, for example, the compounds disclosed in WO 2004041266 (EP 1559422), WO 2007033002 and WO 2009157418. The indanyloxyphenyl-cyclopropanecarboxylic acids of the present invention may provide several advantages, such as enhanced potency, high metabolic and/or chemical stability, high selectivity and tolerability, enhanced solubility, and the possibility to form stable salts.

Regarding the novel homochiral intermediates according to the invention it should be noted that synthesis of racemic

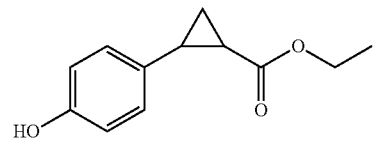

is described in WO2011/103189, however this synthesis would not be useful for the direct preparation of chiral analogue intermediates due to the use of methoxy as protecting group. The use of the tert-butyl protecting group in this synthesis is not described and therefore compounds of structure:

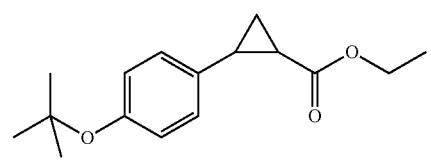 [SMILES: CCOC(=O)C1CC1c1ccc(OC(C)(C)C)cc1]

and close homologues (e.g. Intermediate 4a and Intermediate 5a, described in the experimental part) are novel.

SUMMARY OF THE INVENTION

In a first aspect the invention relates to a compound of formula

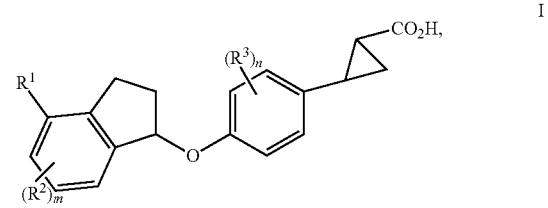

wherein
$R^1$ is selected from the group $R^1$-G1 consisting of a phenyl ring, a tetrazolyl ring,
a 5-membered heteroaromatic ring containing 1 —NH—, —O— or —S— group,
a 5-membered heteroaromatic ring containing 1 —NH—, —O— or —S— group and additionally 1 or 2 =N— atoms,
a 6-membered heteroaromatic ring containing 1, 2 or 3 =N— atoms,
wherein optionally a second ring is annulated to said phenyl ring or to said 5- or 6-membered heteroaromatic rings and said second ring is 5- or 6-membered, unsaturated or aromatic and may contain 1, 2, or 3 heteroatoms independently of each other selected from =N—, —NH—, —O— and —S— with the proviso that only up to two of the heteroatoms are O and S and no O—O, S—S, and S—O bond is formed, and wherein in said second ring independently of the presence of heteroatoms 1 or 2 $CH_2$ groups may be replaced by —C(O)—, —S(O)— or —S(O)$_2$—, and
wherein said phenyl ring, tetrazolyl ring, 5- or 6-membered heteroaromatic ring, annulated phenyl ring, and annulated 5- or 6-membered heteroaromatic ring are optionally substituted at a carbon atom with one group $R^{1a}$; and wherein said phenyl ring, tetrazolyl ring, 5- or 6-membered heteroaromatic ring, annulated phenyl ring, and annulated 5- or 6-membered heteroaromatic ring are optionally additionally substituted at carbon atoms with 1 to 3 groups independently selected from $R^{1b}$; and wherein the H-atom in one or more NH groups present in said tetrazolyl ring, 5- or 6-membered heteroaromatic ring, annulated phenyl ring, or annulated 5- or 6-membered heteroaromatic ring optionally is replaced by $R^M$, H, F, Cl, Br, I, NC—, $C_{1-8}$-alkyl, $C_{2-6}$-alkenyl, $C_{2-6}$-alkynyl, $C_{3-8}$-cycloalkyl, $C_{3-8}$-cycloalkyl-$C_{5-12}$-bicycloalkyl-, $C_{5-12}$-bicycloalkyl-$C_{1-6}$-alkyl-, $C_{5-6}$-cycloalkenyl, $C_{5-6}$-cycloalkenyl-$C_{1-4}$-alkyl, $C_{1-8}$-alkyloxy, $C_{3-6}$-cycloalkyl-oxy, $C_{3-6}$-cycloalkyl-$C_{1-4}$-alkyloxy, $C_{1-4}$-alkyl-C(O)—, —NHR$^N$, HNR$^M$—C(O)—, $C_{1-4}$-alkyl-NR$^M$—C(O)—, wherein any of the saturated and unsaturated aliphatic and carbocyclic groups and submoieties within the groups mentioned optionally and independently are substituted with one or more F atoms and/or 1 to 3 $R^{1c}$ groups, $R^2$ is selected from the group $R^2$-G1 consisting of F, Cl, Br, I, $C_{1-4}$-alkyl, $C_{3-6}$-cycloalkyl, NC—, $H_2N$—C(O)—, $C_{1-4}$-alkyl-NR$^M$—C(O)—, HO—C(O)—, $C_{1-4}$-alkyl-O—C(O)—, $C_{1-4}$-alkyloxy, and $C_{1-4}$-alkyl-S(O)$_2$—, wherein any alkyl and cycloalkyl group or sub-group within the groups mentioned is optionally substituted with one or more F atoms, and wherein multiple $R^2$ may be identical or different, if m is 2 or 3;

$R^3$ is selected from the group $R^3$-G1 consisting of F, Cl, Br, I, NC—, $C_{1-6}$-alkyl, $C_{2-6}$-alkenyl, $C_{2-6}$-alkinyl, $C_{3-6}$-cycloalkyl-, $C_{1-4}$-alkyl-NH—, ($C_{1-4}$-alkyl)$_2$N—, $C_{1-6}$-alkyl-O—, $C_{3-6}$-cycloalkyl-O—, $C_{1-4}$-alkyl-S—, $C_{1-4}$-alkyl-S(O)—, and $C_{1-4}$-alkyl-S(O)$_2$, wherein each alkyl and cycloalkyl group and each alkyl and cycloalkyl sub-group within the groups mentioned is optionally substituted with 1 or more F atoms;

m is an integer selected from 0, 1, 2, and 3;

n is an integer selected from 0, 1, 2, and 3;

$R^{1a}$ is selected from the group $R^{1a}$-G1 consisting of $C_{1-6}$-alkyl, $C_{2-6}$-alkenyl, $C_{2-6}$-alkinyl, $C_{3-6}$-cycloalkyl-, $C_{3-6}$-cycloalkyl-$C_{1-6}$-alkyl, $C_{1-4}$-alkyl-NH—, ($C_{1-4}$-alkyl)$_2$N—, —NHR$^N$, HNR$^M$—C(O)—, $C_{1-4}$-alkyl-NR$^M$—C(O)—, $C_{1-6}$-alkyl-O—, $C_{3-6}$-cycloalkyl-O—, $C_{3-6}$-cycloalkyl-$C_{1-6}$-alkyl-O—, $C_{1-4}$-alkyl-S—, $C_{1-4}$-alkyl-S(O)—, and $C_{1-4}$-alkyl-S(O)$_2$, wherein a —CH$_2$— member within a $C_{4-6}$-cycloalkyl-group or sub-group within the groups mentioned optionally is replaced by —NR$^N$—, —O—, —S—, —S(O)— or —S(O$_2$)—, or wherein a >CH—CH$_2$— member or a —CH$_2$—CH$_2$— member within a $C_{5-6}$-cycloalkyl-group or sub-group within the groups mentioned optionally is replaced by >N—C(O)—, >N—S(O)—, >N—S(O)$_2$—, —N(R$^M$)—C(O)—, —N(R$^M$)—S(O)— or —N(R$^M$)—S(O)$_2$—, and wherein each alkyl and cycloalkyl group and each alkyl and cycloalkyl sub-group within the groups mentioned optionally is substituted with HO—, HO—C1-4-alkyl-, C1-4-alkyl-oxy, $C_{1-4}$-alkyl-oxy-$C_{1-4}$-alkyl-, $C_{1-4}$-alkyl-sulfanyl, $C_{1-4}$-alkyl-sulfinyl, $C_{1-4}$-alkyl-sulfonyl, $H_2N$—C(O)—, $C_{1-4}$-alkyl-NH—C(O)—, ($C_{1-4}$-alkyl)$_2$N—C(O)— or $C_{3-6}$-cycloalkyl-NR$^M$—C(O)— and/or optionally substituted with 1 or more F atoms;

a phenyl ring, a tetrazolyl ring, a 5-membered heteroaromatic ring containing 1 —NH—, —O— or —S— group, a 5-membered heteroaromatic ring containing 1 —NH—, —O— or —S— group and additionally 1 or 2 =N— atoms, a 6-membered heteroaromatic ring containing 1, 2 or 3 =N— atoms, wherein said rings are optionally substituted with one or more groups selected from $R^{1b}$; and wherein the H-atom in one or more NH groups present in said tetrazolyl ring or 5-membered heteroaromatic ring is replaced by $R^M$, $R^{1b}$ is selected from the group $R^{1b}$-G1 consisting of F, Cl, Br, I, CN, —OH, $C_{1-4}$-alkyl, $C_{3-6}$-cycloalkyl-, HO—$C_{1-4}$-alkyl, $C_{1-4}$-alkyl-O—$C_{1-4}$-alkyl, —NR$^N$H, $C_{1-4}$-alkyl-NR$^N$—, $C_{1-4}$-alkyl-O—, $C_{3-6}$-cycloalkyl-O—, $C_{1-4}$-alkyl-O—$C_{1-4}$-alkyl-O—, $C_{1-4}$-alkyl-S—, $C_{1-4}$-alkyl-S(O)—, and $C_{1-4}$-alkyl-S(O)$_2$—, wherein any alkyl and cycloalkyl group or sub-group within the groups mentioned is optionally substituted with 1 or more F atoms;

$R^{1c}$ is selected from the group $R^{1c}$-G1 consisting of F, Cl, Br, I, CN, —OH, $C_{1-3}$-alkyl, HO—$C_{1-3}$-alkyl, $C_{1-4}$-alkyl-O— and $C_{1-3}$-alkyl-O—$C_{1-3}$-alkyl, wherein any alkyl group or sub-group within the groups mentioned is optionally substituted with 1 or more F atoms; and $R^N$ is independently of each other selected from the group $R^N$-G1 consisting of H, $C_{1-4}$-alkyl, HO—$C_{2-4}$-alkyl (with the proviso that at least 2 carbon atoms are between the HO-group and an NH), $C_{1-4}$-alkyl-O—$C_{2-4}$-alkyl- (with the proviso that at least 2 carbon atoms are between an O-group and an NH), $C_{1-4}$-alkyl-C(O)—, $C_{1-4}$-alkyl-O—C(O)— and $C_{1-4}$-alkyl-S(O)$_2$—;

wherein any alkyl group or sub-group within the groups mentioned is optionally substituted with 1 or more F atoms;

$R^M$ is independently of each other selected from the group $R^M$-G1 consisting of H, $C_{1-4}$-alkyl, HO—$C_{2-4}$-alkyl (with the proviso that at least 2 carbon atoms are between the HO-group and an NH), and $C_{1-4}$-alkyl-O—$C_{2-4}$-alkyl- (with the proviso that at least 2 carbon atoms are between an O-group and an NH);

wherein any alkyl group or sub-group within the groups mentioned is optionally substituted with 1 or more F atoms;

wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, $R^1$-G1 defines genus 1 of the substituent $R^1$.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR40 in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR40 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the G-protein-coupled receptor GPR40.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

In a further aspect this invention relates to novel homochiral intermediates, identified as intermediates XIVa, XIVb, and XVa, XVb in scheme 7 hereinafter, useful for the synthesis of compounds of formula I.

In a further aspect this invention relates to an enantioselective synthesis of novel homochiral intermediates useful for the synthesis of compounds of formula I.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, $R^3$, m and n are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:
$R^1$-G1:
The group $R^1$ is preferably selected from the group $R^1$-G1 as defined hereinbefore.

$R^1$-G2:
According to one embodiment the group $R^1$ is selected from the group $R^1$-G2 consisting of a phenyl ring, a tetrazolyl ring, a 5-membered heteroaromatic ring containing 1 —NH— or —O-group, a 5-membered heteroaromatic ring containing 1 —NH— or —O— group and additionally 1 or 2 =N— atoms, a 6-membered heteroaromatic ring containing 1, 2 or 3 =N— atoms, wherein said phenyl ring, tetrazolyl ring and 5- or 6-membered heteroaromatic ring are substituted at a carbon atom with one group $R^{1a}$; and wherein said phenyl ring, tetrazolyl ring, 5- or 6-membered heteroaromatic ring are optionally additionally substituted at carbon atoms with 1 to 3 groups independently selected from $R^{1b}$; and wherein the H-atom in one or more NH groups present in said tetrazolyl ring, 5- or 6-membered heteroaromatic ring optionally is replaced by $R^M$, H, F, Cl, Br, J, NC—, $C_{1-6}$-alkyl, $C_{2-4}$-alkenyl, $C_{2-4}$-alkynyl, $C_{3-6}$-cycloalkyl, $C_{3-6}$-cycloalkyl-$C_{1-3}$-alkyl, $C_{5-10}$-bicycloalkyl-, $C_{5-10}$-bicycloalkyl-$C_{1-4}$-alkyl-, $C_{1-4}$-alkyloxy, $C_{3-6}$-cycloalkyl-oxy, $C_{3-6}$-cycloalkyl-$C_{1-3}$-alkyloxy, $C_{1-3}$-alkyl-C(O)—, —NHR$^N$, HNR$^M$—C(O)—, $C_{1-4}$-alkyl-NR$^M$—C(O)—, wherein any of the saturated and unsaturated aliphatic and carbocyclic groups and submoieties within the groups mentioned optionally and independently are substituted with 1 to 3 fluorine atoms and/or 1 $R^{1c}$ group.

$R^1$-G3:
According to one embodiment the group $R^1$ is selected from the group $R^1$-G3 consisting of

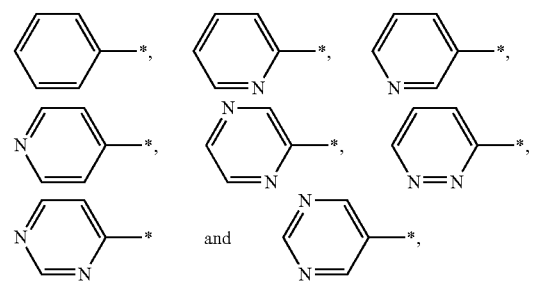

wherein any of the phenyl ring and the 6-membered heteroaromatic rings specified above are substituted at a carbon atom with one group $R^{1a}$; and are optionally additionally substituted at carbon atoms with 1 or 2 groups independently selected from $R^{1b}$;

H, F, Cl, Br, NC—, $C_{1-3}$-alkyl, $C_{1-3}$-alkyloxy, $C_{1-3}$-alkyl-C(O)—, —NHR$^N$, HNR$^M$—C(O)— and $C_{1-4}$-alkyl-NR$^M$—C(O)—, wherein any of the aliphatic groups and submoieties within the groups mentioned optionally and independently are substituted with 1 to 3 fluorine atoms and/or 1 $R^{1c}$ group.

$R^1$-G4:
In another embodiment the group $R^1$ is selected from the group $R^1$-G4 consisting of

wherein the phenyl and pyridyl ring are substituted at a carbon atom with one group $R^{1a}$; and are optionally additionally substituted at carbon atoms with 1 or 2 groups independently selected from $R^{1b}$;

H, F, Cl, Br, $C_{1-3}$-alkyl, $C_{1-3}$-alkyloxy, $HNR^M$—C(O)— and $C_{1-4}$-alkyl-$NR^M$—C(O)—, wherein any of the aliphatic groups or submoieties optionally and independently are substituted with 1 to 3 fluorine atoms and/or 1 $R^{1c}$ group.

$R^1$-G4a:

In another embodiment the group $R^1$ is selected from the group $R^1$-G4a consisting of

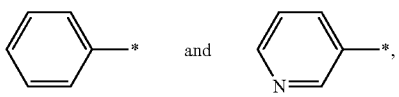

wherein the phenyl and pyridyl ring are substituted at a carbon atom with one group $R^{1a}$; and are optionally additionally substituted at carbon atoms with 1 or 2 groups independently selected from R.

$R^1$-G4b:

In another embodiment the group $R^1$ is selected from the group $R^1$-G4b consisting of H, F, Cl, Br, $C_{1-3}$-alkyl, $C_{1-3}$-alkyloxy, $HNR^M$—C(O)— and $C_{1-4}$-alkyl-$NR^M$—C(O)—, $R^1$-G5:

In another embodiment the group $R^1$ is selected from the group $R^1$-G5 consisting of

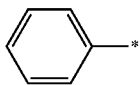

wherein the phenyl ring is substituted with one group $R^{1a}$; and is optionally additionally substituted at with 1 or 2 groups independently selected from $R^{1b}$, preferably

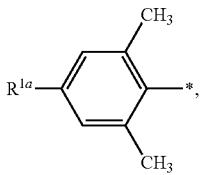

and H, F, Cl, Br, $H_3C$—, $F_3C$—, $H_3C$—O—, $F_3C$—O— and HO—$C_{1-4}$-alkyl-HN—C(O)—.

$R^2$:

$R^2$-G1:

The group $R^2$ is preferably selected from the group $R^2$-G1 as defined hereinbefore.

$R^2$-G2:

In another embodiment the group $R^2$ is selected from the group $R^2$-G2 consisting of F, Cl, Br, I, $C_{1-3}$-alkyl, $C_{3-6}$-cycloalkyl, NC—, $H_2N$—C(O)—, $C_{1-3}$-alkyl-$NR^M$—C(O)—, HO—C(O)—, $C_{1-3}$-alkyl-O—C(O)— and $C_{1-3}$-alkyloxy, wherein any alkyl and cycloalkyl group or sub-group within the groups mentioned is optionally substituted with 1 to 3 F atoms, and wherein multiple $R^2$ may be identical or different, if m is 2 or 3.

$R^2$-G3:

In another embodiment the group $R^2$ is selected from the group $R^2$-G3 consisting of F, Cl, Br, $C_{1-3}$-alkyl, NC— and $C_{1-3}$-alkyloxy, wherein any alkyl or sub-group is optionally substituted with 1 to 3 F atoms, and wherein multiple $R^2$ may be identical or different, if m is 2 or 3.

$R^3$:

$R^3$-G1:

The group $R^3$ is preferably selected from the group $R^3$-G1 as defined hereinbefore.

$R^3$-G2:

In another embodiment the group $R^3$ is selected from the group $R^3$-G2 consisting of F, Cl, Br, NC—, $C_{1-4}$-alkyl, $C_{2-4}$-alkenyl, $C_{2-4}$-alkinyl, $C_{3-6}$-cycloalkyl-, $C_{1-3}$-alkyl-NH—, $(C_{1-3}$-alkyl$)_2$N—, $C_{1-4}$-alkyl-O—, $C_{3-6}$-cycloalkyl-O— and $C_{1-3}$-alkyl-S(O)$_2$, wherein each alkyl and cycloalkyl group and each alkyl and cycloalkyl sub-group within the groups mentioned is optionally substituted with 1 to 3 F atoms.

$R^3$-G3:

In another embodiment the group $R^3$ is selected from the group $R^3$-G3 consisting of F, Cl, Br, NC—, $C_{1-3}$-alkyl, $C_{1-3}$-alkyl-O— and $C_{3-6}$-cycloalkyl-O—, wherein each alkyl and cycloalkyl group and each alkyl and cycloalkyl sub-group within the groups mentioned is optionally substituted with 1 to 3 F atoms.

$R^3$-G4:

In another embodiment the group $R^3$ is selected from the group $R^3$-G4 consisting of F, Cl, Br, $H_3C$—, $F_3C$—, $H_3C$—O— and $F_3C$—O—.

$R^3$-G5:

In another embodiment the group $R^3$ is selected from the group $R^3$-G5 consisting of F, Cl, Br, $H_3C$— and $H_3C$—O—.

m denotes preferably 0, 1 or 2, particularly preferred is 0 or 1.

n denotes preferably 0, 1 or 2, particularly preferred is 0 or 1.

$R^{1a}$-G1:

The group $R^{1a}$ is preferably selected from the group $R^{1a}$-G1 as defined hereinbefore.

$R^{1a}$-G2a:

According to one embodiment the group $R^{1a}$ is selected from the group $R^{1a}$-G2a consisting of $C_{1-4}$-alkyl, $C_{2-4}$-alkenyl, $C_{2-4}$-alkinyl, $C_{3-6}$-cycloalkyl-, $C_{3-6}$-cycloalkyl-$C_{1-4}$-alkyl, $C_{1-4}$-alkyl-NH—, $(C_{1-4}$-alkyl$)_2$N—, —$NHR^N$, $HNR^M$—C(O)—, $C_{1-4}$-alkyl-$NR^M$—C(O)—, $C_{1-6}$-alkyl-O—, $C_{3-6}$-cycloalkyl-O—, $C_{3-6}$-cycloalkyl-$C_{1-4}$-alkyl-O— and $C_{1-4}$-alkyl-S(O)$_2$, wherein a —$CH_2$— member within a $C_{4-6}$-cycloalkyl-group or sub-group within the groups mentioned optionally is replaced by —$NR^N$—, —O— or —S(O$_2$)—, or wherein a >CH—$CH_2$— member or a —$CH_2$—$CH_2$— member within a $C_{5-6}$-cycloalkyl-group or sub-group within the groups mentioned optionally is replaced by >N—C(O)—, >N—S(O)$_2$—, —N($R^M$)—C(O)— or —N($R^M$)—S(O)$_2$—, and wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyloxy-$C_{1-4}$-alkyl-, $C_{1-4}$-alkyl-sulfonyl, $H_2N$—C(O)—, $C_{1-4}$-alkyl-NH—C(O)— or $(C_{1-4}$-alkyl)$_2$N—C(O)— and/or optionally substituted with 1 to 3 F atoms.

$R^{1a}$-G2b:

According to one embodiment the group $R^{1a}$ is selected from the group $R^{1a}$-G2b consisting of
a phenyl ring, a tetrazolyl ring,
a 5-membered heteroaromatic ring containing 1 —NH— or —O— group,
a 5-membered heteroaromatic ring containing 1 —NH— or —O— group and additionally 1 or 2 =N— atoms,
a 6-membered heteroaromatic ring containing 1 or 2 =N— atoms,
   wherein said rings are optionally substituted with one to three groups selected from $R^{1b}$, and
   wherein the H-atom in one or more NH groups present in said tetrazolyl ring or 5-membered heteroaromatic ring is replaced by $R^M$.

$R^{1a}$-G3a:

According to one embodiment the group $R^{1a}$ is selected from the group $R^{1a}$-G3a consisting of
$C_{1-4}$-alkyl, $C_{3-6}$-cycloalkyl-$C_{1-4}$-alkyl, HNR$^M$—C(O)—, $C_{1-4}$-alkyl-NR$^M$—C(O)—, $C_{1-6}$-alkyl-O—, $C_{3-6}$-cycloalkyl-O— and $C_{3-6}$-cycloalkyl-$C_{1-3}$-alkyl-O—,
   wherein a —CH$_2$— member within a $C_{4-6}$-cycloalkyl- group or sub-group within the groups mentioned optionally is replaced by —NR$^N$—, —O— or —S(O)$_2$—, or
   wherein a >CH—CH$_2$— member or a —CH$_2$—CH$_2$— member within a $C_{5-6}$-cycloalkyl-group or sub-group within the groups mentioned optionally is replaced by >N—S(O)$_2$— or —N(R$^M$)—S(O)$_2$—, and
   wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyl-sulfonyl, $H_2N$—C(O)—, $C_{1-3}$-alkyl-NH—C(O)— or $(C_{1-3}$-alkyl)$_2$N—C(O)— and/or optionally substituted with 1 to 3 F atoms.

$R^{1a}$-G3b:

According to one embodiment the group $R^{1a}$ is selected from the group $R^{1a}$-G3b consisting of
a phenyl ring, a tetrazolyl ring,
a 5-membered heteroaromatic ring containing 1 —NH— or —O— group,
a 5-membered heteroaromatic ring containing 1 —NH— or —O— group and additionally 1 or 2 =N— atoms,
a 6-membered heteroaromatic ring containing 1 =N— atom,
   wherein said rings are optionally substituted with one or two groups selected from $R^{1b}$; and
   wherein the H-atom in one or more NH groups present in said tetrazolyl ring or 5-membered heteroaromatic ring is replaced by $R^M$.

$R^{1a}$-G4a:

According to one embodiment the group $R^{1a}$ is selected from the group $R^{1a}$-G4a consisting of
$C_{1-4}$-alkyl, $C_{3-6}$-cycloalkyl-, $C_{3-6}$-cycloalkyl-$C_{1-3}$-alkyl, HNR$^M$—C(O)—, $C_{1-3}$-alkyl-NR$^M$—C(O)—, $C_{1-5}$-alkyl-O—, $C_{3-6}$-cycloalkyl-O— and $C_{3-6}$-cycloalkyl-$C_{1-3}$-alkyl-O—,
   wherein a —CH$_2$— member within a $C_{4-6}$-cycloalkyl- group or sub-group within the groups mentioned optionally is replaced by —NR$^N$—, —O— or —S(O)$_2$—, or
   wherein a >CH—CH$_2$— member within a $C_{5-6}$-cycloalkyl- group or sub-group within the groups mentioned optionally is replaced by >N—S(O)$_2$— and
   wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyl-sulfonyl or $H_2N$—C(O)— and/or optionally substituted with 1 to 3 F atoms.

$R^{1a}$-G4b:

According to one embodiment the group $R^{1a}$ is selected from the group $R^{1a}$-G4b consisting of
a phenyl ring, a tetrazolyl ring,
a 5-membered heteroaromatic ring containing 1 —NH— or —O— group,
a 5-membered heteroaromatic ring containing 1 —NH— or —O— group and additionally 1 or 2 =N— atoms,
   wherein said rings are optionally substituted with one group selected from $R^{1b}$; and
   wherein the H-atom in one or more NH groups present in said tetrazolyl ring or 5-membered heteroaromatic ring is replaced by $R^M$.

$R^{1a}$-G5a:

According to one embodiment the group $R^{1a}$ is selected from the group $R^{1a}$-G5a consisting of
HNR$^M$—C(O)—, $C_{1-3}$-alkyl-NR$^M$—C(O)—, $C_{1-5}$-alkyl-O—, $C_{3-6}$-cycloalkyl-O— and $C_{3-6}$-cycloalkyl-$C_{1-3}$-alkyl-O—,
   wherein a —CH$_2$— member within a $C_{4-6}$-cycloalkyl- group or sub-group within the groups mentioned optionally is replaced by —NR$^N$—, —O— or —S(O)$_2$—, or
   wherein a >CH—CH$_2$— member within a $C_{5-6}$-cycloalkyl- group or sub-group within the groups mentioned optionally is replaced by >N—S(O)$_2$— and
   wherein each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyl-sulfonyl or $H_2N$—C(O)— and/or optionally substituted with 1 to 3 F atoms.

$R^{1a}$-G5b:

According to one embodiment the group $R^{1a}$ is selected from the group $R^{1a}$-G5b consisting of
a phenyl ring, a tetrazolyl ring,
a 5-membered heteroaromatic ring containing 1 —NH— or —O— group and additionally 1 or 2 =N— atoms,
   wherein said rings are optionally substituted with one group selected from $R^{1b}$; and
   wherein the H-atom in one or more NH groups present in said tetrazolyl ring or 5-membered heteroaromatic ring is replaced by $R^M$.

$R^{1b}$-G1:

The group $R^{1b}$ is preferably selected from the group $R^{1b}$-G1 as defined hereinbefore.

$R^{1b}$-G2:

According to one embodiment the group $R^{1b}$ is selected from the group $R^{1b}$-G2 consisting of F, Cl, Br, I, CN, —OH, $C_{1-3}$-alkyl, $C_{3-6}$-cycloalkyl-, HO—$C_{1-3}$-alkyl, $C_{1-3}$-alkyl-O— and $C_{3-6}$-cycloalkyl-O—,
   wherein any alkyl and cycloalkyl group or sub-group within the groups mentioned is optionally substituted with 1 to 3 F atoms.

$R^{1b}$-G3:

According to one embodiment the group $R^{1b}$ is selected from the group $R^{1b}$-G3 consisting of F, Cl, Br, CN, $C_{1-3}$-alkyl, $C_{3-6}$-cycloalkyl-, $C_{1-4}$-alkyl-O— and $C_{3-6}$-cycloalkyl-O—, wherein any alkyl and cycloalkyl group or sub-group within the groups mentioned is optionally substituted with 1 to 3 F atoms.

$R^{1b}$-G4:

According to one embodiment the group $R^{1b}$ is selected from the group $R^{1b}$-G4 consisting of F, Cl, Br and $C_{1-3}$-alkyl, wherein the $C_{1-3}$-alkyl group is optionally substituted with 1 to 3 F atoms.

$R^{1b}$-G5:

According to one embodiment the group $R^{1b}$ is selected from the group $R^{1b}$-G5 consisting $C_{1-3}$-alkyl, preferably $H_3C$—.

$R^{1c}$-G1:

The group $R^{1c}$ is preferably selected from the group $R^{1c}$-G1 as defined hereinbefore.

$R^{1c}$-G2:

According to one embodiment the group $R^{1c}$ is selected from the group $R^{1c}$-G2 consisting of F, Cl, Br, —OH, $C_{1-3}$-alkyl, HO—$C_{1-3}$-alkyl and $C_{1-4}$-alkyl-O—, wherein any alkyl group or sub-group within the groups mentioned is optionally substituted with 1 to 3 F atoms.

$R^{1c}$-G3:

According to one embodiment the group $R^{1c}$ is selected from the group $R^{1c}$-G3 consisting of F, $C_{1-3}$-alkyl and $C_{1-3}$-alkyl-O—, wherein any alkyl group or sub-group within the groups mentioned is optionally substituted with 1 to 3 F atoms.

$R^c$-G4:

According to one embodiment the group $R^{1c}$ is selected from the group $R^{1c}$-G4 consisting $C_{1-3}$-alkyl, preferably $H_3C$—.

$R^N$-G1:

The group $R^N$ is preferably selected from the group $R^N$-G1 as defined hereinbefore.

$R^N$-G2:

According to one embodiment the group $R^N$ is selected from the group $R^N$-G2 consisting of H, $C_{1-4}$-alkyl, HO—$C_{1-4}$-alkyl (with the proviso that at least 2 carbon atoms are between the HO-group and an NH), $C_{1-4}$-alkyl-C(O)—, $C_{1-3}$-alkyl-O—C(O)— and $C_{1-3}$-alkyl-S(O)$_2$—;

wherein any alkyl group or sub-group within the groups mentioned is optionally substituted with 1 to 3 F atoms.

$R^N$-G3:

According to one embodiment the group $R^N$ is selected from the group $R^N$-G3 consisting of H, $C_{1-4}$-alkyl, HO—$C_{2-4}$-alkyl (with the proviso that at least 2 carbon atoms are between the HO-group and an NH) and $C_{1-3}$-alkyl-S(O)$_2$—;

wherein any alkyl group or sub-group within the groups mentioned is optionally substituted with 1 to 3 F atoms.

$R^M$-G1:

The group $R^M$ is preferably selected from the group $R^M$-G1 as defined hereinbefore.

$R^M$-G2:

According to one embodiment the group $R^M$ is selected from the group $R^M$-G2 consisting of H, $C_{1-3}$-alkyl, HO—$C_{2-4}$-alkyl (with the proviso that at least 2 carbon atoms are between the HO-group and an NH), and $C_{1-3}$-alkyl-O—$C_{2-3}$-alkyl- (with the proviso that at least 2 carbon atoms are between an O-group and an NH);

wherein any alkyl group or sub-group within the groups mentioned is optionally substituted with 1 to 5 F atoms.

$R^M$-G3:

According to one embodiment the group $R^M$ is selected from the group $R^M$-G3 consisting of H, —$CH_3$, HO—$C_{2-4}$-alkyl (with the proviso that at least 2 carbon atoms are between the HO-group and an NH), and $H_3C$—O—$CH_2$—$CH_2$—;

wherein any alkyl group or sub-group within the groups mentioned is optionally substituted with 1 to 3 F atoms.

$R^M$-G4:

According to one embodiment the group $R^M$ is selected from the group $R^M$-G4 consisting of H, —$CH_3$, HO—$C_{2-4}$-alkyl (with the proviso that at least 2 carbon atoms are between the HO-group and an NH);

wherein any alkyl group or sub-group within the groups mentioned is optionally substituted with 1 to 3 F atoms.

Preferably m is an integer selected from 1 and 2.

Preferably n is an integer selected from 0 and 1, but most preferred n is 0.

The following preferred embodiments of compounds of the formula I are described using generic formula I.1 and I.2, wherein any tautomers, solvates, hydrates and salts thereof, in particular the pharmaceutically acceptable salts thereof, are encompassed.

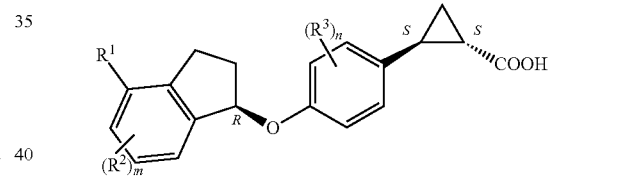

I.1

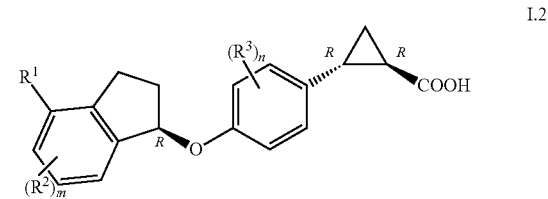

I.2

Examples of preferred subgeneric embodiments (E) according to the present invention are set forth in the following table 1, wherein each substituent group of each embodiment is defined according to the definitions set forth hereinbefore and wherein all other substituents of the formulas I, I.1 and I.2 are defined according to the definitions set forth hereinbefore:

TABLE 1

| E | $R^1$- | $R^2$- | $R^3$- | $R^{1a}$- | $R^{1b}$- | $R^{1c}$- | $R^N$- | $R^M$- | m | n |
|---|---|---|---|---|---|---|---|---|---|---|
| E1 | $R^1$-G1 | $R^2$-G1 | $R^3$-G1 | $R^{1a}$-G1 | $R^{1b}$-G1 | $R^{1c}$-G1 | $R^N$-G1 | $R^M$-G1 | 0-2 | 0-2 |
| E2 | $R^1$-G1 | $R^2$-G1 | $R^3$-G2 | $R^{1a}$-G2a | $R^{1b}$-G2 | $R^{1c}$-G2 | $R^N$-G1 | $R^M$-G1 | 0-2 | 0-2 |
| E3 | R1-G1 | $R^2$-G1 | $R^3$-G2 | $R^{1a}$-G2b | $R^{1b}$-G2 | $R^{1c}$-G2 | $R^N$-G1 | $R^M$-G1 | 0-2 | 0-2 |

TABLE 1-continued

| E | $R^1$- | $R^2$- | $R^3$- | $R^{1a}$- | $R^{1b}$- | $R^{1c}$- | $R^N$- | $R^M$- | m | n |
|---|---|---|---|---|---|---|---|---|---|---|
| E4 | $R^1$-G2 | $R^2$-G1 | $R^3$-G1 | $R^{1a}$-G1 | $R^{1b}$-G1 | $R^{1c}$-G1 | $R^N$-G1 | $R^M$-G1 | 0-2 | 0-2 |
| E5 | $R^1$-G2 | $R^2$-G1 | $R^3$-G2 | $R^{1a}$-G2a | $R^{1b}$-G2 | $R^{1c}$-G2 | $R^N$-G1 | $R^M$-G1 | 0-2 | 0-2 |
| E6 | $R^1$-G2 | $R^2$-G1 | $R^3$-G2 | $R^{1a}$-G2b | $R^{1b}$-G2 | $R^{1c}$-G2 | $R^N$-G1 | $R^M$-G1 | 0-2 | 0-2 |
| E7 | $R^1$-G2 | $R^2$-G2 | $R^3$-G2 | $R^{1a}$-G2a | $R^{1b}$-G2 | $R^{1c}$-G2 | $R^N$-G1 | $R^M$-G1 | 1, 2 | 0, 1 |
| E8 | $R^1$-G2 | $R^2$-G2 | $R^3$-G2 | $R^{1a}$-G2b | $R^{1b}$-G2 | $R^{1c}$-G2 | $R^N$-G1 | $R^M$-G1 | 1, 2 | 0, 1 |
| E9 | $R^1$-G2 | $R^2$-G2 | $R^3$-G2 | $R^{1a}$-G2a | $R^{1b}$-G2 | $R^{1c}$-G2 | $R^N$-G1 | $R^M$-G1 | 1 | 0 |
| E10 | $R^1$-G2 | $R^2$-G2 | $R^3$-G2 | $R^{1a}$-G2b | $R^{1b}$-G2 | $R^{1c}$-G2 | $R^N$-G1 | $R^M$-G1 | 1 | 0 |
| E11 | $R^1$-G2 | $R^2$-G2 | $R^3$-G2 | $R^{1a}$-G2a | $R^{1b}$-G2 | $R^{1c}$-G2 | $R^N$-G1 | $R^M$-G1 | 2 | 0 |
| E12 | $R^1$-G2 | $R^2$-G2 | $R^3$-G2 | $R^{1a}$-G2b | $R^{1b}$-G2 | $R^{1c}$-G2 | $R^N$-G1 | $R^M$-G1 | 2 | 0 |
| E13 | $R^1$-G3 | $R^2$-G2 | $R^3$-G2 | $R^{1a}$-G3a | $R^{1b}$-G3 | $R^{1c}$-G2 | $R^N$-G2 | $R^M$-G2 | 1, 2 | 0, 1 |
| E14 | $R^1$-G3 | $R^2$-G2 | $R^3$-G2 | $R^{1a}$-G3b | $R^{1b}$-G3 | $R^{1c}$-G2 | $R^N$-G2 | $R^M$-G2 | 1, 2 | 0, 1 |
| E15 | $R^1$-G3 | $R^2$-G2 | $R^3$-G3 | $R^{1a}$-G3a | $R^{1b}$-G3 | $R^{1c}$-G2 | $R^N$-G2 | $R^M$-G2 | 1 | 0 |
| E16 | $R^1$-G3 | $R^2$-G2 | $R^3$-G3 | $R^{1a}$-G3b | $R^{1b}$-G3 | $R^{1c}$-G2 | $R^N$-G2 | $R^M$-G2 | 1 | 0 |
| E17 | $R^1$-G3 | $R^2$-G2 | $R^3$-G3 | $R^{1a}$-G3a | $R^{1b}$-G3 | $R^{1c}$-G3 | $R^N$-G2 | $R^M$-G2 | 1 | 0 |
| E18 | $R^1$-G3 | $R^2$-G2 | $R^3$-G3 | $R^{1a}$-G3b | $R^{1b}$-G3 | $R^{1c}$-G3 | $R^N$-G2 | $R^M$-G2 | 1 | 0 |
| E19 | $R^1$-G3 | $R^2$-G2 | $R^3$-G3 | $R^{1a}$-G3a | $R^{1b}$-G3 | $R^{1c}$-G3 | $R^N$-G2 | $R^M$-G2 | 2 | 0 |
| E20 | $R^1$-G3 | $R^2$-G2 | $R^3$-G3 | $R^{1a}$-G3b | $R^{1b}$-G3 | $R^{1c}$-G3 | $R^N$-G2 | $R^M$-G2 | 2 | 0 |
| E21 | $R^1$-G3 | $R^2$-G2 | $R^3$-G3 | $R^{1a}$-G3a | $R^{1b}$-G3 | $R^{1c}$-G3 | $R^N$-G2 | $R^M$-G2 | 1 | 1 |
| E22 | $R^1$-G3 | $R^2$-G2 | $R^3$-G3 | $R^{1a}$-G3b | $R^{1b}$-G3 | $R^{1c}$-G3 | $R^N$-G2 | $R^M$-G2 | 1 | 1 |
| E23 | $R^1$-G4 | $R^2$-G3 | $R^3$-G4 | $R^{1a}$-G4a | $R^{1b}$-G4 | $R^{1c}$-G3 | $R^N$-G2 | $R^M$-G2 | 1, 2 | 0, 1 |
| E24 | $R^1$-G4 | $R^2$-G3 | $R^3$-G4 | $R^{1a}$-G4b | $R^{1b}$-G4 | $R^{1c}$-G3 | $R^N$-G2 | $R^M$-G2 | 1, 2 | 0, 1 |
| E25 | $R^1$-G4a | $R^2$-G3 | $R^3$-G4 | $R^{1a}$-G4a | $R^{1b}$-G4 | $R^{1c}$-G3 | $R^N$-G2 | $R^M$-G2 | 1, 2 | 0 |
| E26 | $R^1$-G4a | $R^2$-G3 | $R^3$-G4 | $R^{1a}$-G4b | $R^{1b}$-G4 | $R^{1c}$-G3 | $R^N$-G2 | $R^M$-G2 | 1, 2 | 0 |
| E27 | $R^1$-G4b | $R^2$-G3 | $R^3$-G4 | $R^{1a}$-G4a | $R^{1b}$-G4 | $R^{1c}$-G3 | $R^N$-G2 | $R^M$-G2 | 1, 2 | 0 |
| E28 | $R^1$-G4b | $R^2$-G3 | $R^3$-G4 | $R^{1a}$-G4b | $R^{1b}$-G4 | $R^{1c}$-G3 | $R^N$-G2 | $R^M$-G2 | 1, 2 | 0 |
| E29 | $R^1$-G4 | $R^2$-G3 | $R^3$-G4 | $R^{1a}$-G4a | $R^{1b}$-G4 | $R^{1c}$-G3 | $R^N$-G3 | $R^M$-G3 | 1, 2 | 0, 1 |
| E30 | $R^1$-G4 | $R^2$-G3 | $R^3$-G4 | $R^{1a}$-G4b | $R^{1b}$-G4 | $R^{1c}$-G3 | $R^N$-G3 | $R^M$-G3 | 1, 2 | 0, 1 |
| E31 | $R^1$-G4a | $R^2$-G3 | $R^3$-G4 | $R^{1a}$-G4a | $R^{1b}$-G4 | $R^{1c}$-G3 | $R^N$-G3 | $R^M$-G3 | 1 | 0 |
| E32 | $R^1$-G4a | $R^2$-G3 | $R^3$-G4 | $R^{1a}$-G4b | $R^{1b}$-G4 | $R^{1c}$-G3 | $R^N$-G3 | $R^M$-G3 | 1 | 0 |
| E33 | $R^1$-G4b | $R^2$-G3 | $R^3$-G4 | $R^{1a}$-G4a | $R^{1b}$-G4 | $R^{1c}$-G3 | $R^N$-G3 | $R^M$-G3 | 2 | 0 |
| E34 | $R^1$-G4b | $R^2$-G3 | $R^3$-G4 | $R^{1a}$-G4b | $R^{1b}$-G4 | $R^{1c}$-G3 | $R^N$-G3 | $R^M$-G3 | 2 | 0 |
| E35 | $R^1$-G5 | $R^2$-G3 | $R^3$-G4 | $R^{1a}$-G4a | $R^{1b}$-G4 | $R^{1c}$-G3 | $R^N$-G3 | $R^M$-G3 | 1 | 0 |
| E36 | $R^1$-G5 | $R^2$-G3 | $R^3$-G4 | $R^{1a}$-G4b | $R^{1b}$-G4 | $R^{1c}$-G3 | $R^N$-G3 | $R^M$-G3 | 1 | 0 |
| E37 | $R^1$-G5 | $R^2$-G3 | $R^3$-G5 | $R^{1a}$-G4a | $R^{1b}$-G4 | $R^{1c}$-G3 | $R^N$-G3 | $R^M$-G3 | 2 | 0 |
| E38 | $R^1$-G5 | $R^2$-G3 | $R^3$-G5 | $R^{1a}$-G4b | $R^{1b}$-G4 | $R^{1c}$-G3 | $R^N$-G3 | $R^M$-G3 | 2 | 0 |
| E39 | $R^1$-G5 | $R^2$-G3 | $R^3$-G5 | $R^{1a}$-G5a | $R^{1b}$-G5 | $R^{1c}$-G4 | $R^N$-G3 | $R^M$-G3 | 0, 1 | 0, 1 |
| E40 | $R^1$-G5 | $R^2$-G3 | $R^3$-G5 | $R^{1a}$-G5b | $R^{1b}$-G5 | $R^{1c}$-G4 | $R^N$-G3 | $R^M$-G3 | 0, 1 | 0, 1 |
| E41 | $R^1$-G5 | $R^2$-G3 | $R^3$-G5 | $R^{1a}$-G5a | $R^{1b}$-G5 | $R^{1c}$-G4 | $R^N$-G3 | $R^M$-G3 | 1 | 0 |
| E42 | $R^1$-G5 | $R^2$-G3 | $R^3$-G5 | $R^{1a}$-G5b | $R^{1b}$-G5 | $R^{1c}$-G4 | $R^N$-G3 | $R^M$-G3 | 1 | 0 |
| E43 | $R^1$-G5 | $R^2$-G3 | $R^3$-G5 | $R^{1a}$-G5a | $R^{1b}$-G5 | $R^{1c}$-G4 | $R^N$-G3 | $R^M$-G3 | 2 | 0 |
| E44 | $R^1$-G5 | $R^2$-G3 | $R^3$-G5 | $R^{1a}$-G5b | $R^{1b}$-G5 | $R^{1c}$-G4 | $R^N$-G3 | $R^M$-G3 | 2 | 0 |

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds according to the invention and their intermediates may be obtained using methods of synthesis which are known to the one skilled in the art and described in the literature of organic synthesis for example using methods described in "Comprehensive Organic Transformations, $2^{nd}$ edition", Richard C. Larock, Wiley-VCH, 2009., and "March's Advanced Organic Chemistry, $6^{th}$ edition", Michael B. Smith, Jerry March, Wiley Interscience, 2007. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man and described in the literature for example in "Protecting Groups, $3^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

The compounds of the invention I are preferably accessed from a precursor II that bears the carboxylic acid function in a protected or masked form as sketched in Scheme 1; $R^1$, $R^2$, $R^3$, m and n have the meanings as defined hereinbefore and hereinafter. Suited precursor groups for the carboxylic acid may be, e.g., a carboxylic ester, a carboxylic amide, cyano, an olefin, oxazole, or a thiazole. All these groups have been transformed into the carboxylic acid function by different means which are described in the organic chemistry literature and are known to the one skilled in the art. The preferred precursor group is a $C_{1-4}$-alkyl or benzyl carboxylate, each of which may be additionally mono- or polysubstituted with fluorine, methyl, and/or methoxy. These ester groups may be hydrolysed with an acid, such as hydrochloric acid or sulfuric acid, or an alkali metal hydroxide, such as lithium hydroxide, sodium hydroxide, or potassium hydroxide, to yield the carboxylic acid function; the hydrolysis is preferably conducted in aqueous solvents, such as water and tetrahydrofuran, 1,4-dioxane, alcohol, e.g. methanol, ethanol, and isopropanol, or dimethyl sulfoxide, at 0 to 120° C. A tert-butyl ester is preferably cleaved under acidic conditions, e.g. trifluoroacetic acid or hydrochloric acid, in a solvent such as dichloromethane, 1,4-dioxane, isopropanol, or ethyl acetate. A benzyl ester is advantageously cleaved using hydrogen in the presence of a transition metal, preferably palladium on carbon. Benzyl esters bearing electron donating groups, such as methoxy groups, on the aromatic ring may also be removed under oxidative conditions; ceric ammonium nitrate (CAN) or 2,3-dichloro-5,6-dicyanoquinone (DDQ) are two commonly used reagents for this approach.

Scheme 1: Liberation of Carboxylic Acid Function to Access Compounds of the Invention

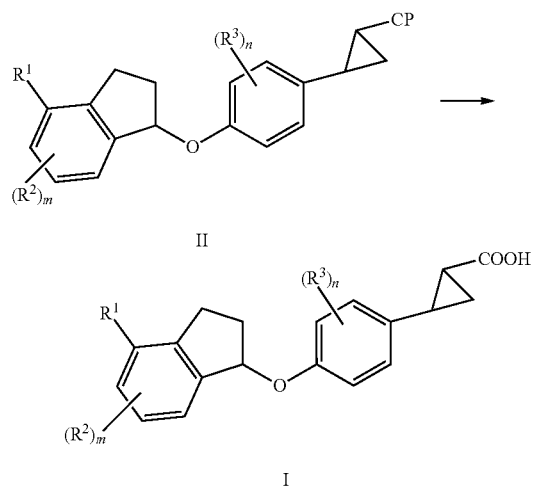

I
CP = masked or protected form of COOH, e.g., $CO_2C_{1-4}$-alkyl, $CO_2CH_2$aryl, $CON(C_{1-4}$-alkyl$)_2$, CN, CH=CH$_2$, thiazol-2-yl, oxazol-2-yl Compound II, in turn, may be obtained from indane III, which bears a leaving group, and phenol IV, which is decorated with the carboxylic acid precursor group (Scheme 2); $R^1$, $R^2$, $R^3$, m and n in Scheme 2 have the meanings as defined hereinbefore and hereinafter. The leaving group LG in III is replaced with the O in IV via a nucleophilic substitution; suited LG may be Cl, Br, I, methylsulfonyloxy, phenylsulfonyloxy, p-tolylsulfonyloxy, and trifluoromethylsulfonyloxy. The reaction is usually carried out in the presence of a base, such as triethylamine, ethyldiisopropylamine, 1,8-diazabicyclo[5.4.0]undecene, carbonates, e.g. $Li_2CO_3$, $Na_2CO_3$, $K_2CO_3$, and $Cs_2CO_3$, hydroxides, e.g. LiOH, NaOH, and KOH, alcoholates, e.g. NaOMe, NaOEt, and KOtBu, hydrides, e.g. NaH and KH, amides, e.g. $NaNH_2$, $KN(SiMe_3)_2$, and $LiN(iPr)_2$, and oxides, e.g. CaO and $Ag_2O$. Additives, such as silver salts, e.g. $AgNO_3$, $AgOSO_2CF_3$, and $Ag_2CO_3$, crown ethers, e.g. 12-crown-4,15-crown-5, and 18-crown-6, hexamethylphosphorus triamide (HMPT), and 1,3-dimethyl-3,4,5,6-dihydro-2-pyrimidinone (DMPU), may be beneficial or even essential for the reaction to proceed. Preferred solvents are dimethylsulfoxide, N,N-dimethylformamide, N,N-dimethylacetamide, N-methylpyrrolidinone, acetonitrile, acetone, 1,4-dioxane, tetrahydrofuran, alcohol, e.g. ethanol or isopropanol, water, or mixtures thereof, while not all of the solvents can be combined with each additive and base mentioned above. Suited reaction temperatures range from −20 to 140° C.

Scheme 2: Preparation of Precursor II

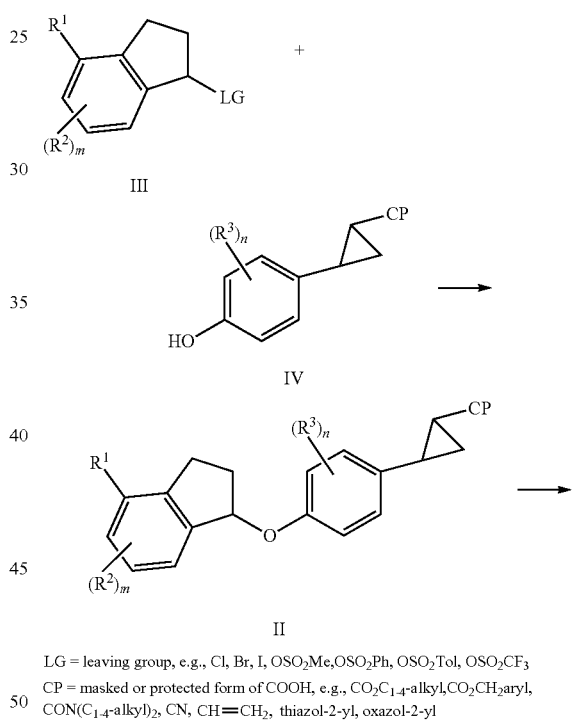

II
LG = leaving group, e.g., Cl, Br, I, $OSO_2Me$, $OSO_2Ph$, $OSO_2Tol$, $OSO_2CF_3$
CP = masked or protected form of COOH, e.g., $CO_2C_{1-4}$-alkyl, $CO_2CH_2$aryl, $CON(C_{1-4}$-alkyl$)_2$, CN, CH=CH$_2$, thiazol-2-yl, oxazol-2-yl An alternative reaction to combine building blocks III and IV is the Mitsunobu reaction or variations thereof (Scheme 3); $R^1$, $R^2$, $R^3$, m and n in Scheme 3 have the meanings as defined hereinbefore and hereinafter. The reaction is usually conducted with a phosphine and an azodicarboxylic ester or amide in tetrahydrofuran, 1,4-dioxane, diethyl ether, toluene, benzene, dichloromethane, or mixtures thereof, at −30 to 100° C. Phosphines often used are triphenylphosphine and tributylphosphine which are commonly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide.

Scheme 3: Mitsunobu Reaction to Access Precursor II

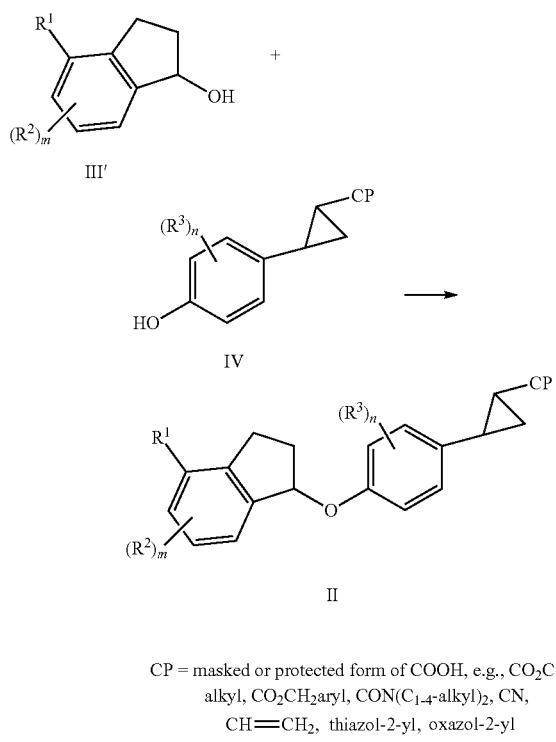

CP = masked or protected form of COOH, e.g., $CO_2C_{1-4}$-alkyl, $CO_2CH_2$aryl, $CON(C_{1-4}$-alkyl$)_2$, CN, CH=$CH_2$, thiazol-2-yl, oxazol-2-yl Intermediate III' is conveniently obtained from indanone V which, in turn, may be prepared from phenylpropionic acid derivative VI (Scheme 4); $R^1$, $R^2$, and m in Scheme 4 have the meanings as defined hereinbefore and hereinafter. For the intramolecular acylation (Friedel-Crafts acylation), VI→N, a considerable number of approaches has been reported. The reaction may be performed starting with a carboxylic acid, carboxylic ester, carboxylic anhydride, carboxylic chloride or fluoride, or a nitrile using a Lewis acid as catalyst. The following Lewis acids are some of the more often used ones: hydrobromic acid, hydroiodic acid, hydrochloric acid, sulfuric acid, phosphoric acid, $P_4O_{10}$, trifluoroacetic acid, methanesulfonic acid, toluenesulfonic acid, trifluoromethanesulfonic acid, $ClSO_3H$, $Sc(OSO_2CF_3)_3$, $Tb(OSO_2CF_3)_3$, $SnCl_4$, $FeCl_3$, $AlBr_3$, $AlCl_3$, $SbCl_5$, $BCl_3$, $BF_3$, $ZnCl_2$, montmorillonites, $POCl_3$, and $PCl_5$. The reaction may be conducted, e.g., in dichloromethane, 1,2-dichloroethane, nitrobenzene, chlorobenzene, carbon disulfide, mixtures thereof, or without an additional solvent in an excess of the Lewis acid, at 0 to 180° C. Carboxylic acids are preferably reacted in polyphosphoric acid at 0 to 120° C., while carboxylic chlorides are preferably reacted with $AlCl_3$ in dichloromethane or 1,2-dichloroethane at 0 to 80° C.

The subsequent reduction of the keto group in Scheme 4 is a standard transformation in organic synthesis, which may be accomplished with lithium borohydride, sodium borohydride, lithium aluminum hydride, or diisobutylaluminum hydride. While sodium borohydride is employed in aqueous or alcoholic solution at 0 to 60° C., the other reducing agents mentioned are preferably used in inert solvents, such as tetrahydrofuran, diethyl ether, dichloromethane, and toluene, at −80 to 60° C. The reduction of the keto group may also be conducted in a stereoselective fashion providing the alcohol in enantiomerically enriched or pure form. Suited chiral reducing agents are boranes combined with an enantiomerically pure [1,3,2]oxazaborol (Corey-Bakshi-Shibata reaction or Corey-Itsuno reaction) or formic acid, formates, hydrogen, or silanes in the presence of an enantiomerically pure transition metal catalyst. Typical reaction conditions for the former approach are borane (complexed with, e.g., dimethyl sulfide) and (R)- or (S)-3,3-diphenyl-1-methyltetrahydro-1H,3H-pyrrolo[1,2-c][1,3,2]oxazaborol in, e.g., dichloromethane, toluene, methanol, tetrahydrofuran, or mixtures thereof, at 0 to 60° C. Using a chiral transition metal catalyst, such as a ruthenium complex, e.g. chloro{[(1S,2S)-(−)-2-amino-1,2-diphenylethyl](4-toluenesulfonyl)-amido}-mesitylene)ruthenium(II), may deliver the hydroxy compound with high enantiomeric excess using, e.g., formic acid in the presence of a base, e.g. triethylamine, in dichloromethane, at −20 to 60° C.

Scheme 4: Preparation of Intermediate III'

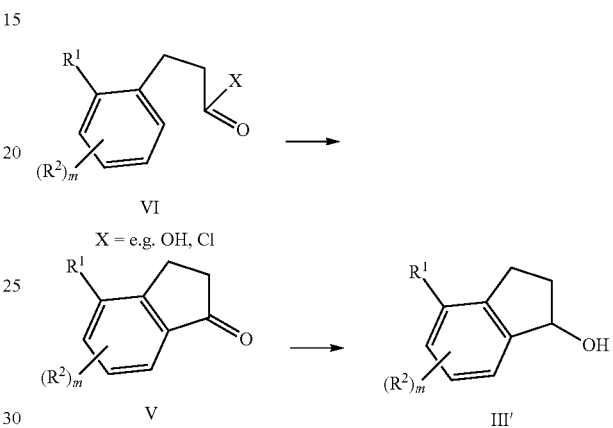

X = e.g. OH, Cl

Alternatively, indanone V can be synthesized as described in Scheme 5; $R^1$, $R^2$, and m have the meanings as defined hereinbefore and hereinafter. Starting with benzene VII and 3-halo-propionic acid or a derivative thereof or acrylic acid or a derivative thereof the required indanone V may be obtained via the combination of a Friedel-Crafts alkylation and acylation reaction in one pot or two separate reactions (eq. 1.)). These reactions are catalyzed by a Lewis acid, such as triflic acid, sulfuric acid, phosphoric acid, $AlCl_3$, $ZnCl_2$, and phosphorus pentoxide, and preferably conducted without additional solvent in an excess of the Lewis acid or in dichloromethane, 1,2-dichloroethane, cyclohexane, or carbon disulfide, at 0 to 140° C. A preferred combination comprises compound VI, 3-chloro-propionyl chloride, and $AlCl_3$ in dichloromethane or 1,2-dichlorethane at 20 to 80° C.

Starting with ethynylbenzene VIII indanone V is accessible by a transition metal catalyzed reaction with carbon monoxide (eq. 2.)). Rhodium is a preferred catalyst basis which is combined with a phosphine, e.g. triphenylphosphine, and a base, e.g. triethylamine, and used in a solvent, preferably tetrahydrofuran, at high carbon monoxide pressure, preferably 50 to 150 bar, at 150 to 200° C. (see e.g. *J. Org. Chem.* 1993, 58, 5386-92). Combination of 2-halo or pseudo-halo substituted styrene IX and carbon monoxide in the presence of a transition metal also allows the preparation of indanone V (eq. 3.)). Palladium catalysts are preferred and used with carbon monoxide or molybdenum hexacarbonyl as carbon monoxide source. Preferred solvents are N,N-dimethylformamide, N,N-dimethylacetamide, N-methylpyrrolidone, and 1,4-dioxane which are preferably employed at 20 to 150° C. by conventional heating or microwave irradiation. Pyridine and tetrabutylammonium chloride are preferred additives for this transformation (see e.g. *J. Am. Chem. Soc.* 2003, 125, 4804-7 and *J. Org. Chem.* 2005, 70, 346-9).

Scheme 5: Preparation of Intermediate V

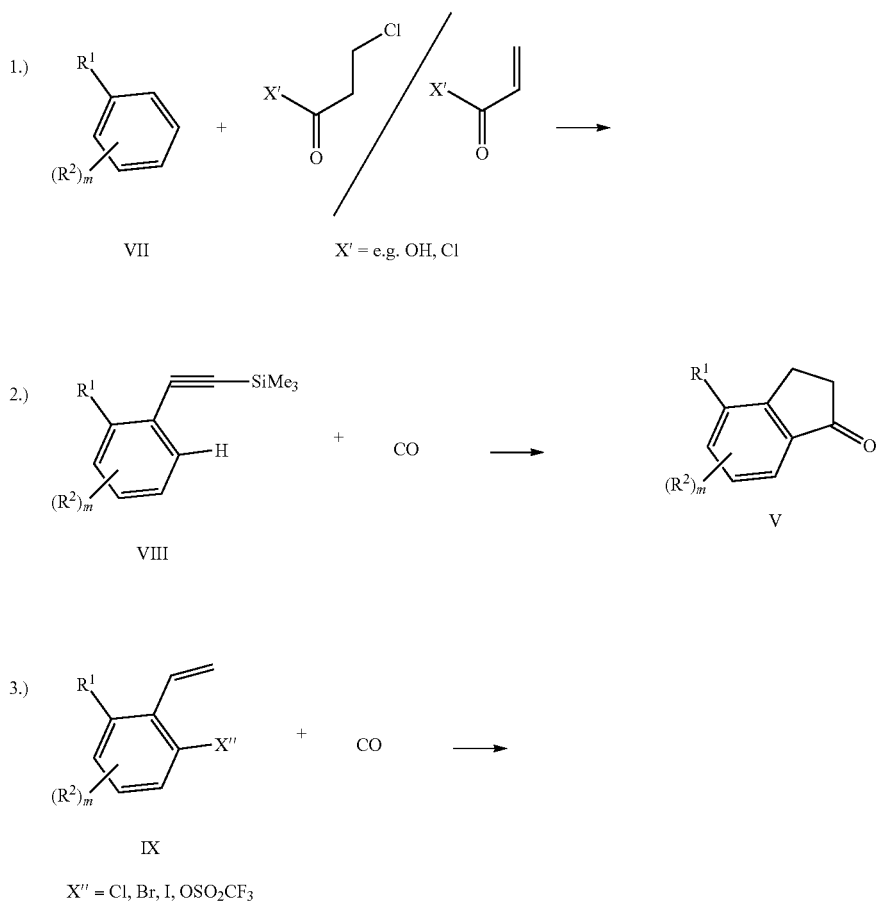

Compounds of general structure VI wherein $R^3$ and n have the meanings as defined hereinbefore and hereinafter and CP is a suitable carboxylic acid ester group can be synthesised as summarized in Scheme 6.

Substituted cinnamic acid ester X in which one substituent is a 4-oxy group protected with a suitable protecting group is reacted with a methylene synthetic equivalent to give cyclopropyl ester XI. Suitable reagents for this transformation include diazomethane in the presence of a transition metal catalyst such as palladium diacetate (e.g. WO2011/94890), trimethyloxosulfonium halide in the presence of a base such as sodium hydride (e.g. WO2005/103032) and diiodomethane in the presence of copper and zinc (e.g. U.S. Pat. No. 628,476). Generally the use of a trans-cinnamic acid ester in these reactions leads to predominant formation of an trans-substituted cyclopropyl ester.

Enantioselective reactions of this type can be performed using diazomethane and chiral copper complexes with moderate enantiomeric excesses (e.g. Charette et. al.; Tet. Asymmetry, 2003, 14, 867-872.).

The protecting group is then removed under suitable conditions to give IV.

Alternatively:

Substituted styrene XII in which one substituent is a 4-oxy group protected with a suitable protecting group is reacted with a diazoacetate ester XIII in the presence of a transition metal catalyst to give cyclopropyl ester XI. Suitable catalyst systems for this transformation include palladium diacetate (e.g. WO2007/104717), cobalt(II) porphyrins (e.g. WO2006/103503), rhodium complexes (e.g. WO2006/87169) and copper complexes (e.g. WO2010/51819) etc. Mixtures of cis and trans-cyclopropyl esters are generally formed with the trans-system generally predominant and the ratio depending on the catalyst system and substrates used.

Enantioselective reactions of this type can be performed using chiral copper complexes with good to excellent enantiomeric excesses according to the method of Evans et. al. (J. Am. Chem. Soc., 1991, 113, 726-728) and variations thereof.

The protecting group is then removed under suitable conditions to give IV.

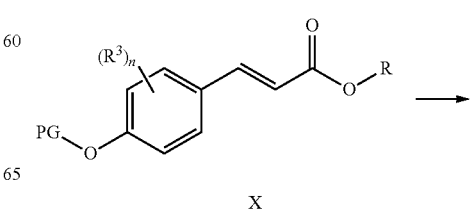

X

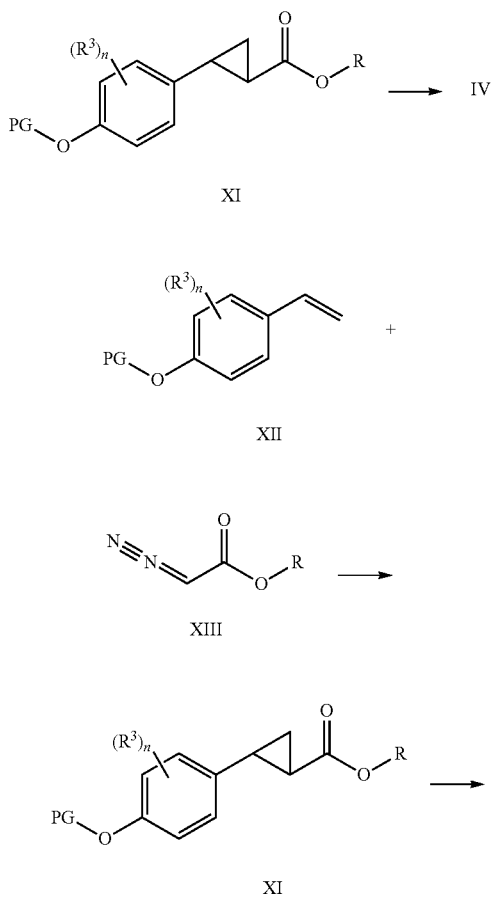

PG = protective group, e.g., Me, Bn, *t*Bu, *t*BuMe$_2$Si etc
R = ester protecting group of COOH, e.g., C1-4-alkyl, CH$_2$aryl For the stereoselective synthesis of compounds I of the invention with high enantiomeric excess intermediates XIVa, XIVb, and XVa, XVb are particularly useful and can be prepared as shown in Scheme 7.

The reaction of 4-tert-butyloxystyrene with a diazo acetate ester, in the presence of a complex of copper triflate and (R,R)-2,2'-isopropylidenebis(4-tert-butyl-2-oxazoline) leads to the formation of intermediate XIVa. Preferably the diazoacetate ester is diazoethyl acetate, preferably the reaction is carried out at reduced temperature, suitably at or below 0° C., more preferably in the range of −10° C. to −20° C. as by this means the product is conveniently obtained in high enantiomeric excess. A suitable method for removing the tert-butyl protecting group is by treatment with trifluoroacetic acid, which leads to intermediate XVa with no loss of enantiomeric excess. The use of (S,S)-2,2'-isopropylidenebis(4-tert-butyl-2-oxazoline) leads to enantiomers XIVb and XVb. The use of 4-methoxystyrene as an alternative starting material (as described in e.g. Benelkebir et. al., Bioorganic and Medicinal Chemistry, 2011, vol. 19, 3709-3716) is not suitable for this preperation as removal of the methyl protection under standard conditions (treatment with BBr$_3$) leads to racemisation.

Scheme 7: Stereoselective Synthesis of Intermediates XIVa, XIVb, and XVa, XVb

Note: Absolute stereochemistry assigned by analogy with Evans et. al., J. Am. Chem. Soc., 1991, 113, 726-728.

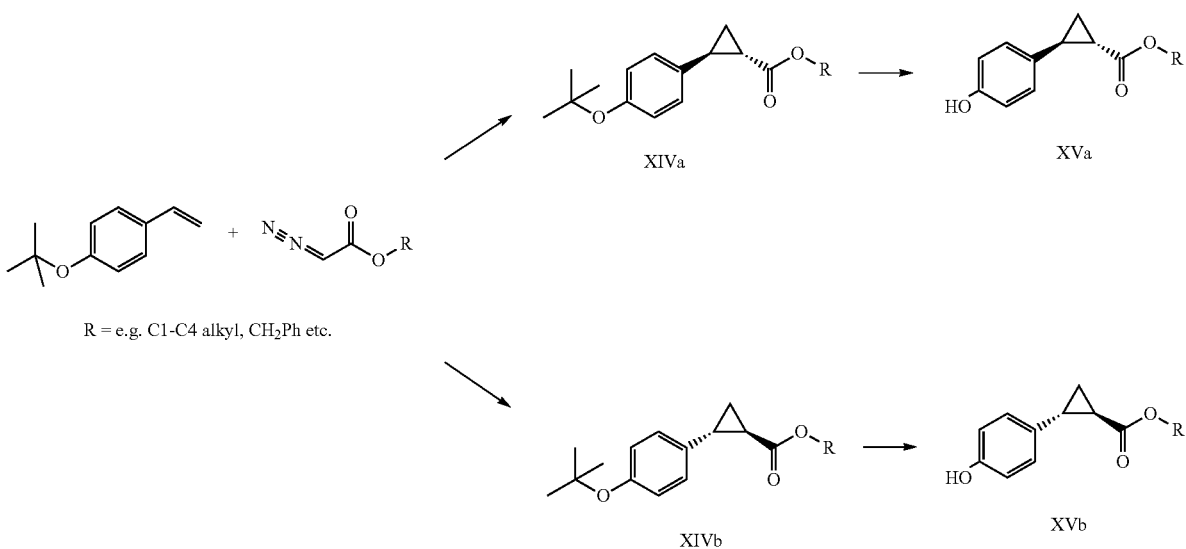

R = e.g. C1-C4 alkyl, CH$_2$Ph etc.

For compounds I of the invention in which $R^1$ is an aromatic or heteroaromatic group compounds of formula II can be prepared as shown in Scheme 8. Intermediates of formula XVI, synthesised by the methods described above, are allowed to react with a suitable reagent e.g. an aryl or heteroaryl boronic acid, aryl or heteroaryl boronic ester, aryl or heteroaryl stannane etc, aryl or heteroaryl zinc reagent etc. in a palladium catalysed cross coupling reaction (Suzuki, Stille, Nigishi or related reaction) using methods described in the literature and known to those skilled in the art.

Alternatively intermediates of formula XVI can be converted into boronic acids, boronic esters, stannanes, zinc reagents etc. XVII and then reacted with appropriate aryl or heteroaryl halide reagents or similar in a palladium catalysed cross coupling reaction (Suzuki, Stille, Nigishi or related reaction) according to methods described in the literature and known to those skilled in the art.

Scheme 8: Preparation of Precursor II where $R^1$ is Aryl or Heteroaryl

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active

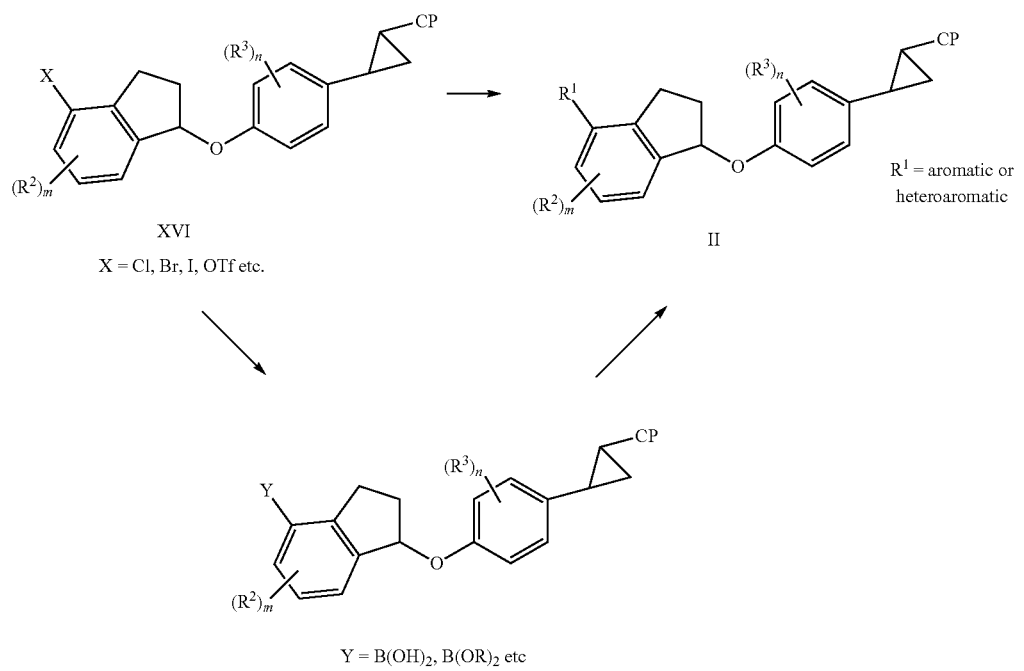

CP = masked or protected form of COOH, e.g., $CO_2C_{1-4}$-alkyl, $CO_2CH_2$aryl, $CON(C_{1-4}$-alkyl$)_2$, CN, CH=$CH_2$, thiazol-2-yl, oxazol-2-yl The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis for example in "Protecting Groups, $3^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the G-protein-coupled receptor GPR40 with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

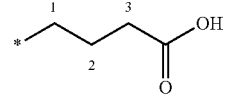

wherein the carboxy group is attached to the third carbon atom of the propyl group. The terms "1-methylpropyl-", "2,2-dimethylpropyl-" or "cyclopropylmethyl-" group represent the following groups:

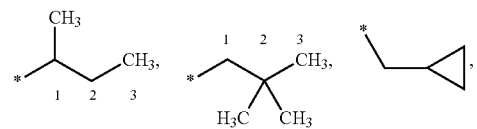

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals H₃C—, H₃C—CH₂—, H₃C—CH₂—CH₂—, H₃C—CH(CH₃)—, H₃C—CH₂—CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH₂)—, —(CH₂—CH₂)—, —(CH(CH₃))—, —(CH₂—CH₂—CH₂)—, —(C(CH₃)₂)—, —(CH(CH₂CH₃))—, —(CH(CH₃)—CH₂)—, —(CH₂—CH(CH₃))—, —(CH₂—CH₂—CH₂—CH₂)—, —(CH₂—CH₂—CH(CH₃))—, —(CH(CH₃)—CH₂—CH₂)—, —(CH₂—CH(CH₃)—CH₂)—, —(CH₂—C(CH₃)₂)—, —(C(CH₃)₂—CH₂)—, —(CH(CH₃)—CH(CH₃))—, —(CH₂—CH(CH₂CH₃))—, —(CH(CH₂CH₃)—CH₂)—, —(CH(CH₂CH₂CH₃))—, —(CHCH(CH₃)₂)— and —C(CH₃)(CH₂CH₃)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=CH₂, —CH=CH—CH₃, —CH₂—CH=CH₂.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH₃, —CH₂—C≡CH.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbornyl, norcaryl, adamantyl, etc.

Many of the terms given above may be used repeatedly in the definition of a formula or group and in each case have one of the meanings given above, independently of one another.

Pharmacological Activity

The activity of the compounds of the invention may be demonstrated using the following assay:

$IP_1$ accumulation measurements using the IPOne assay system—1321N1 cells stably expressing human GPR40 receptor (Euroscreen, Belgium) are seeded 24 h before the assay in black clear-bottom collagen-coated or white 384-well plates in culture medium containing 10% FCS, 1% Na-Pyruvate and 400 μg/mL G418. $IP_1$ is assayed according to the Manufacturer's description (Cisbio Bioassays, France). In brief, the assay is started by substitution of the culture medium by stimulation buffer (Hepes 10 mM, $CaCl_2$ 1 mM, $MgCl_2$ 0.5 mM, KCl 4.2 mM, NaCl 146 mM and glucose 5.5 mM, pH 7.4) without LiCl or with 50 nM LiCl. Cells are stimulated for 1 hour at 37° C., 5 or 10% $CO_2$ by addition of the compounds that are diluted in stimulation buffer containing LiCl yielding a final LiCl concentration of 50 mM. Assays are stopped by adding HTRF-conjugates (IP1-d2 and Anti-IP1 cryptate Tb) and lysis buffer, provided by the manufacturer. After an incubation time of 1 hour at room temperature plates are measured using an EnVision™, Perkin Elmer. The obtained fluorescence ratios at 665/615 nM are then used to calculate the $pEC_{50}$ values using GraphPad Prism 5 (Graphpad Software Inc, USA) or Assay Explorer 3.3 Software (Accelrys, Inc.) by interpolation using an $IP_1$ reference curve and subsequent sigmoidal curve fitting allowing for a variable hill slope.

The compounds according to the invention typically have $EC_{50}$ values in the range from about 1 nM to about 10 μM, preferably less than 1 μM, more preferably less than 100 nM.

$EC_{50}$ values for compounds according to the invention are shown in the following Table. The number of the compound corresponds to the number of the Example in the experimental section.

TABLE 2

| Example | $EC_{50}$ [nM] | Example | $EC_{50}$ [nM] | Example | $EC_{50}$ [nM] |
|---------|---------------|---------|---------------|---------|---------------|
| 1 | 50 | 22 | 12 | 44 | 12 |
| 2 | 15 | 23 | 13 | 45 | 2 |
| 3 | 36 | 24 | 18 | 46 | 6 |
| 4 | 18 | 25 | 13 | 47 | 191 |
| 5 | 85 | 26 | 8 | 48 | 6 |
| 6 | 98 | 27 | 8 | 49 | 5 |
| 7 | 531 | 28 | 6 | 50 | 11 |
| 8 | 407 | 29 | 7 | 51 | 569 |
| 9 | 457 | 30 | 18 | 52 | 38 |
| 10 | 13 | 31 | 6 | 53 | 13 |
| 11 | 9 | 32 | 4 | 54 | 5 |
| 12 | 328 | 33 | 2 | 55 | 75 |
| 13 | 13 | 34 | 8 | 56 | 224 |
| 14 | 8 | 35 | 28 | 57 | 1396 |
| 15 | 12 | 37 | 32 | 58 | 4 |
| 16 | 304 | 38 | 40 | 59 | 17 |
| 17 | 4 | 39 | 6 | 60 | 3 |
| 18 | 5 | 40 | 2 | 61 | 28 |
| 19 | 13 | 41 | 2 | 62 | 29 |
| 20 | 10 | 42 | 1 | 63 | 7 |
| 21 | 7 | 43 | 3 | 64 | 3 |

In view of their ability to modulate the activity of the G-protein-coupled receptor GPR40, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR40.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR40 in a patient, preferably in a human.

In yet another aspect the present invention relates to a method for treating a disease or condition mediated by the activation of the G-protein-coupled receptor GPR40 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR40 embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macro-angiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid) receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR40, in particular diseases or conditions as described hereinbefore and hereinafter.

In yet another aspect the present invention relates a method for treating a disease or condition mediated by the activation of the G-protein-coupled receptor GPR40 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Examples/Preliminary Remarks:

The terms "ambient temperature" and "room temperature" are used interchangeably and designate a temperature of about 20° C.

As a rule, $^1$H-NMR and/or mass spectra have been obtained for the compounds prepared. The $R_f$ values are determined using Merck silica gel 60 $F_{254}$ plates and UV light at 254 nm.

Analytical Methods $^1$H-NMR spectra were recorded at 25° C. on a Varian INOVA (500 MHz) spectrometer or a Varian (400 MHz) spectrometer.

GC (GC METHOD 1):

Instrument: GC/MS Thermo Scientific TRACE GC ULTRA, DSQ II MS single quadrupole

Column: Agilent DB-5MS, 25 m×0.25 mm×0.25 μm

Carrier gas: Helium, 1 mL/min constant flow

Oven Program: 50° C., to 100° C. in 10° C./min, to 200° C. in 20° C./min, to 320° C. in 30° C./min (hold 10 min).

Detection: DSQ II MS single quadrupole

Ion source: EI

Scan range: 50-450 amu

LC (LC METHOD 1):

Instrument: LC/MS Waters Acquity UPLC System DAD, SQD single quadrupole

Column: BEH C18 1.7 μm 2.1×50 mm, Temp 35° C.

Mobile phase: A=$H_2O$ 90%+$CH_3CN$ 10%+$NH_4COOH$ 5 mM

B=$CH_3CN$ 90%+$H_2O$ 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−.
Scan range: 90-900 amu
LC (LC METHOD 2):
  Instrument: LC/MS Waters Acquity UPLC System DAD, SQD single quadrupole
  Column: HSS C18 1.8 μm 2.1×50 mm, Temp 35° C.
  Mobile phase: A=$H_2O$ 90%+$CH_3CN$ 10%+$CF_3COOH$ 0.1%
B=$CH_3CN$ 90%+$H_2O$ 10%
Curve 2

| Time in min | % A | % B | flow rate in mL/min |
|---|---|---|---|
| 0.00 | 100 | 0 | 0.70 |
| 0.70 | 0 | 100 | 0.70 |
| 2.30 | 0 | 100 | 0.70 |
| 2.40 | 100 | 0 | 0.70 |
| 2.60 | 100 | 0 | 0.70 |

Detection: UV 254 nm
Detection: SQD, single quadrupole
Ion source: ES+/ES−.
Scan range: 90-900 amu
LC (LC METHOD 3):
  Instrument: LC/MS Waters Acquity UPLC System DAD, SQD single quadrupole
  Column: BEH C18 1.7 μm 2.1×50 mm, Temp 35° C.
  Mobile phase: A=$H_2O$ 90%+$CH_3CN$ 10%+$NH_4COOH$ 5 mM
B=$CH_3CN$ 90%+$H_2O$ 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−.
Scan range: 90-900 amu
LC (LC METHOD 4):
  Instrument: LC/MS ThermoFinnigan HPLC Surveyor DAD, MSQ single quadrupole
  Column: Synergi Hydro RP100A, 2.5 μm, 3×50 mm
  Mobile phase: A=$H_2O$ 90%+$CH_3CN$ 10%+$NH_4COOH$ 10 mM
B=$CH_3CN$ 90%+$H_2O$ 10%+$NH_4COOH$ 10 mM

| Time in min: | % A | % B | Flow rate in mL/min |
|---|---|---|---|
| 0.00 | 100 | 0 | 0.7 |
| 1.50 | 100 | 0 | 0.7 |
| 8.00 | 0 | 100 | 0.7 |
| 10.00 | 0 | 100 | 0.7 |
| 11.00 | 100 | 0 | 0.7 |
| 12.00 | 100 | 0 | 0.7 |

Detection: UV 254 nm
Detection: Finnigan MSQ, single quadrupole
Ion source: APCI+/−; APCIScan
range: 100-900 amu
LC (LC Method 5)
  Instrument: Agilent HPLC1100
  Column: Sunfire 4.6×100 mm, Temp 40° C.
  Mobile phase: A=$H_2O$ 90%+10% $CH_3CN$+$CF_3COOH$ 0.1%
B=$CH_3CN$ 90%+$H_2O$ 10%

| Time in min: | % A | % B | Flow rate in mL/min |
|---|---|---|---|
| 0.00 | 90 | 10 | 2 |
| 9.00 | 20 | 80 | 2 |
| 11 | 20 | 80 | 2 |
| 13 | 90 | 10 | 2 |

Detection: UV 254 nm
LC (LC Method 6)
  Instrument: LC/MS ThermoFinnigan HPLC Surveyor DAD, LCQFleet Ion Trap
  Column: Simmetry Shield RP8, 5 μm, 4.6×150 mm
  Mobile phase: A=$H_2O$ 90%+10% $CH_3CN$+HCOOH 0.1%
B=$CH_3CN$ 90%+$H_2O$ 10%+HCOOH 0.1%

| Time in min: | % A | % B | Flow rate in mL/min |
|---|---|---|---|
| 0.00 | 70 | 30 | 0.85 |
| 1.5 | 50 | 50 | 0.85 |
| 8.5 | 0 | 100 | 0.85 |
| 13.05 | 0 | 100 | 0.85 |
| 14.0 | 70 | 30 | 0.85 |
| 15.0 | 70 | 30 | 0.85 |

Detection: UV 254 nm
Detection: Finnigan LCQDuo, Ion Trap
Ion source: ES+
Scan range: 100-900 amu
LC (LC METHOD 7):
  Instrument: LC/MS ThermoFinnigan HPLC Surveyor DAD, MSQ single quadrupole
  Column: Synergi Hydro RP100A, 2.5 μm, 3×50 mm
  Mobile phase: A=$H_2O$ 90%+10% $CH_3CN$+$NH_4COOH$ 10 mM
B=$CH_3CN$ 90%+$H_2O$ 10%+$NH_4COOH$ 10 mM

| Time in min: | % A | % B | Flow rate in mL/min |
|---|---|---|---|
| 0.00 | 100 | 0 | 0.7 |
| 1.5 | 100 | 0 | 0.7 |
| 8.0 | 0 | 100 | 0.7 |
| 13.0 | 0 | 100 | 0.7 |
| 14.0 | 100 | 0 | 0.7 |
| 15.0 | 100 | 0 | 0.7 |

Detection: UV 254 nm
Detection: Finnigan MSQ, single quadrupole
Ion source: APCI+/APCI−
Scan range: 100-900 amu
LC (LC METHOD 8):
Instrument: LC/MS ThermoFinnigan HPLC Surveyor DAD, LCQFleet Ion Trap
Column: Symmetry Shield RP8, 5 μm, 4.6×150 mm
Mobile phase: A=$H_2O$ 90%+10% $CH_3CN$+HCOOH 0.1%
B=$CH_3CN$ 90%+$H_2O$ 10%+HCOOH 0.1%

| Time in min: | % A | % B | Flow rate in mL/min |
|---|---|---|---|
| 0.00 | 95 | 5 | 1 |
| 1.5 | 95 | 5 | 1 |
| 11.05 | 5 | 95 | 1 |
| 13.0 | 5 | 95 | 1 |
| 13.03 | 95 | 5 | 1 |
| 15.0 | 95 | 5 | 1 |

Detection: UV 254 nm
Detection: Finnigan Fleet, Ion Trap
Ion source: ES+
Scan range: 100-900 amu
LC (LC METHOD 9):
Instrument: LC/MS Waters Alliance 2695 HPLC System DAD, Quattro Micro Triple quadrupole
Column: Atlantis dC18 5 μm 4.6×50 mm, Temp 35° C.
Mobile phase: A=$H_2O$ 90%+10% $CH_3CN$+$CF_3COOH$ 0.05%
B=$CH_3CN$ 90%+10% $H_2O$

| Time in min: | % A | % B | Flow rate in mL/min |
|---|---|---|---|
| 0.00 | 100 | 0 | 1.3 |
| 0.7 | 100 | 0 | 1.3 |
| 4.5 | 0 | 100 | 1.3 |
| 5.8 | 0 | 100 | 1.3 |
| 6.0 | 100 | 0 | 1.3 |

Detection: UV 254 nm
Detection: Quattro Micro, triple quadrupole
Ion source: ES+
Scan range: 90-1000 amu
LC (LC METHOD 10):
Instrument: LC/MS ThermoFinnigan HPLC Surveyor DAD, LCQFleet Ion Trap
Column: Xselect CSH, 2.5 μm, 4.6×50 mm
Mobile phase: A=$H_2O$ 90%+10% $CH_3CN$+HCOOH 0.1%
B=$CH_3CN$ 90%+$H_2O$ 10%+HCOOH 0.1%

| Time in min: | % A | % B | Flow rate in mL/min |
|---|---|---|---|
| 0.00 | 100 | 0 | 1.4 |
| 1 | 100 | 0 | 1.4 |
| 8.50 | 0 | 100 | 1.4 |
| 10.0 | 0 | 100 | 1.4 |
| 10.2 | 100 | 0 | 1.4 |
| 11.0 | 100 | 0 | 1.4 |

Detection: UV 254 nm
Detection: Finnigan Fleet, Ion Trap
Ion source: ES+
Scan range: 100-900 amu
LC (LC METHOD 11):
Instrument: LC/MS ThermoFinnigan HPLC Surveyor DAD, LCQFleet Ion Trap
Column: Xselect CSH, 2.5 μm, 4.6×50 mm
Mobile phase: A=$H_2O$ 90%+10% $CH_3CN$+HCOOH 0.1%
B=$CH_3CN$ 90%+$H_2O$ 10%+HCOOH 0.1%

| Time in min: | % A | % B | Flow rate in mL/min |
|---|---|---|---|
| 0.00 | 100 | 0 | 1.4 |
| 4.00 | 0 | 100 | 1.4 |
| 5.30 | 0 | 100 | 1.4 |
| 5.50 | 100 | 0 | 1.4 |
| 6.00 | 100 | 0 | 1.4 |

Detection: UV 254 nm
Detection: Finnigan Fleet, Ion Trap
Ion source: ES+Scan range: 100-900 amu
LC (LC METHOD 12):
Instrument: LC/MS ThermoFinnigan HPLC Surveyor DAD, MSQ single quadrupole
Column: Synergi Hydro RP100A, 2.5 μm, 3×50 mm
Mobile phase: A=H2O 90%+10% CH3CN+NH4COOH 5 mM
B=CH3CN 90%+H2O 10%

| Time in min: | % A | % B | Flow rate in mL/min |
|---|---|---|---|
| 0.00 | 100 | 0 | 1.2 |
| 4.00 | 0 | 100 | 1.2 |
| 5.30 | 0 | 100 | 1.2 |
| 5.50 | 100 | 0 | 1.2 |
| 6.00 | 100 | 0 | 1.2 |

Detection: UV 254 nm
Detection: Finnigan MSQ, single quadrupole
Ion source: APCI+/APCI−
Scan range: 100-900 amu
LC (LC METHOD 13):
Instrument: LC/MS Waters Acquity UPLC System DAD, SQD single quadrupole
Column: Waters Sunfire, 3×30 mm, 2.5 μm
Mobile phase: A=H2O+0.1% TFA
B=CH3CN

| Time in min: | % A | % B | Flow rate in mL/min |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Temp 60° C.
Detection: UV 254 nm
Detection: SQD, single quadrupole
Ion source: ES+/ES−
Scan range: 90-900 amu
LC (LC METHOD 14):
Instrument: LC/MS Waters Acquity UPLC System DAD, SQD single quadrupole
Column: Sunfire C18, 2.1×30 mm, 2.5 μm
Mobile phase: A=H2O+0.1% TFA
B=CH3CN

| Time in min: | % A | % B | Flow rate in mL/min |
| --- | --- | --- | --- |
| 0.00 | 99 | 1 | 1.5 |
| 0.02 | 99 | 1 | 1.5 |
| 1.00 | 0 | 100 | 1.5 |
| 1.10 | 0 | 100 | 1.5 |

Temp 60° C.
Detection: UV 254 nm
Detection: SOD, single quadrupole
Ion source: ES+/ES−
Scan range: 90-900 amu
LC (LC METHOD 15):
Instrument: Agilent 1100 with DAD, Gilson Autosampler and MS-Detector
Column: SunFire C18 4.6×30 mm, 3.5 μm
Mobile phase: A=H2O+0.1% TFA
B=CH3CN

| Time in min: | % A | % B | Flow rate in mL/min |
| --- | --- | --- | --- |
| 0.00 | 98 | 2 | 2.5 |
| 1.50 | 0 | 100 | 2.5 |
| 1.80 | 0 | 100 | 2.5 |

Temp 60° C.
Detection: UV 254 nm
Detection: single quadrupole
Ion source: ES+/ES−
Scan range: 90-900 amu

SYNTHESIS OF INTERMEDIATES

Intermediate 1

2-(4-Hydroxy-phenyl)-trans-cyclopropanecarboxylic acid ethyl ester

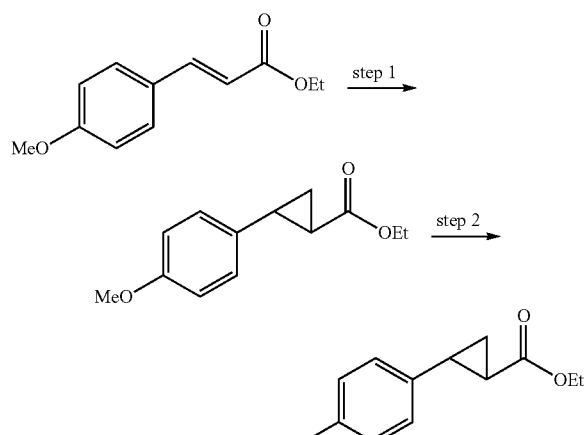

Step 1:
2-(4-Methoxy-phenyl)-trans-cyclopropanecarboxylic acid ethyl ester

Trimethylsulfoxonium iodide (14.15 g, 63 mmol) is suspended in dry DMSO (126 mL) and Sodium hydride (60% in mineral oil, 2.52 g, 63 mmol) is added. The mixture is stirred for 40 minutes and then a solution of 4-methoxycinnamic acid ethyl ester (5 g, 24.2 mmol) in dry DMSO (64 mL) is added and the mixture stirred for 3 hours at room temperature. The mixture is diluted with water and extracted with ethyl acetate, the organic phase is dried by passing through a phase seperator and the solvent is removed under vacuum. The residue is purified by flash chromatography (10% ethyl acetate in cyclohexane) to give the title compound (yield 1.43 g).

LC (LC METHOD 6): $t_R$=7.74 min; Mass spectrum (ESI$^+$): m/z=221 [M+H]$^+$.

Step 2:
2-(4-Hydroxy-phenyl)-trans-cyclopropanecarboxylic acid ethyl ester 2-(4-Methoxy-phenyl)-trans-cyclopropanecarboxylic acid ethyl ester (1.43 g, 6.51 mmol) is dissolved in dry dichloromethane (30 mL) and cooled to −78° C. Boron tribromide solution (1 M in dichloromethane, 7.81 mL, 7.81 mmol) is added dropwise then the mixture is allowed to warm to −20° C. and stirred overnight at −20° C. Ethanol (3 mL) is added and the mixture warmed to room temperature then diluted with saturated aqueous sodium bicarbonate solution. The phases are separated and the aqueous phase extracted with dichloromethane. The combined organic phases are dried through a phase seperator and the solvent removed under vacuum. The residue is purified by flash chromatography (10% ethyl acetate in cyclohexane) and then crystallised from 10% ethyl acetate in cyclohexane to give the title compound (yield 0.58 g).

LC (LC METHOD 6): $t_R$=6.25 min; Mass spectrum (ESI$^+$): m/z=248 [M+H+MeCN]$^+$.

Intermediate 2

2-(2-Fluoro-4-hydroxy-phenyl)-trans-cyclopropanecarboxylic acid methyl ester

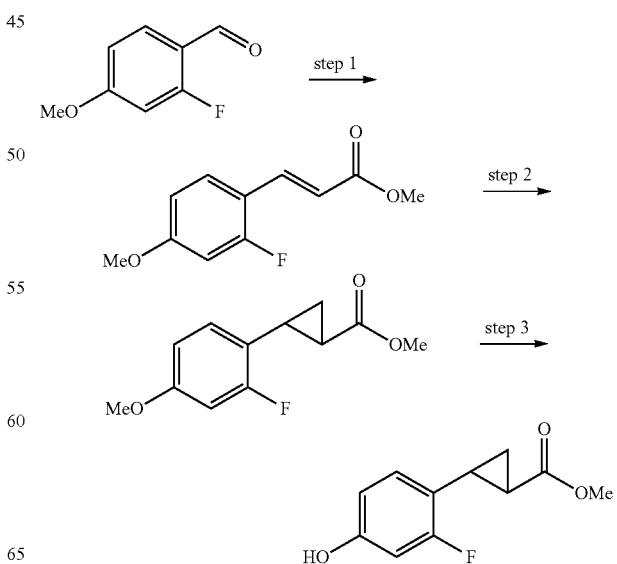

Step 1: 2-Fluoro-4-methoxycinnamic acid methyl ester

Sodium hydride (60% in mineral oil, 3.11 g, 77.86 mmol) is suspended in dry tetrahydrofuran (160 mL) and cooled to 0° C. Trimethylphosphonoacetate (14.18 g, 77.86 mmol) is added and the mixture stirred at 0° C. for 30 minutes. 2-Fluoro-4-methoxybenzaldehyde (10 g, 64.88 mmol) is added and the mixture stirred overnight at room temperature. (Carbethoxymethylene)triphenylphosphorane (11.3 g, 32.44 mmol) is added and the mixture stirred for 3 hours. Saturated aqueous ammonium chloride solution is added and the mixture extracted with ethyl acetate. The organic phase is dried and the solvent removed under vacuum. The residue is purified by flash chromatography (5% ethyl acetate in cyclohexane) to give the title compound (yield 13.85 g).

LC (LC METHOD 3): $t_R$=1.15 min; Mass spectrum (ESI$^+$): m/z=211 [M+H]$^+$.

Step 2: 2-(2-Fluoro-4-methoxy-phenyl)-trans-cyclopropanecarboxylic acid methyl ester The title compound is prepared from 2-Fluoro-4-methoxycinnamic acid methyl ester (13.85 g) in a manner analogous to that described for Intermediate 1, step 1. (yield 1.53 g).

LC (LC METHOD 3): $t_R$=1.22 min; Mass spectrum (ESI$^+$): m/z=225 [M+H]$^+$.

Step 3: 2-(2-Fluoro-4-hydroxy-phenyl)-trans-cyclopropanecarboxylic acid methyl ester The title compound is prepared from 2-(2-Fluoro-4-methoxy-phenyl)-trans-cyclopropanecarboxylic acid methyl ester (1.51 g) in a manner analogous to that described for Intermediate 1, step 2. (yield 0.71 g).

LC (LC METHOD 3): $t_R$=0.92 min; Mass spectrum (ESI): m/z=209 [M−H]$^-$.

Intermediate 3

2-(2-Methoxy-4-hydroxy-phenyl)-trans-cyclopropanecarboxylic acid methyl ester

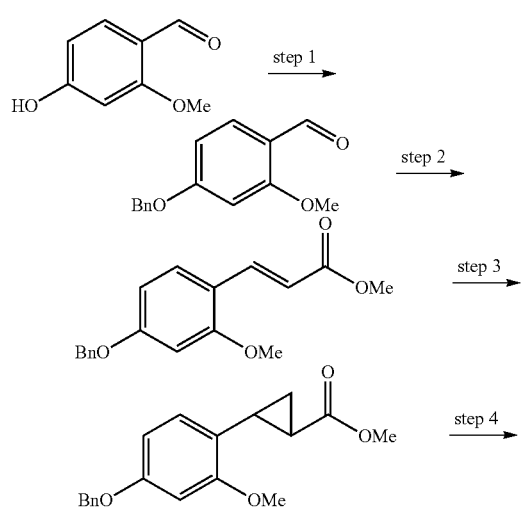

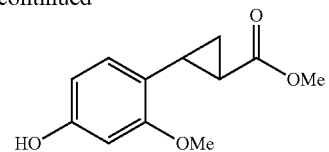

Step 1: 4-Benzyloxy-2-methoxy-benzaldehyde

4-Hydroxy-2-methoxybenzaldehyde (2.0 g, 13.15 mmol), benzyl bromide (3.14 mL, 26.3 mmol) and potassium carbonate (3.63 g, 26.3 mmol) are combined in acetone (5 mL) and the mixture is stirred for 4 hours. The mixture is concentrated under vacuum, suspended in dichloromethane and washed with water. The organic phase is concentrated under vacuum and the residue purified by flash chromatography (10% ethyl acetate in cyclohexane) to give the title compound (yield 2.0 g).

LC (LC METHOD 3): $t_R$=1.21 min; Mass spectrum (ESI$^+$): m/z=243 [M+H]$^+$.

Step 2: 4-Benzyloxy-2-methoxycinnamic acid methyl ester

The title compound is prepared from 4-Benzyloxy-2-methoxy-benzaldehyde (2.0 g 8.26 mmol) in a manner analogous to that described for Intermediate 2, step 1 (yield 2.1 g).

LC (LC METHOD 4): $t_R$=7.53 min; Mass spectrum (ESI$^+$): m/z=299 [M+H]$^+$.

Step 3: 2-(4-Benzyloxy-2-methoxy-phenyl)-trans-cyclopropanecarboxylic acid methyl ester The title compound is prepared from 4-Benzyloxy-2-methoxycinnamic acid methyl ester (2.1 g, 5.49 mmol) in a manner analogous to that described for Intermediate 1, step 1 (yield 500 mg).

LC (LC METHOD 4): $t_R$=7.53 min; Mass spectrum (ESI$^+$): m/z=313 [M+H]$^+$.

Step 4: 2-(4-Hydroxy-2-methoxy-phenyl)-trans-cyclopropanecarboxylic acid methyl ester 2-(4-Benzyloxy-2-methoxy-phenyl)-trans-cyclopropanecarboxylic acid methyl ester (500 mg, 1.6 mmol) is dissolved in ethyl acetate (10 mL) and hydrogenated for 2 hours in a Parr apparatus at 1 bar using 10% Pd/C as the catalyst. The solution is filtered through celite and the solvent removed under vacuum to give the title compound (yield 355 mg).

LC (LC METHOD 3): $t_R$=0.89 min; Mass spectrum (ESI$^-$): m/z=221 [M−H]$^-$.

Intermediate 4

(1S,2S)-2-(4-Hydroxy-phenyl)-cyclopropanecarboxylic acid ethyl ester

Note: Absolute stereochemistry assigned by analogy with Evans et. al., J. Am. Chem. Soc., 1991, 113, 726-728.

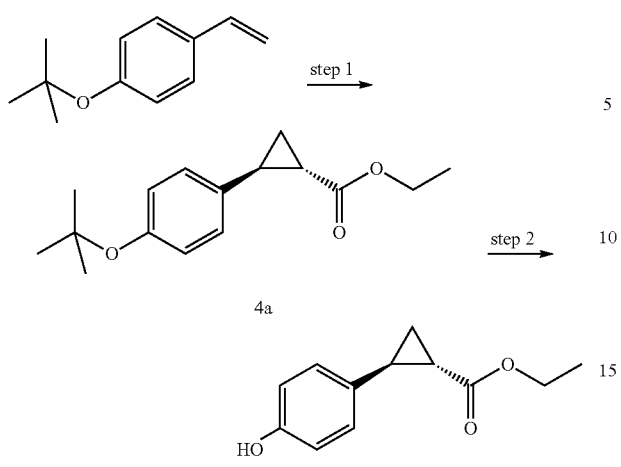

Step 1: (1S,2S)-2-(4-tert-Butoxy-phenyl)-cyclopropanecarboxylic acid ethyl ester (4a)

In a one liter three necked flask equipped with a magnetic stirrer bar, an alcohol thermometer, nitrogen inlet and addition inlet sealed with a suba seal, (R,R)-2,2'-isopropylidenebis(4-tert-butyl-2-oxazoline) (417 mg, 1.42 mmol) and copper(I) trifluoromethanesulfonate benzene complex (714 mg, 1.42 mmol) are dissolved in degassed tert-butyl methyl ether (120 mL) and stirred for 15 minutes under $N_2$.

4-tert-butoxystyrene (25 g, 142 mmol) is added and the mixture cooled to −10° C. (internal temperature) under $N_2$.

Ethyldiazoacetate (24.75 g, 184.4 mmol) is dissolved in 50 mL of tert-butyl methyl ether and 5 mL of the resulting solution is added dropwise with cooling over 30 minutes using a syringe pump. The addition is then stopped and the mixture stirred at −10° C. until the reaction starts (effervescence and colour change).

Once the reaction has started the mixture is cooled to −20° C. and the remaining solution added dropwise using a syringe pump over 3 hours maintaining the temperature at −20° C. Once the addition is completed the mixture is allowed to slowly warm to room temperature and stirred overnight.

NMR of a reaction sample shows approx 30% of unreacted starting material, therefore the mixture is cooled to −20° C. and a further 14.1 g of ethyl diazoacetate in 30 mL of tert-butyl methyl ether is added dropwise over 90 minutes, stirred for 1 hour at −20° C. and then allowed to warm to room temperature.

The solvent is removed under vacuum and the residue is purified by flash chromatography (0-5% EtOAc in cyclohexane) to give the title compound (yield 29.7 g).

LC (GC METHOD 1): $t_R$=11.47 min; Mass spectrum (EI+): m/z=262 [M]$^+$, e.e. 96% by chiral HPLC (Column: Daicel Chiralcel OJ-H, 4.6×250 mm, 5 μm Mobile phase: hexane:ethanol 95:5, 1 mL/min, 25° C.) $t_R$=9.87 (9.13) min Step 2: (1S,2S)-2-(4-Hydroxy-phenyl)-cyclopropanecarboxylic acid ethyl ester.

(1S,2S)-2-(4-tert-Butoxy-phenyl)-cyclopropanecarboxylic acid ethyl ester (10.5 g, 35.62 mmol) is dissolved in trifluoroacetic acid (15 mL, 195.6 mmol) and stirred for 5 minutes. The mixture is concentrated under vacuum, then reevaporated five times from dichloromethane. The residue is dissolved in boiling cyclohexane (20 mL) and then allowed to cool. The cyclohexane layer is decanted off and the operation repeated. The residue is dried under vacuum to give the title compound (yield 6.51 g).

LC (GC METHOD 1): $t_R$=11.04 min; Mass spectrum (EI+): m/z=206 [M]$^+$, e.e. 96% by chiral HPLC (Column: Daicel Chiralpak AS-H, 4.6×250 mm, 5 μm Mobile phase: hexane:ethanol 95:5, 1 mL/min, 25° C.) $t_R$=14.17 (13.11) min Intermediate 5

(1R,2R)-2-(4-Hydroxy-phenyl)-cyclopropanecarboxylic acid ethyl ester

Note: Absolute stereochemistry assigned by analogy with Evans et. al., J. Am. Chem. Soc., 1991, 113, 726-728.

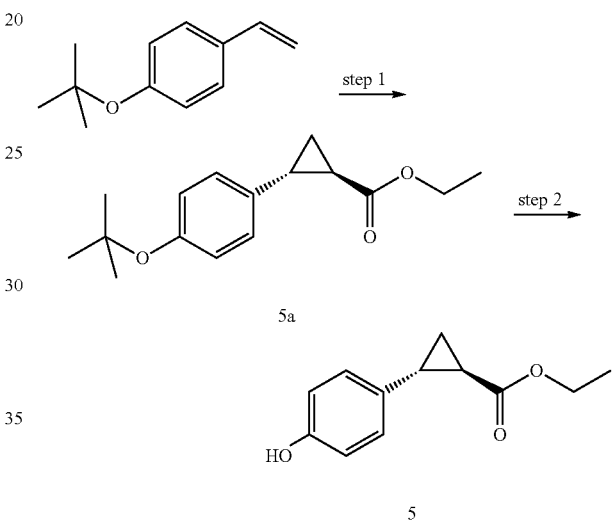

Step 1: (1R,2R)-2-(4-tert-Butoxy-phenyl)-cyclopropanecarboxylic acid ethyl ester (5a)

The title compound is prepared from 4-tert-butoxystyrene (4.3 g, 24.4 mmol) in a manner analogous to that described for Intermediate 4, step 1, using (S,S)-2,2'-isopropylidenebis(4-tert-butyl-2-oxazoline) (72 mg, 0.24 mmol) as the ligand (yield 6.4 g). LC (GC METHOD 1): $t_R$=11.47 min; Mass spectrum (EI+): m/z=262 [M]+, e.e. 94% by chiral HPLC. (Column: Daicel Chiralcel OJ-H, 4.6×250 mm, 5 μm Mobile phase: hexane:ethanol 95:5, 1 mL/min, 25° C.) $t_R$=8.94 (9.93) min Step 2: (1R,2R)-2-(4-Hydroxy-phenyl)-cyclopropanecarboxylic acid ethyl ester.

(1R,2R)-2-(4-tert-Butoxy-phenyl)-cyclopropanecarboxylic acid ethyl ester (5.9 g, 22.5 mmol) is cooled to 0° C. and trifluoroacetic acid (14 mL, 182.5 mmol) is added. The mixture is stirred for 5 minutes and then concentrated under vacuum. The residue is reevaporated 3 times from dichloromethane then purified by flash chromatography (0-10% ethyl acetate in cyclohexane) to give the title compound (yield 3.10 g).

LC (GC METHOD 1): $t_R$=11.04 min; Mass spectrum (EI+): m/z=206 [M]+, e.e. 94% by chiral HPLC (Column:

Daicel Chiralpak AS-H, 4.6×250 mm, 5 μm Mobile phase: hexane:ethanol 95:5, 1 mL/min, 25° C.) $t_R$=13.06 (14.29) min

Intermediate 6

(S)-4-Trifluoromethoxy-indan-1-ol

Note: Absolute stereochemistry assigned by analogy with Novori et. al., J. Am. Chem. Soc., 1995, 117 (28), pp 7562-7563.

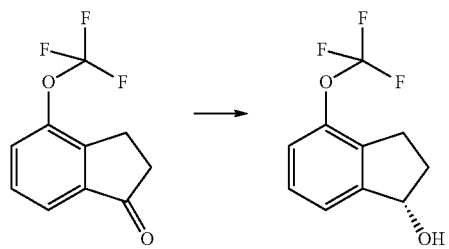 [SMILES: O=C1CCc2c(OC(F)(F)F)cccc21 ; O[C@H]1CCc2c(OC(F)(F)F)cccc21]

Triethylamine (5.23 mL, 37.2 mmol) is dissolved in dichloromethane (60 mL) and cooled to 0° C. then formic acid (1.60 mL, 42.4 mmol) is added dropwise with cooling. 4-Trifluoromethoxy-indan-1-one (US patent 2011/53974, 2.58 g, 11.94 mmol) is added and the mixture degassed with a flow of argon. Chloro([(1S,2S)-(+2-amino-1,2-diphenylethyl]-4-toluenesulfonyl)amido)(mesitylene)ruthenium(II) complex (148 mg, 0.24 mmol) is added and the mixture is stirred overnight under argon at room temperature. Water is added, the mixture shaken and the phases separated. The organic phase is dried and concentrated under vacuum. The residue is purified by flash chromatography (20% ethyl acetate in cyclohexane) to give the title compound (yield 2.50 g).

$^1$H NMR (DMSO-d$_6$) δ 1.77-1.87 (1H, m) 2.33-2.43 (1H, m) 2.68-2.79 (1H, m) 2.92-3.00 (1H, m) 5.06-5.15 (1H, q) 5.37-5.44 (1H, d) 7.20 (1H, d) 7.34 (1H, t) 7.36 (1H, t).

e.e. 99.2% by chiral HPLC (Column: Daicel Chiralcel OJ-H, 4.6×250 mm, 5 μm Mobile phase: hexane:ethanol 95:5, 1 mL/min, 25° C.) $t_R$=5.47 (5.19) min

Intermediate 7

(S)-4-Trifluoromethyl-indan-1-ol

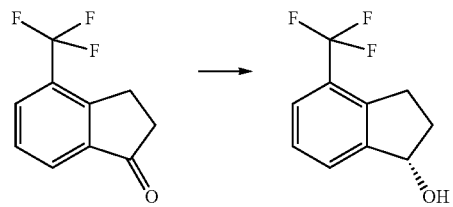 [SMILES: O=C1CCc2c1cccc2C(F)(F)F ; O[C@H]1CCc2c1cccc2C(F)(F)F]

The title compound is prepared from 4-trifluoromethyl-indan-1-one (30 g, 149.9 mmol) in a manner analogous to that described for Intermediate 6 (Yield 24.56 g).

LC (GC METHOD 1): $t_R$=7.64 min; Mass spectrum (EI+): m/z=202 [M]+, e.e. 100% by chiral HPLC (Column: Daicel Chiralpak AD-H, 4.6×250 mm, 5 μm Mobile phase: hexane:isopropanol 75:25, 1 mL/min, 25° C.) $t_R$=3.82 min.

Intermediate 8

(S)-4-Bromo-7-fluoro-indan-1-ol

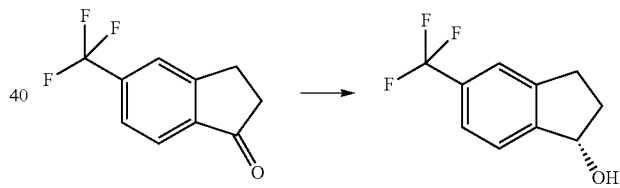

The title compound is prepared from 4-bromo-7-fluoro-indan-1-one (European patent EP2042480, 13.8 g, 60.25 mmol) in a manner analogous to that described for Intermediate 6 (Yield 13.08 g).

LC (GC METHOD 1): $t_R$=9.35 min; Mass spectrum (EI+): m/z=229 [M]+, e.e. 100% by chiral HPLC (Column: Daicel Chiralcel OJ-H, 4.6×250 mm, 5 μm Mobile phase: hexane:ethanol 95:5, 1 mL/min, 25° C.) $t_R$=9.87 min.

Intermediate 9

(S)-5-Trifluoromethyl-indan-1-ol

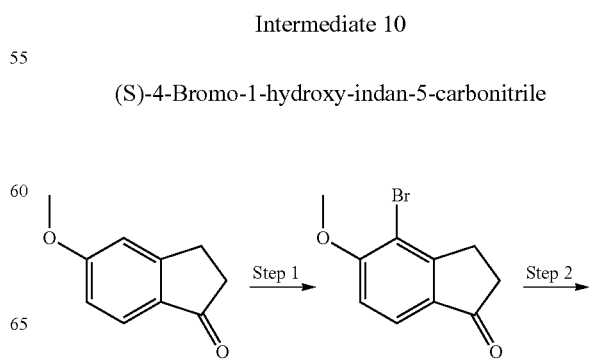

The title compound is prepared from 5-trifluormethyl-indan-1-one (1 g, 5.00 mmol) in a manner analogous to that described for Intermediate 6 (Yield 0.85 g).

$^1$H NMR (CDCl$_3$) δ 1.89-2.02 (1H, m) 2.11-2.18 (1H, m) 2.45-2.60 (1H, m) 2.78-2.90 (1H, m) 3.01-3.11 (1H, m) 5.23-2.25 (1H, m) 7.49 (3H, s). e.e. 98.6% by chiral HPLC.

Intermediate 10

(S)-4-Bromo-1-hydroxy-indan-5-carbonitrile

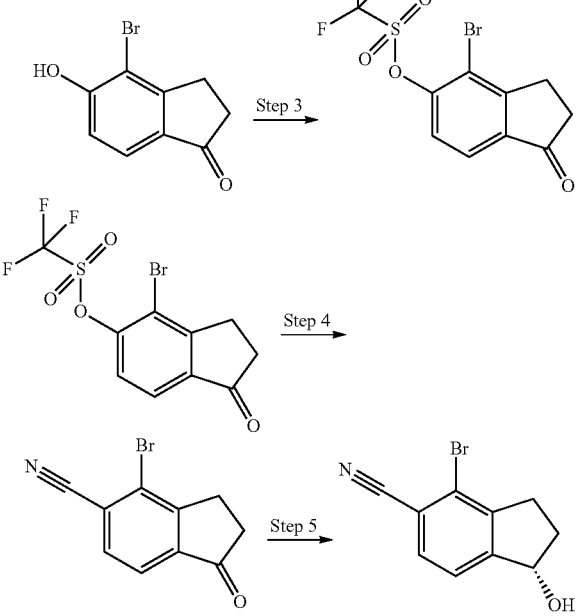

Step 1: 4-Bromo-5-methoxy-indane-1-one

5-Methoxy-indane-1-one (17.2 g, 106.05 mmol) is suspended in 100 mL of water. The flask is covered with an aluminium foil to create a dark environment. N-Bromo-succinimide (18.87 g, 106.05 mmol) is added portionwise and the reaction mixture is stirred at room temperature overnight. The reaction mixture is extracted with 200 mL of ethyl acetate, the organic phase is collected, dried over sodium sulfate and concentrated under vacuum. The crude product obtained (20 g) is used in the next step without any further treatment.

LC (LC METHOD 7): $t_R$=2.70 min; Mass spectrum (ES+): =241 [M+H]$^+$.

Step 2: 4-Bromo-5-hydroxy-indane-1-one

4-Bromo-5-methoxy-indane-1-one (10 g, 41.48 mmol) and sodium methane-thiolate (12.68 g, 180.94 mmol) are dissolved in 25 mL of N,N-dimethylformamide and the reaction mixture is stirred at 120° C. for 3 h. The reaction mixture is concentrated under vacuum, 40 mL of a 2 M solution of hydrochloric acid is added and the reaction mixture is extracted with 300 mL of ethyl acetate. The organic phase is collected, dried over sodium sulfate and concentrated under vacuum. The crude product obtained (9 g) is used in the next step without any further treatment.

LC (LC METHOD 8): $t_R$=9.40 min; Mass spectrum (ES+): m/z=227 [M+H]$^+$.

Step 3 Trifluoro-methanesulfonic acid 4-bromo-1-oxo-indan-5-yl ester

4-Bromo-5-hydroxy-indane-1-one (8 g, 35.23 mmol) and 2,6-lutidine (9.44 g, 88.08 mmol) are dissolved in 10 mL of dichloromethane. The reaction mixture is cooled to 0° C. and trifluoromethane-sulfonic-anhydride (10.93 g, 38.76 mmol) is added dropwise. The reaction mixture is allowed to reach room temperature and stirred for 2 h; it is diluted with 100 mL of dichloromethane and washed with a saturated aqueous ammonium chloride solution. The organic phase is collected, dried over sodium sulfate and concentrated under vacuum. The crude product obtained is purified by flash chromatography (cyclohexane/ethyl acetate 100/0→50/50) to give the title compound (Yield: 10.35 g).

LC (LC METHOD 4): $t_R$=10.92 min; Mass spectrum (EI+): m/z=358.

Step 4 4-Bromo-1-oxo-indan-5-carbonitrile

Trifluoro-methanesulfonic acid 4-bromo-1-oxo-indan-5-yl ester (10.30 g, 28.68 mmol) is stirred in 50 mL of dry N,N-dimethylformamide under argon atmosphere. Zinc cyanide (1.01 g, 8.60 mmol), 1,1-bis(diphenylphosphino) ferrocene (1.58 g, 2.86 mmol) and tris(dibenzylideneacetone) dipalladium(0) (1.32 g, 1.44 mmol) are added the reaction mixture is warmed at 70° C. for 1 h. The reaction mixture is partioned between ethyl acetate and water, the organic phase is washed with brine, washed with water, dried over sodium sulfate and concentrated under vacuum. The crude product obtained is purified by flash chromatography (cyclohexane/ethyl acetate 99/01→50/50) to give the title compound (Yield: 2.2 g).

LC (LC METHOD 4): $t_R$=11.22 min; Mass spectrum (EI+): m/z=235.

Step 5: (S)-4-Bromo-1-hydroxy-indan-5-carbonitrile

The title compound is prepared from 4-bromo-1-oxo-indan-5-carbonitrile (2.2 g, 9.32 mmol) in a manner analogous to that described for Intermediate 6 (Yield: 1.3 g).

LC (GC METHOD 1): $t_R$=11.59 min; Mass spectrum (EI+): m/z=237 [M]+, e.e. 98% by chiral HPLC (Column: Daicel Chiralpak OJ-H, 4.6×250 mm, 5 µm Mobile phase: hexane:ethanol 95:5, 1 ml/min, 25° C.) $t_R$=37.52 (40.84) min.

Intermediate 11

(1S,2S)-2-[4-((R)-4-Bromo-7-fluoro-indan-1-yloxy)-phenyl]-cyclopropanecarboxylic acid ethyl ester

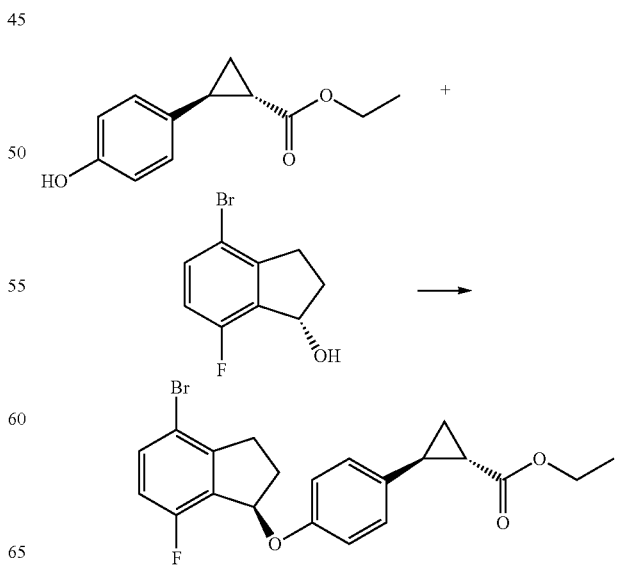

(1S,2S)-2-(4-Hydroxy-phenyl)-cyclopropanecarboxylic acid ethyl ester (Intermediate 4, 6.51 g, 31.57 mmol), (S)-4-Bromo-7-fluoro-indan-1-ol (Intermediate 8, 7.29 g, 31.57 mmol) and triphenyl phosphine (9.11 g, 34.72 mmol) are dissolved in dry tetrahydrofuran (50 mL) and cooled to −20° C. under nitrogen atmosphere. Di-tert-butyl azodicarboxylate (8.00 g, 34.72 mmol) is added and the mixture stirred for 30 minutes at −20° C. then allowed to warm to room temperature and stirred overnight. The solvent is removed under vacuum and the residue purified by flash chromatography (0-10% ethyl acetate in cyclohexane) to give the title compound (Yield 8.23 g).

LC (LC METHOD 4): $t_R$=8.72 min; Mass spectrum (ES+): m/z=460 [M+H+MeCN]$^+$, e.e. 96% by chiral HPLC (Column: Daicel Chiralpak AS-H, 4.6×250 mm, 5 μm Mobile phase: hexane:ethanol 80:20, 1 mL/min, 25° C.) $t_R$=4.96 (4.63) min.

The Intermediates in the following table are prepared in analogy with the procedure used for the preperation of Intermediate 11 from the starting intermediates described:

TABLE 3

| Intermediate | Structure | Name | Starting intermediates | Yield | Analysis |
|---|---|---|---|---|---|
| 12 | 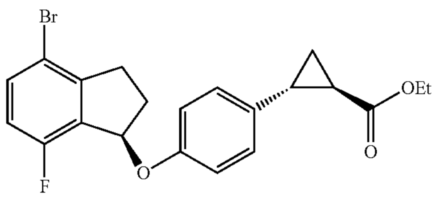 [SMILES: CCOC(=O)[C@@H]1C[C@H]1c1ccc(O[C@@H]2CCc3c(Br)ccc(F)c32)cc1] | (1R,2R)-2-[4-((R)-4-Bromo-7-fluoro-indan-1-yloxy)-phenyl]-cyclopropanecarboxylic acid ethyl ester | Intermediate 5 (2.0 g) and Intermediate 8 (2-24 g) | 2.63 g | LC (LC METHOD 8): $t_R$ = 11.22 min; Mass spectrum (ES+): m/z = 419 [M + H]+, e.e. 100% by chiral HPLC. |
| 13 | 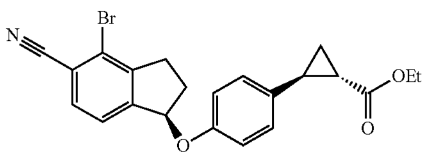 [SMILES: CCOC(=O)[C@H]1C[C@@H]1c1ccc(O[C@@H]2CCc3c2ccc(C#N)c3Br)cc1] | (1S,2S)-2-[4-((R)-4-Bromo-5-cyano-indan-1-yloxy)-phenyl]-cyclopropanecarboxylic acid ethyl ester | Intermediate 4 (490 mg) and Intermediate 10 (566 mg) | 950 mg | LC (LC METHOD 4): $t_R$ = 8.10 min; Mass spectrum (ES+): m/z = 426 [M + H]$^+$. |
| 14 | 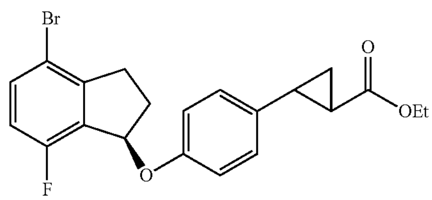 [SMILES: CCOC(=O)C1CC1c1ccc(O[C@@H]2CCc3c(Br)ccc(F)c32)cc1] | 2-[4-((R)-4- Bromo-7-fluoro-indan-1-yloxy)-2-methoxyphenyl]-trans-cyclopropanecarboxylic acid ethyl ester | Intermediate 1 (100 mg) and Intermediate 8 (111 mg) | 127 mg | LC (LC METHOD 7): $t_R$ = 8.59 min; Mass spectrum (ES+): m/z = 419 [M + H]$^+$. |
| 15 | 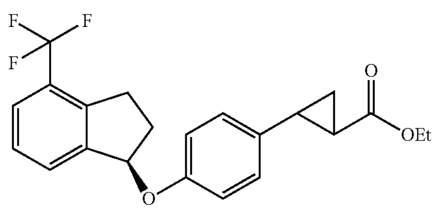 [SMILES: CCOC(=O)C1CC1c1ccc(O[C@@H]2CCc3c2cccc3C(F)(F)F)cc1] | 2-[4-((R)-4-Trifluoromethyl-indan-1-yloxy)-phenyl]-trans-cyclopropanecarboxylic acid ethyl ester | Intermediate 1 (70 mg) and Intermediate 7 (76 mg) | 40 mg | LC (LC METHOD 6): $t_R$ = 10.65 min. |
| 16 | 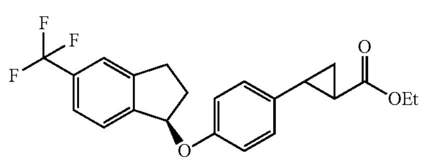 [SMILES: CCOC(=O)C1CC1c1ccc(O[C@@H]2CCc3cc(C(F)(F)F)ccc32)cc1] | 2-[4-((R)-5-Trifluoromethyl-indan-1-yloxy)-phenyl]-trans-cyclopropanecarboxylic acid ethyl ester | Intermediate 1 (100 mg) and Intermediate 9 (97 mg) | 130 mg | LC (LC METHOD 4): $t_R$ = 8.51 min; Mass spectrum (ES+): m/z = 391 [M + H]$^+$. |
| 17 | 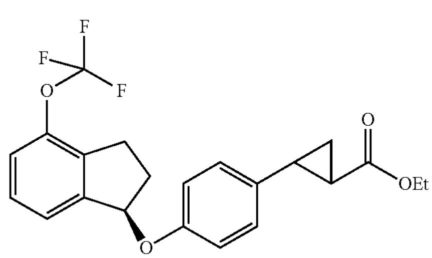 [SMILES: CCOC(=O)C1CC1c1ccc(O[C@@H]2CCc3c(OC(F)(F)F)cccc32)cc1] | 2-(4-((R)-4-Trifluoromethoxy-indan-1-yloxy)-phenyl]-trans-cyclopropanecarboxylic acid ethyl ester | Intermediate 1 (50 mg) and Intermediate 6 (53 mg) | 79 mg | LC (LC METHOD 4): $t_R$ = 8.77 min; Mass spectrum (ES+): m/z = 407 [M + H]$^+$. |

TABLE 3-continued

| Inter-mediate | Structure | Name | Starting intermediates | Yield | Analysis |
|---|---|---|---|---|---|
| 18 | 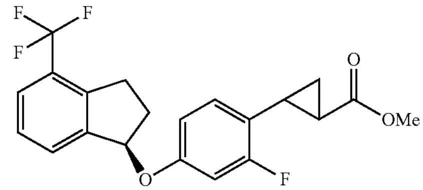 [SMILES: COC(=O)C1CC1c1ccc(O[C@@H]2CCc3c2cccc3C(F)(F)F)cc1F] | 2-[4-((R)-4-Trifluoromethyl-indan-1-yloxy)-2-fluorophenyl]-trans-cyclopropanecarboxylic acid methyl ester | Intermediate 2 (50 mg) and Intermediate 7 (48 mg) | 31 mg | LC (LC METHOD 3): $t_R$ = 1.55 min; Mass spectrum (ES−): m/z = 393 [M − H]⁻. |
| 19 | 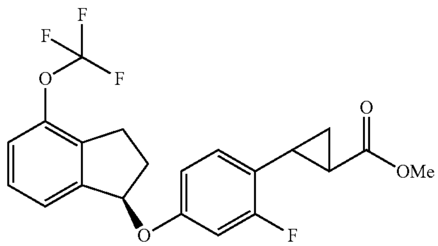 [SMILES: COC(=O)C1CC1c1ccc(O[C@@H]2CCc3c(OC(F)(F)F)cccc32)cc1F] | 2-[4-((R)-4-Trifluoromethoxy-indan-1-yloxy)-2-fluorophenyl]-trans-cyclopropanecarboxylic acid methyl ester | Intermediate 2 (100 mg) and Intermediate 6 (105 mg) | 50 mg | LC (LC METHOD 4): $t_R$ = 8.58 min; Mass spectrum (ES−): m/z = 409 [M − H]⁻. |
| 20 | 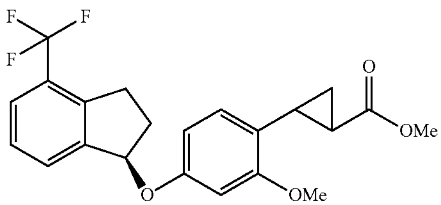 [SMILES: COC(=O)C1CC1c1ccc(O[C@@H]2CCc3c2cccc3C(F)(F)F)cc1OC] | 2-[4-((R)-4-Trifluoromethyl-indan-1-yloxy)-2-methoxyphenyl]-trans-cyclopropanecarboxylic acid methyl ester | Intermediate 3 (80 mg) and Intermediate 7 (73 mg) | 50 mg | LC (LC METHOD 4): $t_R$ = 8.31 min; Mass spectrum (ES+): m/z = 407 [M + H]⁺. |
| 21 | 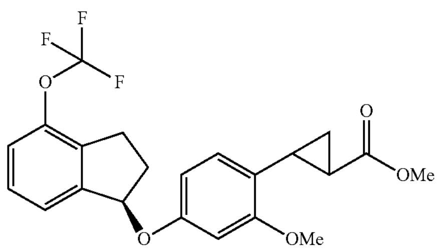 [SMILES: COC(=O)C1CC1c1ccc(O[C@@H]2CCc3c(OC(F)(F)F)cccc32)cc1OC] | 2-[4-((R)-4-Trifluoromethoxy-indan-1-yloxy)-rnethoxyphenyl]-trans-cyclopropanecarboxylic acid methyl ester | Intermediate 3 (80 mg) and Intermediate 6 (79 mg) | 50 mg | LC (LC METHOD 4): $t_R$ = 8.40 min; Mass spectrum (ES+): m/z = 423 [M + H]⁺. |

Intermediates 22 and 23

(1R,2R)-2-[4-((R)-4-Trifluoromethyl-indan-1-yloxy)-phenyl]-cyclopropanecarboxylic acid ethyl ester and (1S,2S)-2-[4-((R)-4-Trifluoromethyl-indan-1-yloxy)-phenyl]-1'-cyclopropanecarboxylic acid ethyl ester

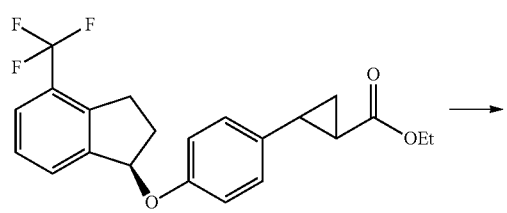

→

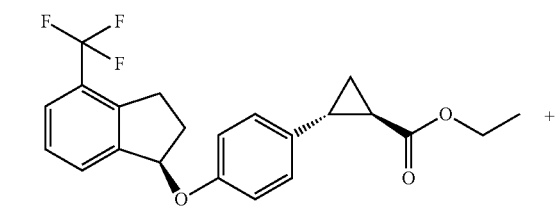

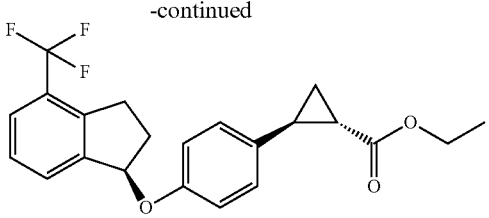

2-[4-((R)-4-Trifluoromethyl-indan-1-yloxy)-phenyl]-trans-cyclopropanecarboxylic acid ethyl ester (Intermediate 15, 498 mg, 1.26 mmol) was separated by semi-preperative chiral HPLC (Column: Daicel Chiralcel OJ-H, 20×250 mm, 5 μm Mobile phase: hexane:ethanol 93:7, 12 ml/min, 25° C.) to give:

Intermediate 22

(1R,2R)-2-[4-((R)-4-Trifluoromethyl-indan-1-yloxy)-phenyl]-1'-cyclopropanecarboxylic acid ethyl ester (Yield 167 mg)

LC (LC METHOD 3): $t_R$=1.58 min; Mass spectrum (ES+): m/z=408 [M+NH4]⁺, e.e. 95% by chiral HPLC (Column:

Daicel Chiralpak OJ-H, 4.6×250 mm, 5 µm Mobile phase: hexane:ethanol 90:10, 1 ml/min, 25° C.) $t_R$=13.65 min. and Intermediate 23

(1S,2S)-2-[4-((R)-4-Trifluoromethyl-indan-1-yloxy)-phenyl]-cyclopropanecarboxylic acid ethyl ester
(Yield 166 mg)

LC (LC METHOD 3): $t_R$=1.58 min; Mass spectrum (ES+): m/z=408 [M+NH4]$^+$, e.e. 95% by chiral HPLC (Column: Daicel Chiralpak OJ-H, 4.6×250 mm, 5 µm Mobile phase: hexane:ethanol 90:10, 1 ml/min, 25° C.) $t_R$=15.35 min.

Intermediate 24

(1S,2S)-2-{4-[(R)-7-Fluoro-4-(4,4,5,5-tetramethyl-[1,3,2]dioxaborolan-2-yl)-indan-1-yloxy]-phenyl}-cyclopropanecarboxylic acid ethyl ester

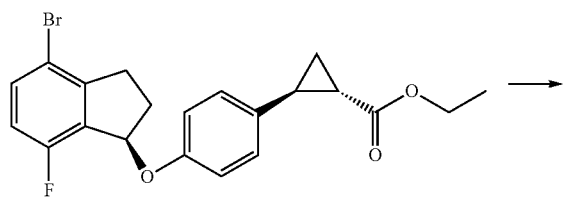

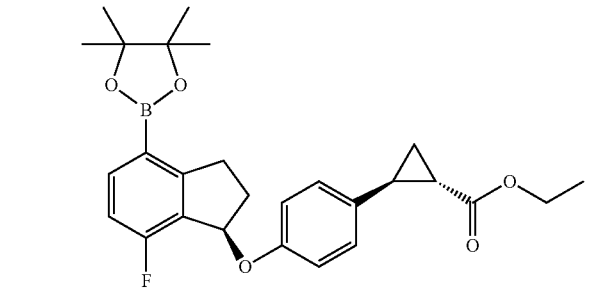

(1S,2S)-2-[4-((R)-4-Bromo-7-fluoro-indan-1-yloxy)-phenyl]-cyclopropanecarboxylic acid ethyl ester (Intermediate 11, 8.23 g, 19.63 mmol), bis(pinacolato)diboron (6.48 g, 25.52 mmol), potassium acetate (5.20 g, 53 mmol) and 1,1'-bis(diphenylphosphino)ferrocenedichloro palladium(II) complex (1.44 g, 1.96 mmol) are combined in dry 1,4-dioxane (100 mL) and degassed with a flow of argon for 10 minutes. The mixture is heated at 100° C. for 8 hours under argon then allowed to cool to room temperature. The solvent is evaporated, the mixture diluted with water and extracted 3 times with dichloromethane. The combined organic phases are washed with water, dried and the solvent removed. The residue is purified by flash chromatography (0-10% EtOAc in cyclohexane) to give the title compound (Yield 5.91 g).

LC (LC METHOD 4): $t_R$=9.31 min; Mass spectrum (ES+): m/z=467 [M+H]$^+$.

Intermediate 25

(1R,2R)-2-{4-[(R)-7-Fluoro-4-(4,4,5,5-tetramethyl-[1,3,2]dioxaborolan-2-yl)-indan-1-yloxy]-phenyl}-cyclopropanecarboxylic acid ethyl ester

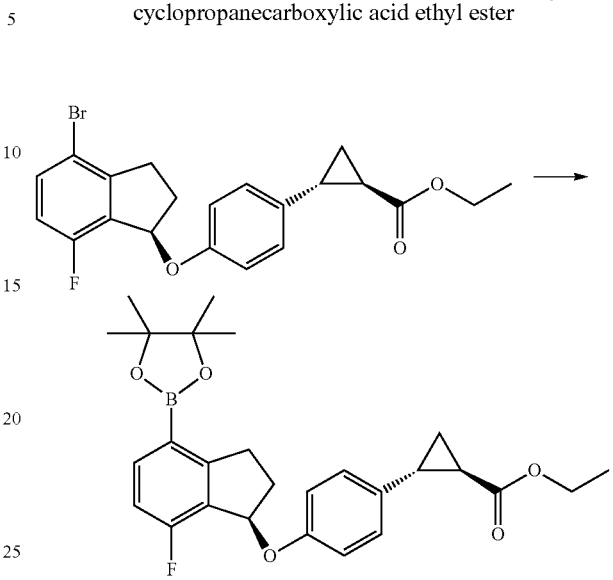

The title compound is prepared from (1R,2R)-2-[4-((R)-4-Bromo-7-fluoro-indan-1-yloxy)-phenyl]-cyclopropanecarboxylic acid ethyl ester (Intermediate 12, 2.60 g, 6.20 mmol) in a manner analogous to that described for Intermediate 24 (Yield 2.35 g).

LC (LC METHOD 4): $t_R$=9.24 min; Mass spectrum (ES+): m/z=467 [M+H]$^+$.

Intermediate 26

2-{-4-[(R)-7-Fluoro-4-(4,4,5,5-tetramethyl-[1,3,2]dioxaborolan-2-yl)-indan-1-yloxy]-phenyl}-trans-cyclopropanecarboxylic acid ethyl ester

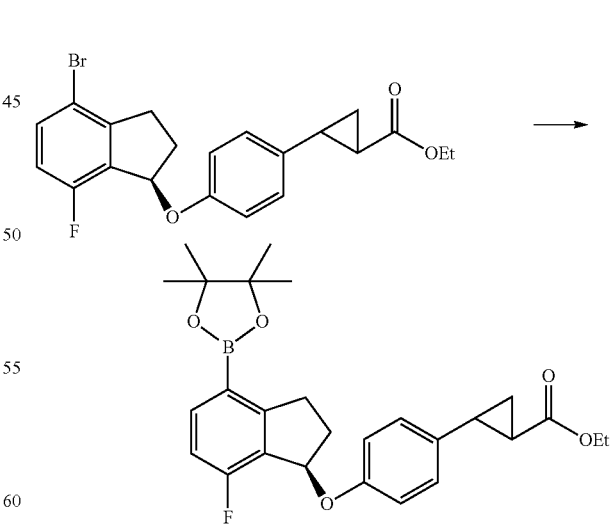

The title compound is prepared from 2-[4-((R)-4-Trifluoromethoxy-indan-1-yloxy)-2-methoxyphenyl]-trans-cyclopropanecarboxylic acid ethyl ester (Intermediate 14, 200 mg, 0.48 mmol) in a manner analogous to that described for Intermediate 24 (Yield 88 mg).

LC (LC METHOD 2): $t_R$=0.98 min; Mass spectrum (ES+): m/z=467 [M+H]$^+$.

Intermediate 27

(1S,2S)-2-[(4-[(R)-5-Cyano-4-(4-hydroxy-2,6-dimethyl-phenyl)-indan-1-yloxy]-phenyl]cyclopropanecarboxylic acid ethyl ester

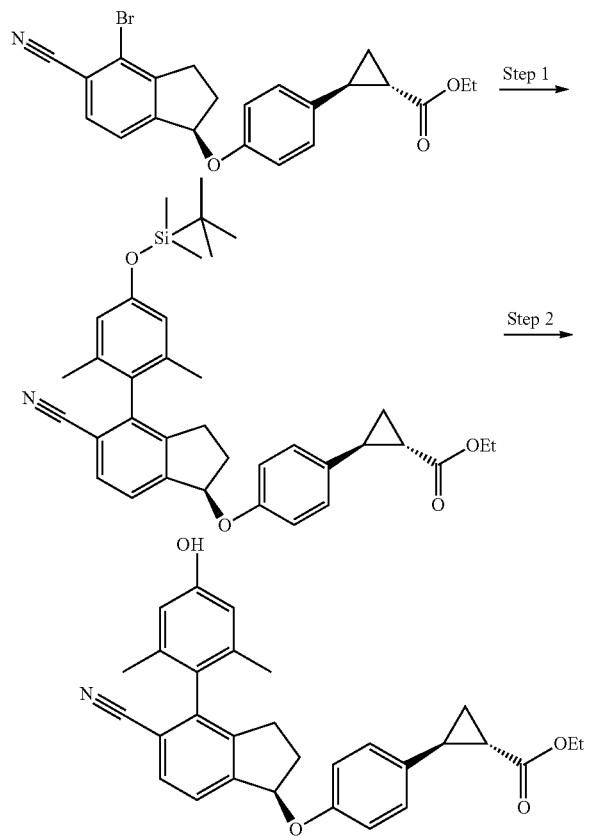

Step 1: (1S,2S)-2-(4-{(R)-4-[4-(tert-Butyl-dimethyl-silanyloxy)-2,6-dimethyl-phenyl]-5-cyano-indan-1-yloxy}-phenyl)-cyclopropanecarboxylic acid ethyl ester Under nitrogen atmosphere, (1S,2S)-2-[4-((R)-4-Bromo-5-cyano-indan-1-yloxy)-phenyl]-cyclopropanecarboxylic acid ethyl ester (Intermediate 13, 590 mg, 1.38 mmol), (4-{[tert-butyl(dimethyl)silyl]oxy}-2,6-dimethylphenyl)boronic acid (0.78 g, 2.77 mmol, WO2005/63729A1), 2-dicyclohexylphosphino-2'-(N,N-dimethylamino)biphenyl (54 mg, 0.138 mmol), tris(dibenzylideneacetone)dipalladium(0) (63.37 mg, 0.07 mmol) and sodium carbonate (500 mg, 4.71 mmol) are suspended in 10 mL of toluene and 5 mL of water. The reaction mixture is stirred at 110° C. for 12 h then it is concentrated under vacuum. The crude product obtained is purified by flash chromatography (cyclohexane/ethyl acetate 100/01 4 80/20) to give the title compound (Yield: 500 mg).

Step 2: (1S,2S)-2-{4-[(R)-5-Cyano-4-(4-hydroxy-2,6-dimethyl-phenyl)-indan-1-yloxy]-phenyl}cyclopropanecarboxylic acid ethyl ester (1S,2S)-2-(4-{(R)-4-[4-(tert-Butyl-dimethyl-silanyloxy)-2,6-dimethyl-phenyl]-5-cyano-indan-1-yloxy}-phenyl)-cyclopropanecarboxylic acid ethyl ester (500 mg, 0.86 mmol) is dissolved in 10 mL of tetrahydrofuran, a 1 M aqueous solution of tetrabutylammonium fluoride (2 mL, 2.00 mmol) is added and the reaction mixture is stirred at room temperature for 3 h. 2 mL of an ammonium chloride saturated aqueous solution is added and the reaction mixture is concentrated under vacuum. The crude product obtained is purified by flash chromatography (cyclohexane/ethyl acetate 100/01→50/50) to give the title compound (Yield: 310 mg).

LC (LC METHOD 7): $t_R$=3.98 min; Mass spectrum (ES+): m/z=468 [M+H]$^+$.

Intermediate 28

2-Bromo-5-(3-methanesulfonyl-propoxy)-1,3-dimethyl-benzene

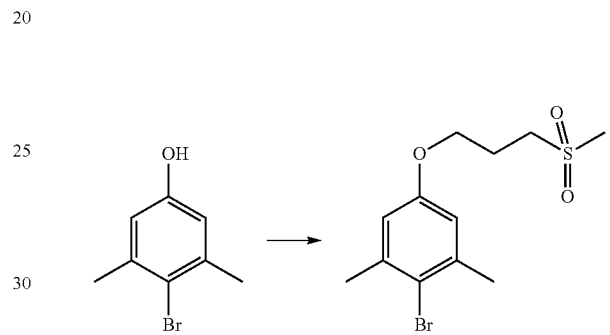

4-Bromo-3,5-dimethylphenol (5.0 g, 24.62 mmol), 3-methylthiopropanol (2.54 mL, 24.62 mmol), di-tert-butyl azodicarboxylate (6.24 g, 27.08 mmol) and triphenylphosphine (7.10 g, 27.08 mmol) are dissolved in dichloromethane (30 mL) and stirred for 3 hours. 3-chloroperoxybenzoic acid (12.75 g, 73.86 mmol) is added and the mixture stirred overnight. The reaction mixture is washed with saturated aqueous sodium carbonate solution, the organic phase dried and the solvent removed under vacuum. The residue is purified by flash chromatography (0-50% ethyl acetate in cyclohexane followed by 1% methanol in dichloromethane) to give the title compound (Yield 3.82 g).

LC (LC METHOD 4): $t_R$=6.68 min; Mass spectrum (ES+): m/z=321 [M+H]$^+$.

Intermediate 29

2-Bromo-5-(2-methanesulfonyl-2-methyl-propoxy)-1,3-dimethyl-benzene

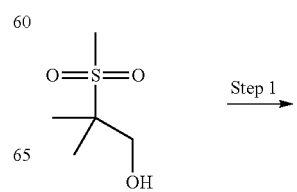

-continued

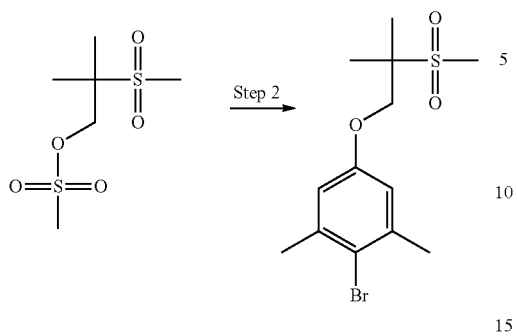

Step 1: Methanesulfonic acid 2-methanesulfonyl-2-methyl-propyl ester

The title compound is prepared from 2-Methanesulfonyl-2-methyl-propan-1-ol (Bulletin de la Societe Chimique de France, 1980, vol. 2, #9-10 p. 441-443) following a similar procedure as reported in: Journal of Medicinal Chemistry, 1995, vol. 38, #11 p. 2009-2017.

Step 2: 2-Bromo-5-(2-methanesulfonyl-2-methyl-propoxy)-1,3-dimethyl-benzene

4-Bromo-3,5-dimethylphenol (1.3 g, 6.51 mmol) and NaH (60% on mineral oil: 167 mg, 4.17 mmol) are stirred in 8 mL of N,N-dimethylformamide for 30 min in a microwave vial, methanesulfonic acid 2-methanesulfonyl-2-methyl-propyl ester (600 mg, 2.61 mmol) is added and the reaction mixture is heated in a microwave oven at 160° C. for 2 h. The solvent is removed under vacuum and the crude product is purified by flash chromatography (cyclohexane/ethyl acetate 99/01→90/10) to give the title compound (Yield: 250 mg).

Intermediate 30

4-Bromo-N-(2-hydroxy-2-methyl-propyl)-3,5-dimethyl-benzamide

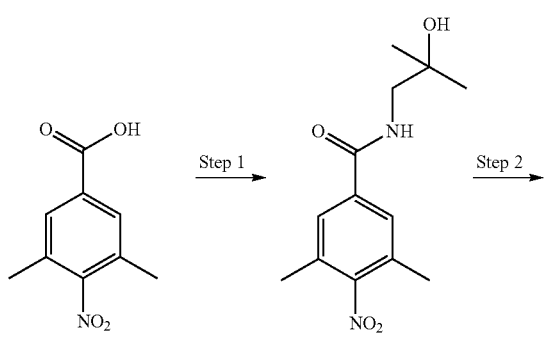

-continued

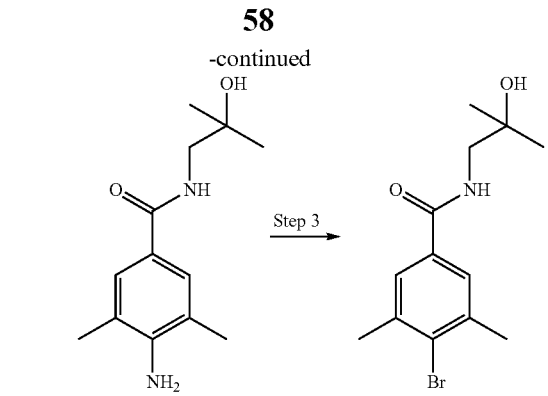

Step 1. 4-Nitro-N-(2-hydroxy-2-methyl-propyl)-3,5-dimethyl-benzamide 3,5-Dimethyl-4-nitrobenzoic acid (1 g, 5.12 mmol) is suspended in dry tetrahydrofuran (10 mL) and 1,1'-carbonyldiimidazole (0.91 g, 5.64 mmol) is added. The mixture is stirred for 3 hours then 1-amino-2-methyl-propan-2-ol (patent WO2010/84767, 1 g, 11.22 mmol) is added and the mixture stirred for 30 minutes. The solvent is removed, the residue suspended in EtOAc and washed with 0.2 M aqueous HCl solution, saturated sodium bicarbonate solution and brine, dried and the solvent removed under vacuum to give the title compound (Yield 1.2 g).

LC (LC METHOD 2): $t_R$=0.92 min; Mass spectrum (ES+): m/z=267 [M+H]$^+$.

Step 2. 4-amino-N-(2-hydroxy-2-methyl-propyl)-3,5-dimethyl-benzamide

4-Nitro-N-(2-hydroxy-2-methyl-propyl)-3,5-dimethyl-benzamide (1.2 g, 4.51 mmol) is suspended in methanol (10 mL) and hydrogenated at 3 bar for 3 hours using 10% palladium on activated carbon (120 mg) as the catalyst. The mixture is filtered through celite and the solvent removed under vacuum to give the title compound (Yield 900 mg).

LC (LC METHOD 2): $t_R$=0.61 min; Mass spectrum (ESI+): m/z=237 [M+H]$^+$.

Step 3. 4-Bromo-N-(2-hydroxy-2-methyl-propyl)-3,5-dimethyl-benzamide tert-Butyl nitrate (1.26 mL, 9.52 mmol) and copper(II) bromide (1.02 g, 4.57 mmol) are suspended in acetonitrile (6 mL) and heated to 65° C. for 10 minutes. 4-Amino-N-(2-hydroxy-2-methyl-propyl)-3,5-dimethyl-benzamide (900 mg, 3.81 mmol) in acetonitrile (6 mL) is added and the mixture heated at reflux for 4 hours. 0.2 M aqueous hydrochloric acid is added and the mixture extracted with diethyl ether. The organic phase is dried and the solvent removed under vacuum. The residue is purified by flash chromatography (0-50% ethyl acetate in cyclohexane) to give the title compound. (Yield 460 mg).

LC (LC METHOD 4): $t_R$=5.62 min; Mass spectrum (ES+): m/z=300/302 [M+H]$^+$.

Intermediate 31

4-(4-Bromo-3,5-dimethyl-phenoxy)-2-methyl-butan-2-ol

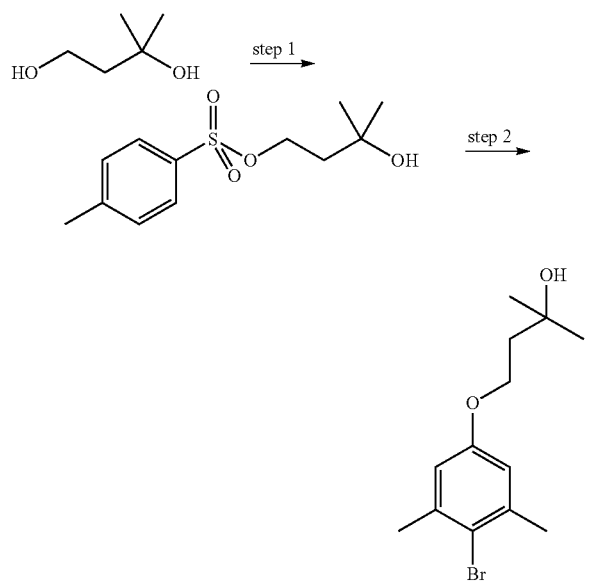

Step 1. Toluene-4-sulfonic acid 3-hydroxy-3-methyl-butyl ester

3-Methyl-1,3-butanediol (1.5 mL, 14.06 mmol) is suspended in dry dichloromethane (5 mL) and pyridine (1.24 mL, 15.46 mmol) is added followed by 4-toluenesulfonyl chloride (2.68 g, 14.06 mmol). The mixture is stirred overnight then washed with 1M aqueous hydrochloric acid, dried and the solvent removed under vacuum. The residue is purified by flash chromatography (0-30% ethyl acetate in cyclohexane) to give the title compound. (Yield 970 mg).

LC (LC METHOD 4): $t_R$=5.67 min; Mass spectrum (ES+): m/z=258 [M+H]$^+$.

Step 2. 4-(4-Bromo-3,5-dimethyl-phenoxy)-2-methyl-butan-2-ol

Toluene-4-sulfonic acid 3-hydroxy-3-methyl-butyl ester (970 mg, 3.75 mmol), 4-bromo-3-5-dimethylphenol (2.0 g, 9.95 mmol) and potassium carbonate (1.51 g, 10.94 mmol) are suspended in dry N,N-dimethylformamide (10 mL) and stirred at 80° C. for 4 hours then overnight at room temperature. The mixture is diluted with water and extracted with diethyl ether. The organic extracts are washed with 1 M aqueous NaOH solution, dried and the solvent removed under vacuum to give the title compound (Yield 1.0 mg).

GC (GC METHOD 1): $t_R$=11.61 min; Mass spectrum (EI+): m/z=286 [M]$^+$.

Intermediate 32

2-Bromo-5-(1-methanesulfonyl-cyclopropyl-methoxy)-1,3-dimethyl-benzene

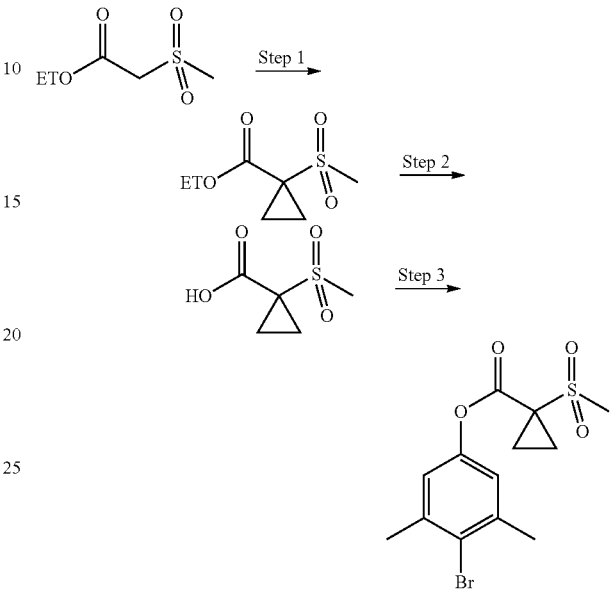

Step 1. 1-Methanesulfonyl-cyclopropanecarboxylic acid ethyl ester

Ethylmethanosulfonylacetate (1 g, 6.02 mmol) is suspended in N,N-dimethylformamide (50 mL) and potassium carbonate (11.84 g, 85.7 mmol) and 1,2-dibromoethane (7.25 mL, 84.1 mmol) is added. The mixture is stirred at 80° C. for 6 hours followed by 3 days at room temperature. The mixture is diluted with water and extracted with dichloromethane. The organic phase is dried and the solvent removed under vacuum. The residue is purified by flash chromatography (dichloromethane) to give the title compound (Yield 1.03 g).

GC (GC METHOD 1): $t_R$=6.64 min; Mass spectrum (EI+): m/z=192 [M]$^+$.

Step 2. (1-Methanesulfonyl-cyclopropyl)-methanol

1-Methanesulfonyl-cyclopropanecarboxylic acid ethyl ester (1 g, 5.2 mmol) is dissolved in dry tetrahydrofuran (20 mL) and cooled to 0° C. Lithium aluminium hydride (237 mg, 6.24 mmol) is added, the mixture allowed to warm to room temperature and stirred overnight. The mixture is cooled to 0° C. and saturated aqueous sodium sulfate solution is added with stirring. The precipitated solids are removed by filtration and the filtrate is partitioned between ethyl acetate and water. The organic phase is dried and the solvent removed under vacuum. The residue is purified by flash chromatography (ethyl acetate) to give the title compound (Yield 317 mg).

GC (GC METHOD 1): $t_R$=7.97 min; Mass spectrum (EI+): m/z=133 [M−OH]$^+$.

Step 3. 2-Bromo-5-(1-methanesulfonyl-cyclopropyl-methoxy)-1,3-dimethyl-benzene 4-bromo-3,5-dimethylphenol, (306 mg, 1.52 mmol), (1-Methanesulfonyl-cyclopropyl)-methanol (228 mg, 1.52 mmol), and triphenylphosphine (399 mg, 1.52 mmol) are suspended in dry tetrahydrofuran (10 mL) and cooled to 0° C. Di-tert-butylazodicarboxylate (350 mg, 1.52 mmol) is added and the mixture stirred at 50° C. for 48 hours then at room temperature for a further 48 hours. The mixture is concentrated under vacuum then partitioned between water and dichloromethane, The organic phase is dried and the solvent removed under vacuum. The residue is purified by flash chromatography (0-20% ethyl acetate in cyclohexane) to give the title compound as a crude material which was used without further purification (Yield 664 mg).

GC (GC METHOD 1): $t_R$=13.16 min; Mass spectrum (EI+): m/z=332 [M]$^+$.

Intermediate 33

4-Iodo-3,5,N-trimethyl-benzamide

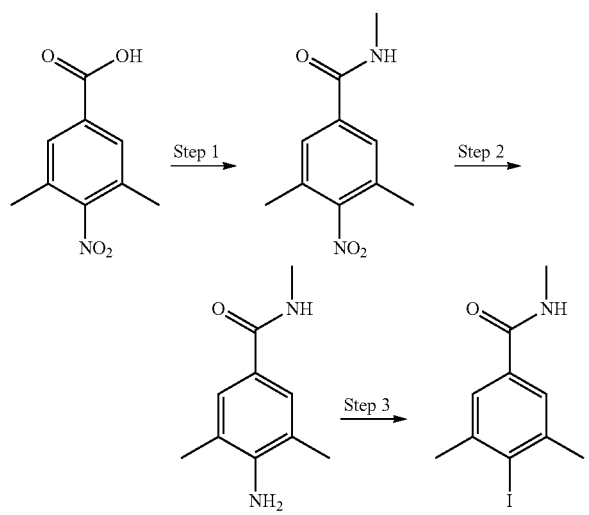

Step 1. 4-Nitro-3,5,N-trimethyl-benzamide 3,5-Dimethyl-4-nitrobenzoic acid (1 g, 5.12 mmol) is suspended in dry tetrahydrofuran (10 mL) and 1,1'-carbonyldiimidazole (0.91 g, 5.64 mmol) is added. The mixture is stirred for 3 hours then methylamine (2 M solution in tetrahydrofuran, 7.7 mL, 15.4 mmol) is added and the mixture stirred for 30 minutes. The solvent is removed, the residue suspended in EtOAc and washed with 0.2 M aqueous HCl solution, saturated sodium bicarbonate solution and brine, dried and the solvent removed under vacuum to give the title compound (Yield 1.0 g).

LC (LC METHOD 4): $t_R$=4.82 min; Mass spectrum (ES+): m/z=209 [M+H]$^+$.

Step 2. 4-Amino-3,5,N-trimethyl-benzamide

4-Nitro-3,5,N-trimethyl-benzamide (1.0 g, 4.8 mmol) is suspended in methanol (10 mL) and hydrogenated at 3 bar for 3 hours using 10% Palladium on activated carbon (100 mg) as the catalyst. The mixture is filtered through celite and the solvent removed under vacuum to give the title compound (Yield 850 mg).

LC (LC METHOD 8): $t_R$=6.02 min; Mass spectrum (ESI+): m/z=179 [M+H]$^+$.

Step 3. 4-Iodo-3,5,N-trimethyl-benzamide

4-Amino-3,5,N-trimethyl-benzamide (850 mg, 4.77 mmol) is suspended in hydrochloric acid (37%, 2 mL), stirred until completely dissolved then cooled to 0° C. Sodium nitrite (494 mg, 7.15 mmol) in water (0.5 mL) is added and the mixture stirred for 1 hour at 0° C. Potassium iodide (2.38 g, 14.31 mmol) in 1.5 mL water is added and the mixture stirred for 15 minutes. The mixture is diluted with dichloromethane then washed with 10% aqueous sodium thosulfate solution, dried and the solvent removed under vacuum. The residue is purified by flash chromatography (0-50% ethyl acetate in cyclohexane) to give the title compound. (Yield 850 mg).

LC (LC METHOD 4): $t_R$=5.88 min; Mass spectrum (ES+): m/z=290 [M+H]$^+$.

Intermediate 34

3-(4-Bromo-3,5-dimethyl-phenoxymethyl)-1-methanesulfonyl-azetidine

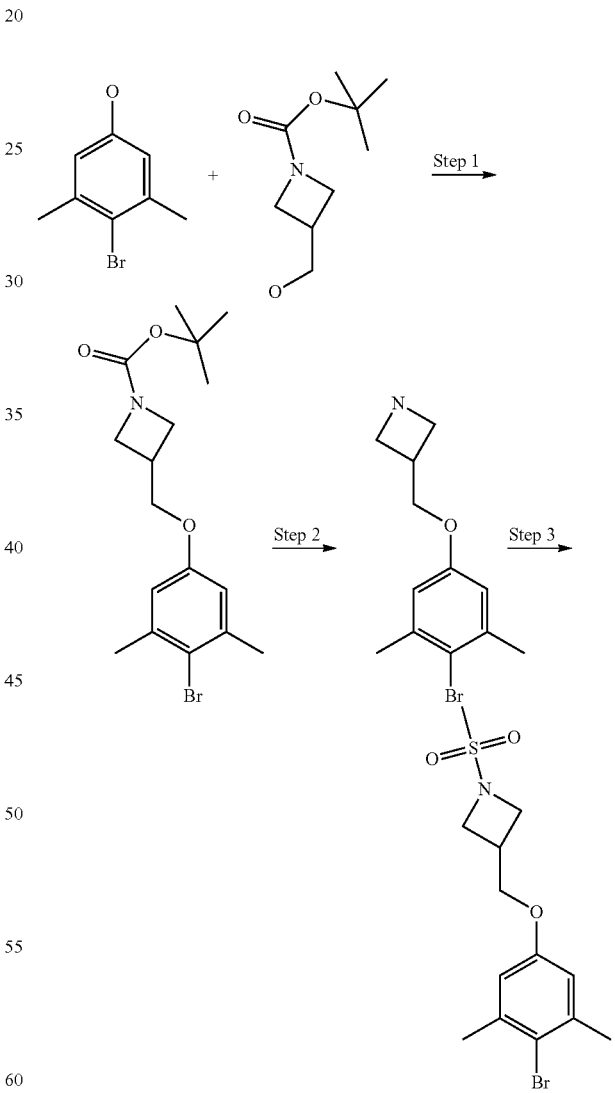

Step 1: 3-(4-Bromo-3,5-dimethyl-phenoxymethyl)-azetidine-1-carboxylic acid tert-butyl ester 4-Bromo-3,5-dimethylphenol (3.7 g, 18.16 mmol), 3-hydroxymethylazetidine-1-carboxylic acid tert-butyl ester (commercially available, EP1889836 A1, 3.40 g, 18.16 mmol), di-tert-butylazodicarboxylate (4.6 g, 19.97 mmol) and triphenylphosphine (5.24 g, 19.97 mmol) are suspended in dichloromethane (100 mL) and stirred for 2 hours at room temperature. The solvent is removed under vacuum and the residue suspended in diethyl ether, cooled and the precipitate is filtered off. The solvent is removed under vacuum to give the title compound (Yield: 5.0 g).

LC (LC METHOD 1): $t_R$=1.64 min; Mass spectrum (ES+): m/z=372 [M+H]+.

Step 2: 3-(4-Bromo-3,5-dimethyl-phenoxymethyl)-azetidine 3-(4-Bromo-3,5-dimethyl-phenoxymethyl)-azetidine-1-carboxylic acid tert-butyl ester (3.9 g, 6.32 mmol) is dissolved in 30 mL of dichloromethane and stirred at 0° C. Trifluoroacetic acid (1.45 g, 12.64 mmol) is added and the reaction mixture is stirred at 0° C. for 6 h. 15 mL of saturated aqueous NaHCO₃ is added, the organic phase is separated, dried over sodium sulfate and concentrated under vacuum to give the title compound (Yield: 1.30 g).

LC (LC METHOD 1): $t_R$=0.93 min; Mass spectrum (ES+): m/z=272 [M+H]+.

Step 3: 3-(4-Bromo-3,5-dimethyl-phenoxymethyl)-1-methanesulfonyl-azetidine 3-(4-Bromo-3,5-dimethyl-phenoxymethyl)-azetidine (400 mg, 1.48 mmol) and DIPEA (0.48 g, 3.7 mmol) are dissolved in 20 mL of dichloromethane and stirred at 0° C. Methanesulfonylchloride (0.12 mL, 1.48 mmol) is added and the reaction mixture is stirred at 0° C. for 2 h. The reaction mixture is washed with water, the organich phase is separated, dried over sodium sulfate and concentrated under vacuum. The crude product is purified by flash chromatography 0-50% ethyl acetate in cyclohexane) to give the title compound (Yield: 330 mg).

Intermediate 35

4-(4-Bromo-3,5-dimethyl-phenoxymethyl)-tetrahydro-thiopyran 1,1-dioxide

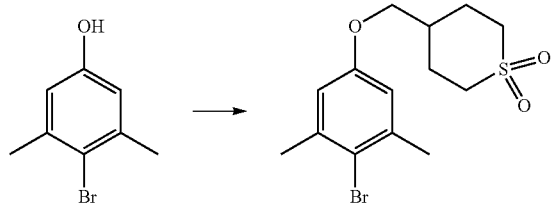

The title compound is prepared in analogy to intermediate 34 step 1, starting from 4-bromo-3,5-dimethylphenol (430 mg, 2.13 mmol) and 1,1-Dioxo-hexahydro-1-thiopyran-4-yl)-methanol (350 mg, 2.13 mmol). (Yield: 400 mg)

Intermediate 36

2-[2-(4-Bromo-3,5-dimethyl-phenoxy)-ethyl]-isothiazolidine 1,1-dioxide

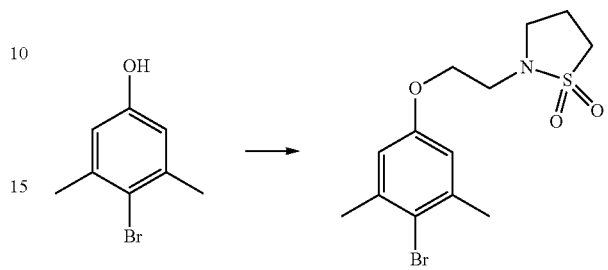

4-Bromo-3,5-dimethylphenol (1.25 g, 6.17 mmol) and sodium hydride (60% on mineral oil, 160 mg, 3.95 mmol) are suspended in dry N,N-dimethylacetate (25 mL) and stirred for 30 minutes at room temperature. Methanesulfonic acid 2-(1,1-dioxo-isothiazolidin-2-yl)-ethyl ester (Patent EP1479684 A1, 600 mg, 2.47 mmol;) is added and the mixture stirred at 80° C. for 5 hours. The mixture is concentrated under vacuum, diluted with water and extracted with ethyl acetate. The organic phase is dried and the solvent removed. The residue is purified by flash chromatography (0-50% ethyl acetate in cyclohexane) to give the title compound. (Yield: 350 mg).

Intermediate 37

(R)-3-(4-Bromo-3,5-dimethyl-phenoxy)-1-methanesulfonyl-pyrrolidine

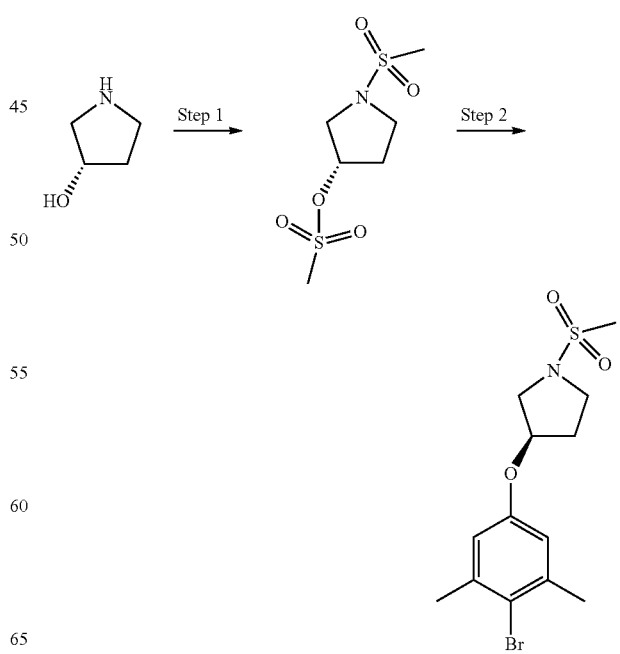

Step 1: Methanesulfonic acid (S)-1-methanesulfonyl-pyrrolidin-3-yl ester (S)-3-Hydroxypyrrolidine (2 g, 23 mmol) is dissolved in 40 mL of tetrahydrofuran. DIPEA (10 mL, 57.36 mmol) is added and the reaction mixture is stirred for 30 min at room temperature. The reaction mixture is cooled to 0° C., methanesulfonyl chloride (3.73 mL, 48.21 mmol) is added dropwise and the reaction mixture is allowed to reach room temperature. After stirring for 2 h, the reaction mixture is concentrated under vacuum, water is added and the reaction mixture is extracted with ethyl acetate. The organic phase is collected, dried over sodium sulfate, separated and concentrated under vacuum. The crude product obtained is triturated with a solution of cyclohexane/dichloromethane 1:1 to give the title compound. (Yield: 2.2 g).

Step 2: (R)-3-(4-Bromo-3,5-dimethyl-phenoxy)-1-methanesulfonyl-pyrrolidine

The title compound is prepared in analogy to Intermediate 36 from 4-Bromo-3,5-dimethylphenol (626 mg, 3.08 mmol) and Methanesulfonic acid (S)-1-methanesulfonyl-pyrrolidin-3-yl ester (300 mg, 1.23 mmol). (Yield: 350 mg).

Intermediate 38

(S)-3-(4-Bromo-3,5-dimethyl-phenoxy)-1-methanesulfonyl-pyrrolidine

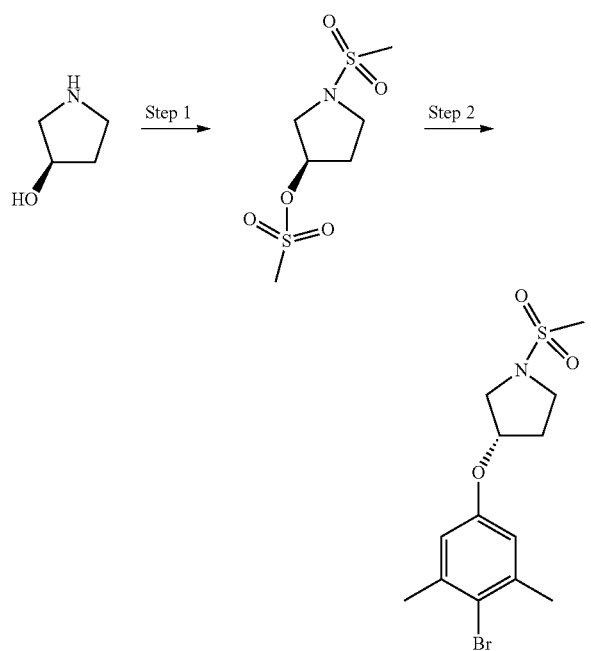

The title compound is prepared in analogy to Intermediate 37 from (S)-3-hydroxypyrrolidine. (Yield: 134 mg).

LC (LC METHOD 4): $t_R$=7.32 min; Mass spectrum (ES+): m/z=348 [M+H]$^+$.

Intermediate 39

(R)-3-(4-Bromo-3,5-dimethyl-phenoxy)-tetrahydrofuran

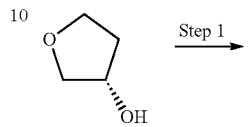

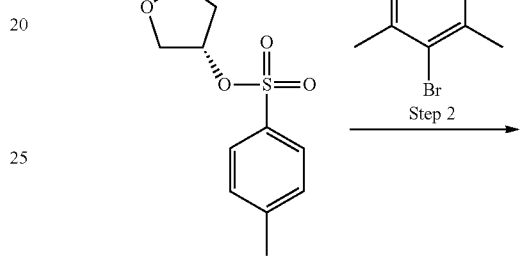

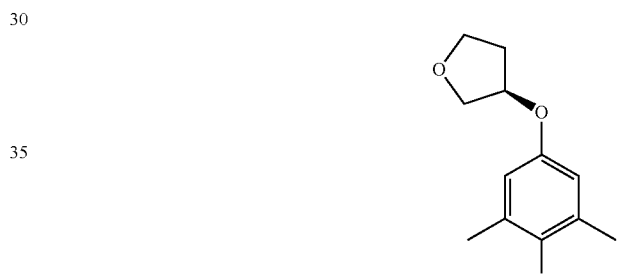

Step 1:

(S)-(+)-3-Hydroxytetrahydrofuran (5.0 g) in dichloromethane (50 mL) is allowed to react in the presence of pyridine (12 mL) and 4-dimethylaminopyridine (0.35 g) with 4-toluenesulfonyl chloride (14.5 g) for 16 h. The mixture is washed with water, dried and the solvent evaporated under vacuum. Purification of the residue by column chromatography (silica gel, dichloromethane:MeOH 100:0 to 90:10 gradient) gives the desired compound (3.7 g).

LC (LC METHOD 2): $t_R$=0.49 min; Mass spectrum (ES+): m/z=260 [M+NH$_4$]$^+$.

Step 2:

4-Bromo-3,5-dimethylphenol (2.0 g), the product from Step 1 (2.7 g) and K$_2$CO$_3$ (1.5 g) in N,N-dimethylformamide (10 mL) are stirred at 80° C. for 16 h. After cooling the mixture is partitioned between water and EtOAc, the organic layer washed twice with water and then with brine, dried (MgSO$_4$) and concentrated. Purification of the residue by column chromatography (silica gel, dichloromethane:MeOH 98:2) gives the desired compound (2.8 g, content ca. 90%).

LC (LC METHOD 2): $t_R$=0.68 min; Mass spectrum (ES+): m/z=288/290 [M+NH$_4$]$^+$.

Intermediate 40

2-(4-Bromo-3,5-dimethyl-phenoxy)-2-methyl-propan-1-ol

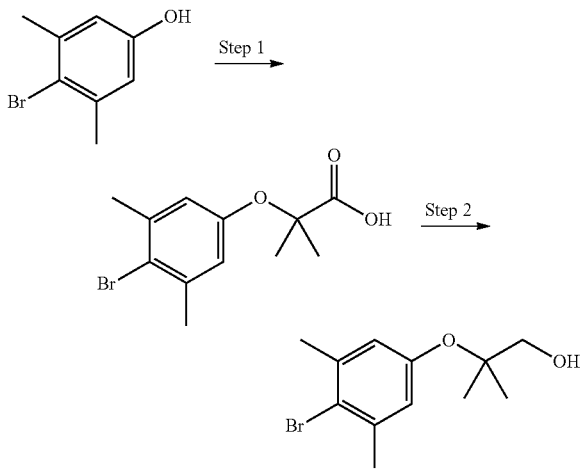

Step 1:
NaH (32% content, 31 g) is added in portions to 4-bromo-3,5-dimethylphenol (5.0 g) in acetone (100 mL), keeping the temperature below 28° C. HCCl$_3$ is added dropwise, keeping the temperature below 35° C. The mixture is stirred at that temperature for 30 min, then heated at reflux for 3 hours. Volatiles are evaporated in vacuo, the residue diluted with water, cooled in an ice bath, acidified with HCl (6 M) and extracted with AcOEt. The organic phase is dried, the solvent evaporated in vacuo and the residue purified by column chromatography (silica gel, cyclohexane:ethyl acetate 50:50) to obtain the desired material (8.9 g of ca. 80% content).

LC (LC METHOD 1): t$_R$=0.92 min.

Step 2:
The material obtained in Step 1 (4.5 g) is dissolved in dry tetrahydrofuran (50 mL) and H$_3$B.SMe$_2$ (2.6 mL) is added under N$_2$. After 5 hours at room temperature the mixture is cooled at 0° C. and HCl (10% aqueous) is added slowly. The mixture is extracted with CH$_2$Cl$_2$, the organic layer collected, dried and the solvent evaporated in vacuo. The residue is purified by column chromatography (silica gel, n-hexane/ethyl acetate 100:0 to 50:50) to obtain the desired product (2.6 g).

LC (LC METHOD 1): t$_R$=1.28 min.

Intermediate 41

1-(4-Bromo-3,5-dimethyl-phenoxy)-2-methyl-propan-2-ol

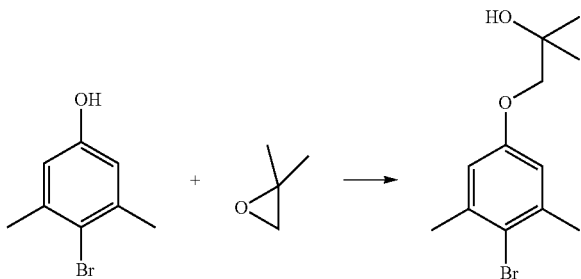

4-Bromo-3,5-dimethylphenol (4.0 g), isobutylene oxide (2.0 g) and Cs$_2$CO$_3$ (9.7 g) in N,N-dimethylformamide (10 mL) are stirred at 100° C. for 20 h. After cooling the mixture is partitioned between water and EtOAc, the organic layer dried (MgSO$_4$) and concentrated. Purification of the residue by column chromatography (silica gel, n-hexane:EtOAc 100:0 to 50:50 gradient) gives the desired compound (5.6 g, content ca. 97%).

LC (LC METHOD 1): t$_R$=1.31 min; Mass spectrum (ES+): m/z=290/2 [M+NH$_4$]$^+$.

Intermediate 42

2-Bromo-5-((S)-3-methanesulfonyl-2-methyl-propoxy)-1,3-dimethyl-benzene

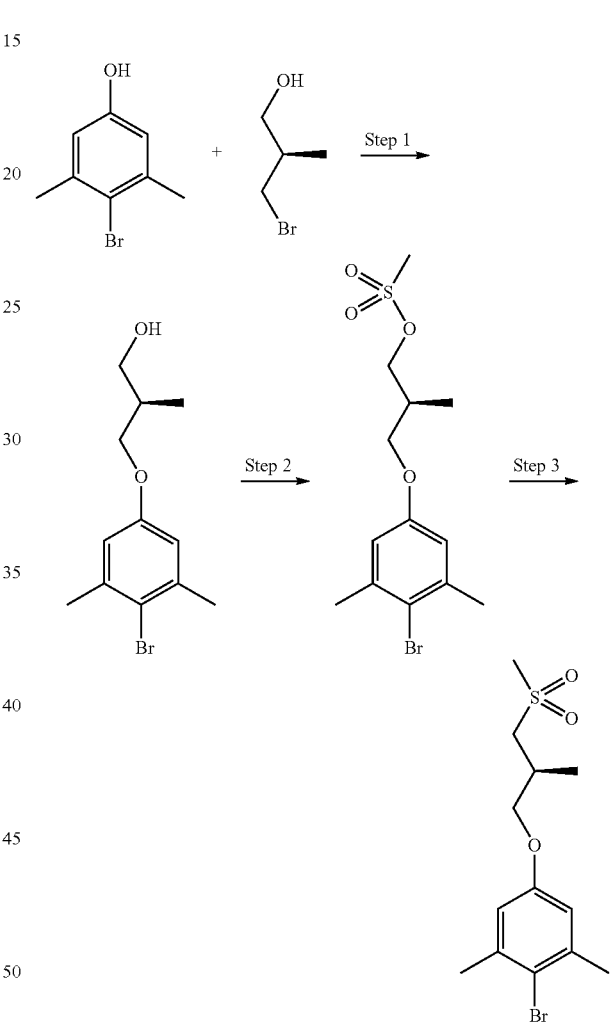

Step 1:
4-Bromo-3,5-dimethylphenol (2.6 g), (R)-(−)-3-bromo-2-methyl-1-propanol (4.0 g) and K$_2$CO$_3$ (9.0 g) in acetonitrile (50 mL) are stirred in a closed vessel at 80° C. for 4 h. After cooling the mixture is partitioned between water and Et$_2$O, the organic layer washed with brine, dried (Na$_2$SO$_4$) and concentrated to give the desired compound (3.6 g, content ca. 95%) that was used as such in the next step.

LC (LC Method 5): t$_R$=7.965 min; Chiral HPLC (Column: Daicel Chiralpak AD-H, 4.6×250 mm, 5 μm Mobile phase: Hexane:isopropanol 85:15, 1 mL/min, 25° C.): t$_R$=4.602 min

Step 2:
The product from Step 1 (3.6 g) and methanesulfonyl chloride (1.9 mL) in CH$_2$Cl$_2$ (30 mL) and triethylamine (7.0 mL)

are stirred for 16 h. The mixture is partitioned between saturated aqueous citric acid and EtOAc, the organic layer washed twice with water and then with brine, dried (MgSO$_4$) and CH$_2$Cl$_2$, the organic layer washed with brine, dried (Na$_2$SO$_4$) and concentrated to give the desired compound (4.5 g, content ca. 95%) that was used as such in the next step.

LC (LC Method 5): t$_R$=8.728 min;

Step 3:

The product from Step 2 (4.5 g) and sodium methanesulfinate (6.1 g) in N,N-dimethylformamide (30 mL) are heated at 80° C. with vigorous stirring for 4 h. After cooling the mixture is partitioned between water and Et$_2$O, the organic layer washed with brine, dried (Na$_2$SO$_4$), concentrated under reduced pressure and submitted to column chromatography (silica gel, n-hexane:EtOAc 100:0 to 55:45 gradient) to give the desired compound (1.9 g).

LC (GC METHOD 1): t$_R$=13.32 min; Mass spectrum: m/z=334/6 [M]$^+$.

Intermediate 43

2-Bromo-5-((S)-3-methanesulfonyl-2-methyl-propoxy)-1,3-dimethyl-benzene

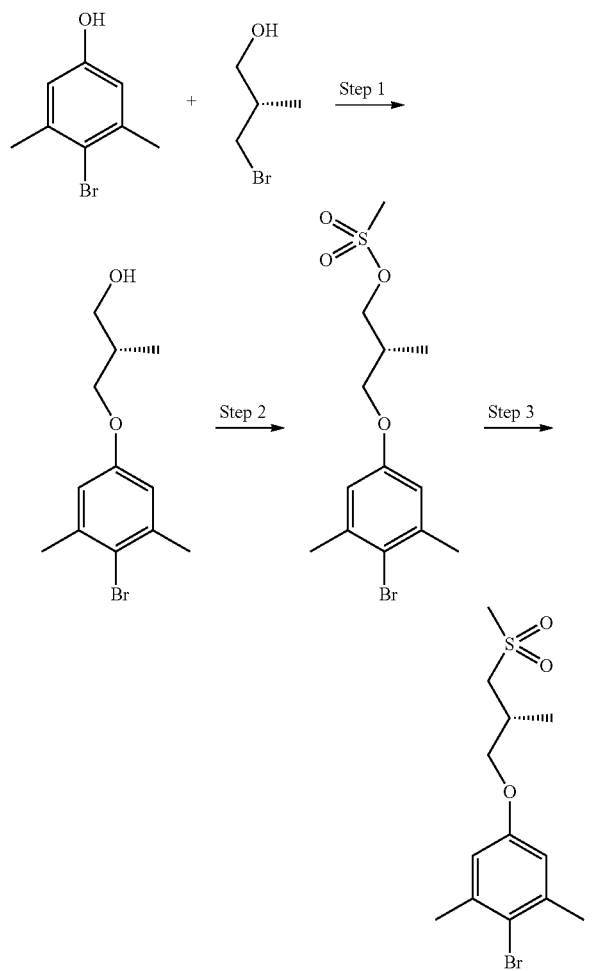

The title compound is prepared in a manner analogous to that described for Intermediate 42, using (S)-(+)-3-bromo-2-methyl-1-propanol instead of (R)-(−)-3-bromo-2-methyl-1-propanol (Yield 4.0 g). The product from Step 1 shows LC (Column: Daicel Chiralpak AD-H, 4.6×250 mm, 5 μm Mobile phase: Hexane:isopropanol 85:15, 1 mL/min, 25° C.): t$_R$=4.394 min.

LC (GC METHOD 1): t$_R$=13.32 min; Mass spectrum: m/z=334/6 [M]$^+$.

Intermediate 44

2-(4-Bromo-3,5-dimethyl-phenoxy)-2-methyl-propionamide

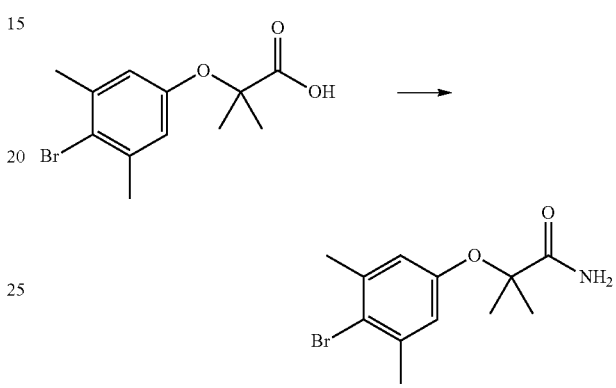

The material obtained in Step 1 of the preparation of Intermediate 40 (1.5 g) is allowed to react with 1,1'-carbonyldiimidazole (0.75 g) in dry tetrahydrofuran (10 mL). After 3 hours 30% aqueous ammonium hydroxide (11 mL) is added and the mixture stirred for 30 min. The solvent is evaporated under reduced pressure, the residue in EtOAc washed consecutively with excess aqueous HCl (0.2 M), saturated aqueous NaHCO$_3$ and brine, dried and the solvent evaporated in vacuo to give the desired product (0.51 g of ca. 90% content).

LC (LC METHOD 1): t$_R$=1.16 min; Mass spectrum: m/z=286/8 [M+H]$^+$.

Intermediate 45

2-Bromo-5-(4-methanesulfonyl-butoxy)-1,3-dimethyl-benzene

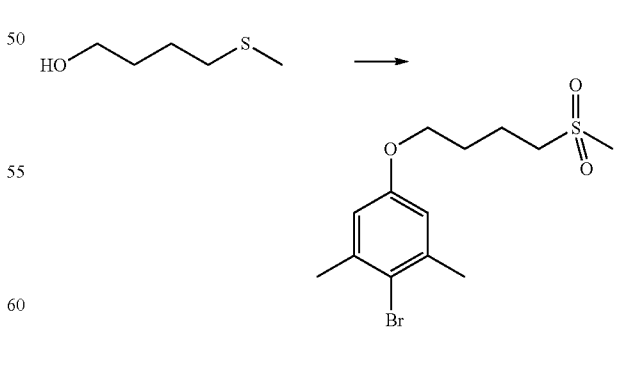

The title compound is prepared from 4-(methylthio)butanol (1.0 g, 8.32 mmol) in a manner analogous to that described for Intermediate 28 (Yield 1.74 g).

LC (LC METHOD 4): t$_R$=7.20 min; Mass spectrum (ES+): m/z=335 [M+H]$^+$.

Intermediate 46

[1-(4-Bromo-3,5-dimethyl-phenoxymethyl)-cyclopropyl]-methanol

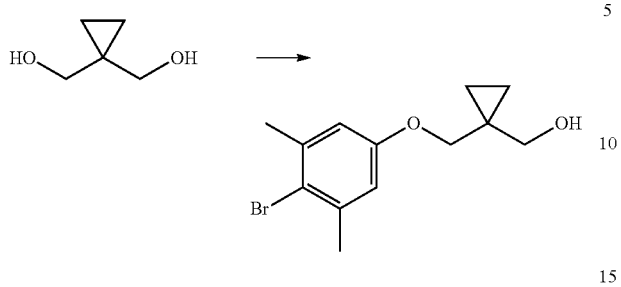

1,1-Bis(hydroxymethyl)cyclopropane (3.05 g, 29.84 mmol) 4-bromo-3,5-dimethylphenol (1.5 g, 7.46 mmol), di-tert-butylazodicarboxylate (1.89 g, 8.21 mmol) and triphenylphosphine (2.15 g, 8.21 mmol) are suspended in dry tetrahydrofuran (10 mL) and stirred overnight. The mixture is washed with saturated sodium carbonate solution, dried and the solvent removed. The residue is purified by flash chromatography (0-30% ethyl acetate in cyclohexane) to give the title compound (Yield 1.80 g of approx 70% content).

LC (LC METHOD 2): $t_R$=1.36 min; Mass spectrum: m/z=267/9 [M−OH]$^+$.

Intermediate 47

(1S,2S)-2-(4-{(R)-7-Fluoro-4-[4-(3-methanesulfonyl-propoxy)-2,6-dimethyl-phenyl]-indan-1-yloxy}-Phenyl)-cyclopropanecarboxylic acid ethyl ester

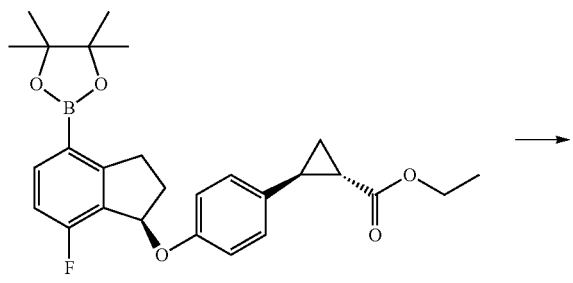

(1S,2S)-2-{4-[(R)-7-Fluoro-4-(4,4,5,5-tetramethyl-[4,3,2]dioxaborolan-2-yl)-indan-1-yloxy]-phenyl}-cyclopropanecarboxylic acid ethyl ester (Intermediate 24, 286 mg) is dissolved in a mixture of toluene (10 mL) and water (2 mL) and degassed with a flow of argon. 2-Bromo-5-(3-methanesulfonyl-propoxy)-1,3-dimethyl-benzene (Intermediate 28, 196 mg), tri-potassium phosphate (388 mg), 2-dicyclohexylphosphino-2',6'-dimethoxybiphenyl (S-Phos, 25 mg) and palladium (II) acetate (14 mg) are added and the mixture is heated at 100° C. for 4 hours under argon. The mixture is cooled to room temperated and diluted with ethyl acetate and water, the phases are separated and the organic phase washed with water, dried and the solvent removed. The residue is purified by flash chromatography (5% ethyl acetate in cyclohexane) to give the title compound (Yield 308 mg).

LC (LC METHOD 3): $t_R$=1.50 min; Mass spectrum (ES+): m/z=598 [M+NH4]$^+$.

The Intermediates in the following table are prepared in analogy with the procedure used for the preperation of Intermediate 47 from the starting intermediates described:

TABLE 4

| Intermediate | Structure | Name | Starting intermediates | Yield | Analysis |
|---|---|---|---|---|---|
| 48 | (structure shown) | (1R,2R)-2-(4-{(R)-7-Fluoro-4-[4-(3-methanesulfonyl-propoxy)-2,6-dimethyl-phenyl]-indan-1-yloxy}-phenyl)-cyclopropane-carboxylic acid ethyl ester | Intermediate 25 (700 mg) and Intermediate 28 (964 mg) | 960 mg | LC (LC METHOD 2): $t_R$ = 0.68 min; Mass spectrum (ES+): m/z = 581 [M + H]$^+$. |

TABLE 4-continued

| Intermediate | Structure | Name | Starting intermediates | Yield | Analysis |
|---|---|---|---|---|---|
| 49 | 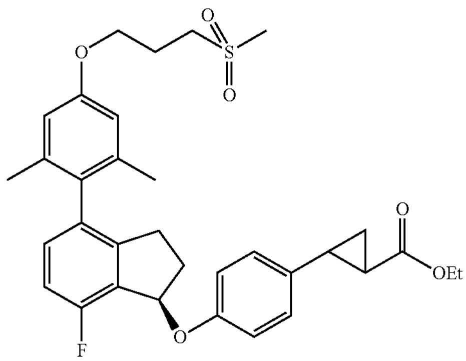 [SMILES: CCOC(=O)C1CC1c1ccc(O[C@@H]2CCc3c(-c4c(C)cc(OCCCS(C)(=O)=O)cc4C)ccc(F)c32)cc1] | 2-(4-{(R)-7-Fluoro-4-[4-(3-methanesulfonyl-propoxy)-2,6-dimethyl-phenyl]-indan-1-yloxy}-phenyl)-trans-cyclopropane-carboxylic acid ethyl ester | Intermediate 26 (88 mg) and Intermediate 28 (121 mg) heating under microwave irradiation at 120° C. for 2 hours | 24 mg | LC (LC METHOD 4): $t_R$ = 8.22 min; Mass spectrum (ES+): m/z = 581 [M + H]+. |
| 50 | 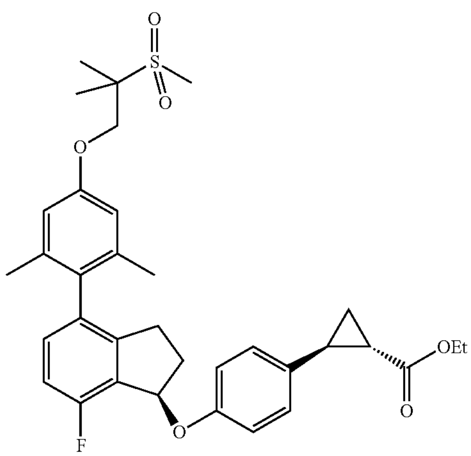 [SMILES: CCOC(=O)[C@H]1C[C@@H]1c1ccc(O[C@@H]2CCc3c(-c4c(C)cc(OCC(C)(C)S(C)(=O)=O)cc4C)ccc(F)c32)cc1] | (1S,2S)-2-(4-{(R)-7-Fluoro-4-[4-(2-methanesulfonyl-2-methyl-propoxy)-2,6-dimethyl-phenyl]-indan-1-yloxy}-phenyl)-cyclo-propanecarboxylic acid ethyl ester | Intermediate 24 (171 mg) and Intermediate 29 (111 mg) | 107 mg | LC (LC METHOD 4): $t_R$ = 8.61 min; Mass spectrum (ES+): m/z = 595 [M + H]+. |
| 51 | 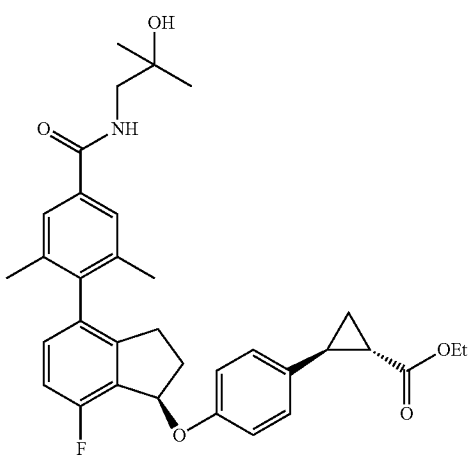 [SMILES: CCOC(=O)[C@H]1C[C@@H]1c1ccc(O[C@@H]2CCc3c(-c4c(C)cc(C(=O)NCC(C)(C)O)cc4C)ccc(F)c32)cc1] | (1S,2S)-2-(4-{(R)-7-Fluoro-4-[4-(2-hydroxy-2-methyl-propylcarbamoyl)-2,6-dimethyl-phenyl]-indan-1-yloxy}-phenyl)-cyclopropanecarboxylic acid ethyl ester | Intermediate 24 (150 mg) and Intermediate 30 (145 mg) | 35 mg | LC (LC METHOD 2): $t_R$ = 1.42 min; Mass spectrum (ES+): m/z = 560 [M + H]+. |
| 52 | 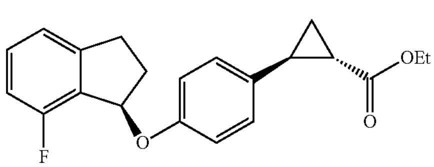 [SMILES: CCOC(=O)[C@H]1C[C@@H]1c1ccc(O[C@@H]2CCc3cccc(F)c32)cc1] | (1S,2S)-2-[4-((R)-7-Fluoro-indan-1-yloxy)-phenyl}-cyclo-propanecarboxylic acid ethyl ester | Isolated as a byproduct in the preperation of Intermediate 51 above | 67 mg | LC (LC METHOD 4): $t_R$ = 8.07 min; Mass spectrum (ES+): m/z = 341 [M + H]+. |

TABLE 4-continued

| Intermediate | Structure | Name | Starting intermediates | Yield | Analysis |
|---|---|---|---|---|---|
| 53 | 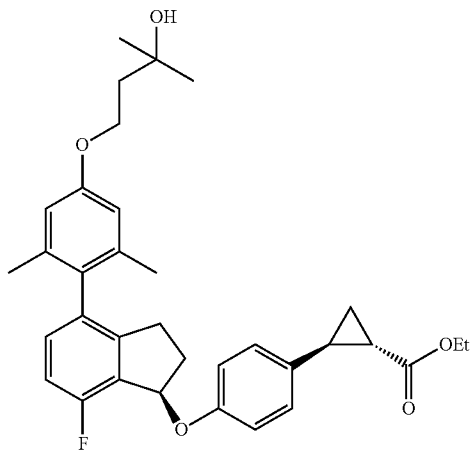 [SMILES: CCOC(=O)[C@H]1C[C@@H]1c1ccc(O[C@@H]2CCc3c(-c4c(C)cc(OCCC(C)(C)O)cc4C)ccc(F)c32)cc1] | (1S,2S)-2-(4-{(R)-7-Fluoro-4-[4-(3-hydroxy-3-methyl-butoxy)-2,6-dimethyl-phenyl]-indan-1-yloxy}-phenyl)-cyclopropane-carboxylic acid ethyl ester | Intermediate 24 (150 mg) and Intermediate 31 (98 mg) | 25 mg | LC (LC METHOD 2): $t_R$ = 1.67 min; Mass spectrum (ES+): m/z = 529 [M − OH]⁺. |
| 54 | 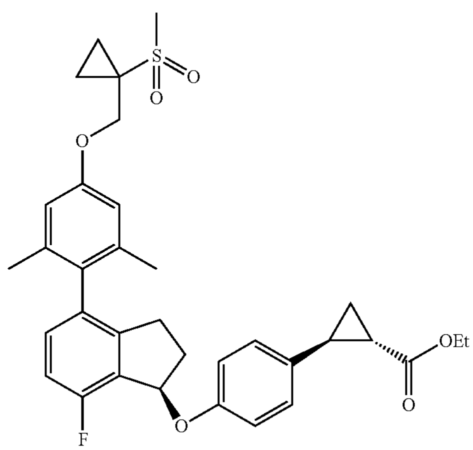 [SMILES: CCOC(=O)[C@H]1C[C@@H]1c1ccc(O[C@@H]2CCc3c(-c4c(C)cc(OCC5(S(C)(=O)=O)CC5)cc4C)ccc(F)c32)cc1] | (1S,2S)-2-(4-{(R)-7-Fluoro-4-[4-(1-methanesulfonyl-cyclopropylmethoxy)-2,6-dimethyl-phenyl]-indan-1-yloxy)-phenyl)-cyclopropanecarboxylic acid ethyl ester | Intermediate 24 (313 mg) and Intermediate 32 (200 mg) | 90 mg | LC (LC METHOD 4): $t_R$ = 8.55 min; Mass spectrum (ES+): m/z = 593 [M + H]⁺. |
| 55 | 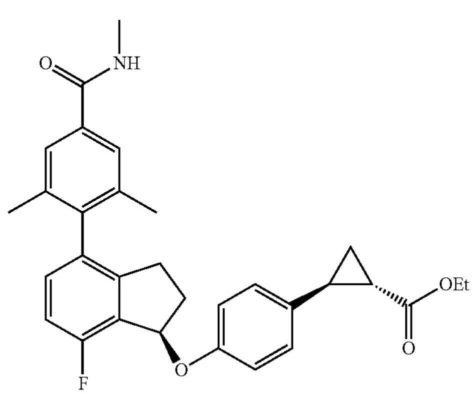 [SMILES: CCOC(=O)[C@H]1C[C@@H]1c1ccc(O[C@@H]2CCc3c(-c4c(C)cc(C(=O)NC)cc4C)ccc(F)c32)cc1] | (1S,2S)-2-{4-[(R)-4-(2,6-Dimethyl-4-methylcarbamoyl-phenyl)-7-fluoro-indan-1-yloxy]-phenyl}-cyclopropanecarboxylic acid ethyl ester | Intermediate 24 (150 mg) and Intermediate 33 (98 mg) | 40 mg | LC (LC METHOD 2): $t_R$ = 1.45 min; Mass spectrum (ES+): m/z = 502 [M + H]⁺. |

TABLE 4-continued

| Intermediate | Structure | Name | Starting intermediates | Yield | Analysis |
|---|---|---|---|---|---|
| 56 | 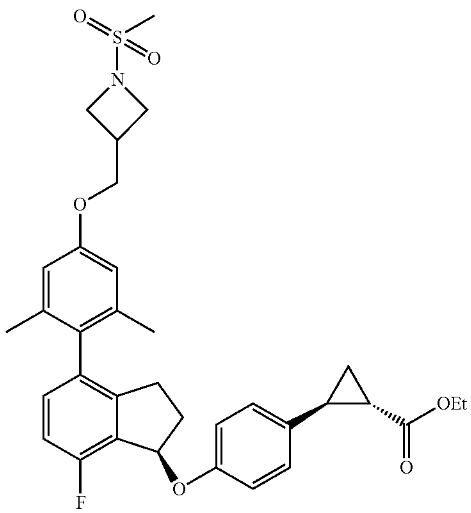 [SMILES: CCOC(=O)[C@H]1C[C@@H]1c1ccc(O[C@@H]2CCc3c(-c4c(C)cc(OCC5CN(S(C)(=O)=O)C5)cc4C)ccc(F)c32)cc1] | (1S,2S)-2-(4-{(R)-7-Fluoro-4-[4-(1-methanesulfonyl-azetidin-3-ylmethoxy)-2,6-dimethyl-phenyl]-indan-1-yloxy}-phenyl)-cyclopropanecarboxylic acid ethyl ester | Intermediate 24 (184 mg) and Intermediate 34 (119 mg) | 145 mg | LC (LC METHOD 3): $t_R$ = 1.54 min; Mass spectrum (ES+): m/z = 608 [M + H]$^+$. |
| 57 | 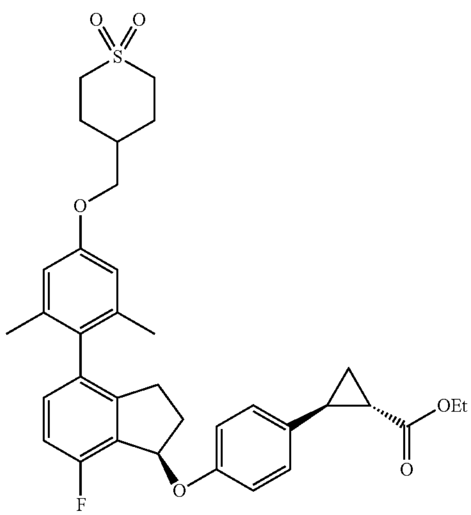 [SMILES: CCOC(=O)[C@H]1C[C@@H]1c1ccc(O[C@@H]2CCc3c(-c4c(C)cc(OCC5CCS(=O)(=O)CC5)cc4C)ccc(F)c32)cc1] | (1S,2S)-2-(4-{(R)-4-[4-(1,1-Dioxo-hexahydro-1-thiopyran-4-ylmethoxy)-2,6-dimethyl-phenyl]-7-fluoro-indan-1-yloxy}-phenyl)-cyclopropanecarboxylic acid ethyl ester | Intermediate 24 (134 mg) and Intermediate 35 (87 mg) | 117 mg | LC (LC METHOD 4): $t_R$ = 8.47 min; Mass spectrum (ES+): m/z = 607 [M + H]$^+$. |
| 58 | 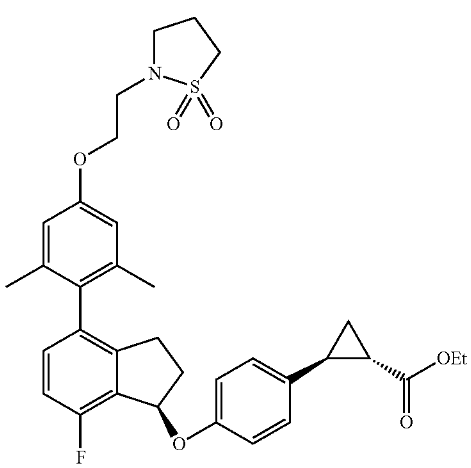 [SMILES: CCOC(=O)[C@H]1C[C@@H]1c1ccc(O[C@@H]2CCc3c(-c4c(C)cc(OCCN5CCCS5(=O)=O)cc4C)ccc(F)c32)cc1] | (1S,2S)-2-[4-((R)-4-{4-[2-(1,1-Dioxo-1-isothiazolidin-2-yl)-ethoxy]-2,6-dimethyl-phenyl}-7-fluoro-indan-1-yloxy)-phenyl] cyclopropanecarboxylic acid ethyl ester | Intermediate 24 (163 mg) and Intermediate 36 (135 mg) | 55 mg | LC (LC METHOD 3): $t_R$ = 1.53 min; Mass spectrum (ES+): m/z = 608 [M + H]$^+$. |

TABLE 4-continued

| Intermediate | Structure | Name | Starting intermediates | Yield | Analysis |
|---|---|---|---|---|---|
| 59 | 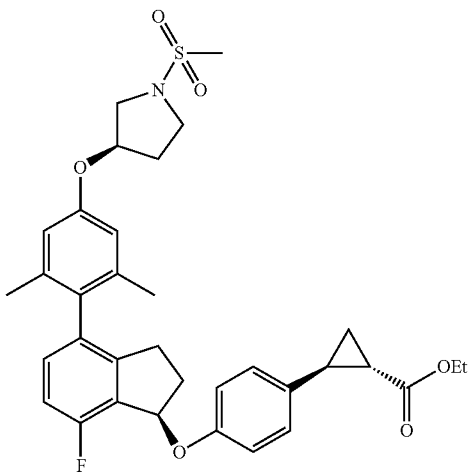 [SMILES: CCOC(=O)[C@H]1C[C@@H]1c1ccc(O[C@@H]2CCc3c(-c4c(C)cc(O[C@@H]5CCN(S(C)(=O)=O)C5)cc4C)ccc(F)c32)cc1] | (1S,2S)-2-(4-{(R)-7-Fluoro-4-[4-((R)-1-methanesulfonyl-pyrrolidin-3-yloxy)-2,6-dimethyl-phenyl]-indan-1-yloxy}-phenyl)-cyclopropanecarboxylic acid ethyl ester | Intermediate 24 (139 mg) and Intermediate 37 (91 mg) | 34 mg | LC (LC METHOD 3): $t_R$ = 1.55 min; Mass spectrum (ES+): m/z = 625 [M + NH$_4$]$^+$. |
| 60 | 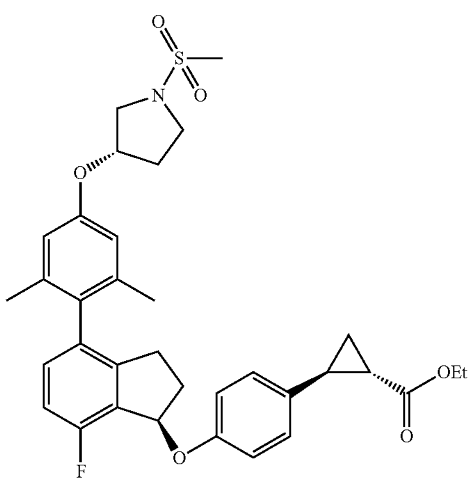 [SMILES: CCOC(=O)[C@H]1C[C@@H]1c1ccc(O[C@@H]2CCc3c(-c4c(C)cc(O[C@H]5CCN(S(C)(=O)=O)C5)cc4C)ccc(F)c32)cc1] | (1S,2S)-2-(4-{(R)-7-Fluoro-4-[4-((S)-1-methanesulfonyl-pyrrolidin-3-yloxy)-2,6-dimethyl-phenyl]-indan-1-yloxy}-phenyl)-cyclopropanecarboxylic acid ethyl ester | Intermediate 24 (191 mg) and Intermediate 38 (126 mg) | 66 mg | LC (LC METHOD 3): $t_R$ = 1.54 min; Mass spectrum (ES+): m/z = 625 [M + NH$_4$]$^+$. |
| 61 | 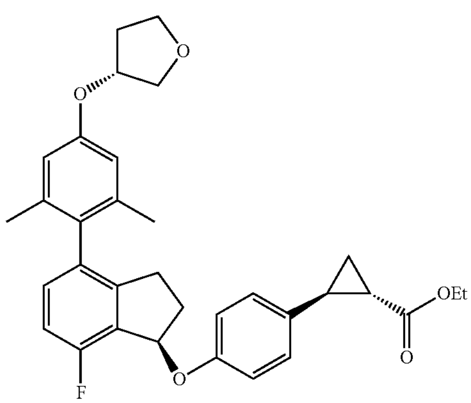 [SMILES: CCOC(=O)[C@H]1C[C@@H]1c1ccc(O[C@@H]2CCc3c(-c4c(C)cc(O[C@@H]5CCOC5)cc4C)ccc(F)c32)cc1] | (1S,2S)-2-[4-((R)-4-{2,6-Dimethyl-4-[(R)-(tetrahydro-furan-3-yl)oxy]-phenyl}-7-fluoro-indan-1-yloxy)-phenyl]-cyclopropanecarboxylic acid ethyl ester | Intermediate 24 (200 mg) and Intermediate 39 (136 mg) | 76 mg | LC (LC METHOD 2): $t_R$ = 0.90 min; Mass spectrum (ES+): m/z = 548 [M + NH$_4$]$^+$. |

TABLE 4-continued

| Intermediate | Structure | Name | Starting intermediates | Yield | Analysis |
|---|---|---|---|---|---|
| 62 | 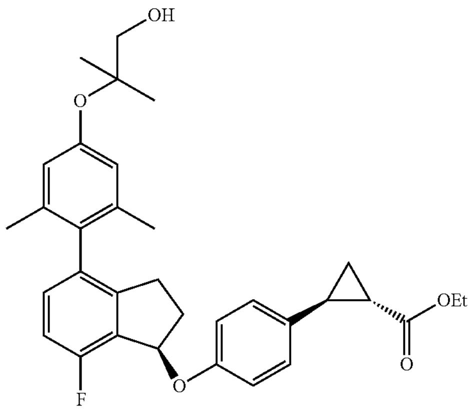 [SMILES: CCOC(=O)[C@H]1C[C@@H]1c1ccc(O[C@@H]2CCc3c(-c4c(C)cc(OC(C)(C)CO)cc4C)ccc(F)c32)cc1] | (1S,2S)-2-(4-{(R)-7-Fluoro-4-[4-(2-hydroxy-1,1-dimethyl-ethoxy)-2,6-dimethyl-phenyl]-indan-1-yloxy}-phenyl)-cyclopropanecarboxylic acid ethyl ester | Intermediate 24 (200 mg) and Intermediate 40 (104 mg) | 90 mg | LC (LC METHOD 3): $t_R$ = 1.57 min; Mass spectrum (ES+): m/z = 550 $[M + NH_4]^+$. |
| 63 | 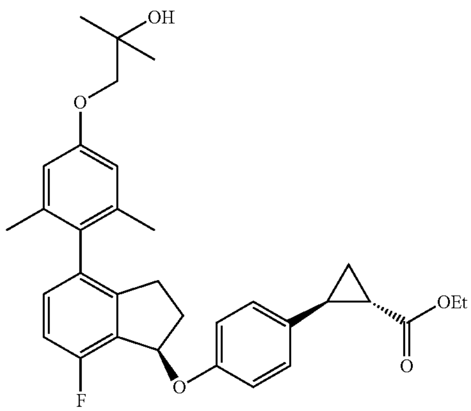 [SMILES: CCOC(=O)[C@H]1C[C@@H]1c1ccc(O[C@@H]2CCc3c(-c4c(C)cc(OCC(C)(C)O)cc4C)ccc(F)c32)cc1] | (1S,2S)-2-(4-{(R)-7-Fluoro-4-[4-(2-hydroxy-2-methyl-propoxy)-2,6-dimethyl-phenyl]-indan-1-yloxy}-phenyl)-cyclopropanecarboxylic acid ethyl ester | Intermediate 24 (200 mg) and Intermediate 41 (124 mg) | 130 mg | LC (LC METHOD 2): $t_R$ = 1.64 min; Mass spectrum (ES+): m/z = 515 $[M - OH]^+$. |
| 64 | 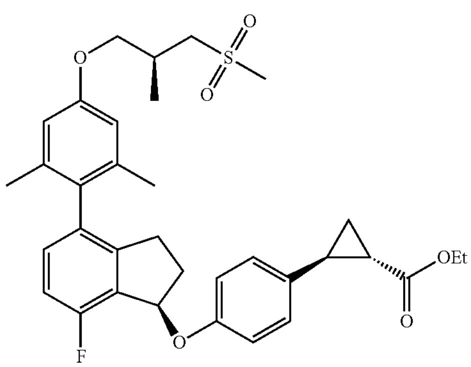 [SMILES: CCOC(=O)[C@H]1C[C@@H]1c1ccc(O[C@@H]2CCc3c(-c4c(C)cc(OC[C@H](C)CS(C)(=O)=O)cc4C)ccc(F)c32)cc1] | (1S,2S)-2-(4-{(R)-7-Fluoro-4-[4-((S)-3-methanesulfonyl-2-methyl-propoxy)-2,6-dimethyl-phenyl]-indan-1-yloxy}-phenyl)-cyclopropanecarboxylic acid ethyl ester | Intermediate 24 (108 mg) and Intermediate 42 (93 mg) | 75 mg | LC (LC METHOD 4): $t_R$ = 8.79 min; Mass spectrum (ES+): m/z = 595 $[M + H]^+$. |
| 65 | 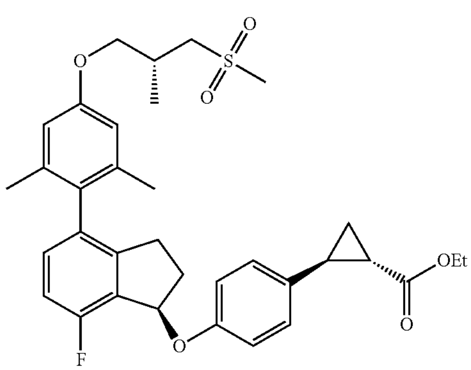 [SMILES: CCOC(=O)[C@H]1C[C@@H]1c1ccc(O[C@@H]2CCc3c(-c4c(C)cc(OC[C@@H](C)CS(C)(=O)=O)cc4C)ccc(F)c32)cc1] | (1S,2S)-2-(4-{(R)-7-Fluoro-4-[4-((R)-3-methanesulfonyl-2-methyl-propoxy)-2,6-dimethyl-phenyl]-indan-1-yloxyl-phenyl)-cyclopropanecarboxylic acid ethyl ester | Intermediate 24 (200 mg) and Intermediate 43 (152 mg) | 160 mg | LC (LC METHOD 2): $t_R$ = 1.59 min; Mass spectrum (ES+): m/z = 595 $[M + H]^+$. |

TABLE 4-continued

| Intermediate | Structure | Name | Starting intermediates | Yield | Analysis |
|---|---|---|---|---|---|
| 66 | 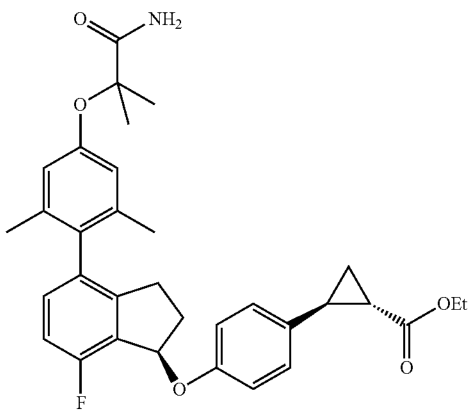 [SMILES: CCOC(=O)[C@H]1C[C@@H]1c1ccc(O[C@@H]2CCc3c(-c4c(C)cc(OC(C)(C)C(N)=O)cc4C)ccc(F)c32)cc1] | (1S,2S)-2-(4-{(R)-4-[4-(1-Carbamoyl-1-methyl-ethoxy)-2,6-dimethyl-phenyl]-7-fluoro-indan-1-yloxy}-phenyl)-cyclopropanecarboxylic acid ethyl ester | Intermediate 24 (200 mg) and Intermediate 44 (130 mg) | 50 mg | LC (LC METHOD 2): $t_R$ = 1.52 min; Mass spectrum (ES+): m/z = 546 [M + H]$^+$. |
| 67 | 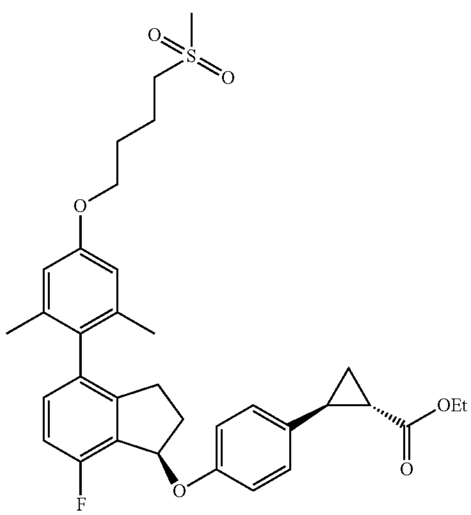 [SMILES: CCOC(=O)[C@H]1C[C@@H]1c1ccc(O[C@@H]2CCc3c(-c4c(C)cc(OCCCCS(C)(=O)=O)cc4C)ccc(F)c32)cc1] | (1S,2S)-2-(4-{(R)-7-Fluoro-4-[4-(4-methanesulfonyl-butoxy)-2,6-dimethyl-phenyl]-indan-1-yloxy}-phenyl)-cyclopropanecarboxylic ethyl ester | Intermediate 24 (150 mg) and Intermediate 45 (216 mg) | 80 mg | LC (LC METHOD 2): $t_R$ = 1.52 min; Mass spectrum (ES+): m/z = 612 [M + NH$_4$]$^+$. |
| 68 | 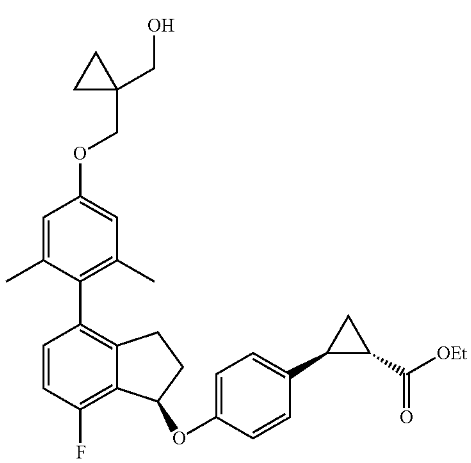 [SMILES: CCOC(=O)[C@H]1C[C@@H]1c1ccc(O[C@@H]2CCc3c(-c4c(C)cc(OCC5(CO)CC5)cc4C)ccc(F)c32)cc1] | (1S,2S)-2-(4-{(R)-7-Fluoro-4-[4-(1-hydroxymethyl-cyclopropylmethoxy)-2,6-dimethyl-phenyl]-1-yloxy}-phenyl)-cyclopropanecarboxylic acid ethyl ester | Intermediate 24 (200 mg) and Intermediate 46 (130 mg) | 65 mg | LC (LC METHOD 2): $t_R$ = 1.60 min; Mass spectrum (ES+): m/z = 562 [M + NH$_4$]$^+$. |

Intermediate 69

2-{-4-[(R)-4-(2,6-Dimethyl-phenyl)-7-fluoro-indan-1-yloxy]-phenyl}-trans-cyclopropanecarboxylic acid ethyl ester

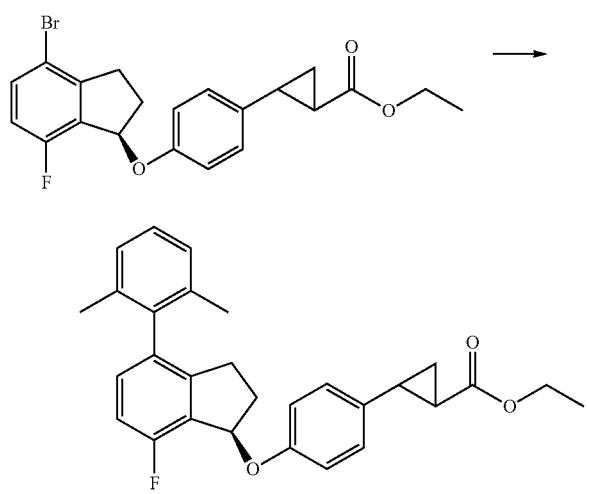

The title compound is prepared from 2-[4-((R)-4-Bromo-7-fluoro-indan-1-yloxy)-2-methoxyphenyl]-trans-cyclopropanecarboxylic acid ethyl ester (Intermediate 14, 50 mg) and 2,6-dimethylphenyl boronic acid (36 mg) in a manner analogous to that described for Intermediate 31, heating under microwave irradiation at 120° C. for 2 hours (Yield 80 mg crude product).

LC (LC METHOD 4): $t_R$=9.24 min; Mass spectrum (ES+): m/z=445 [M+H]$^+$.

Intermediate 70

Methanesulfonic acid 1,1-dioxo-hexahydro-1-thiopyran-4-ylmethyl ester

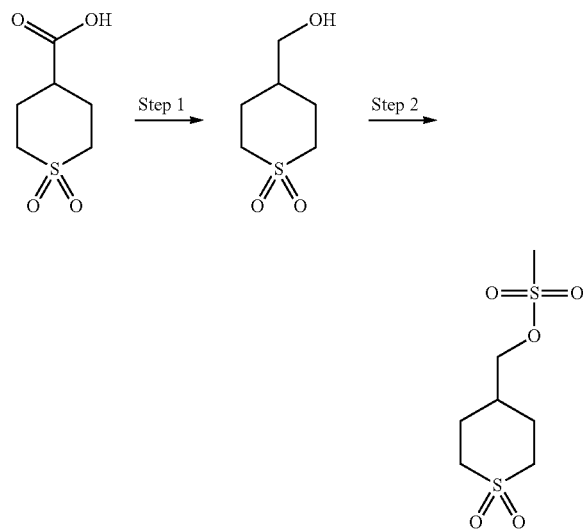

Step 1: (1,1-Dioxo-hexahydro-1-thiopyran-4-yl)-methanol 1,1-dioxo-tetrahydro-2H-thiopyran-4-carboxylic acid (4.5 g, 25.25 mmol) is dissolved in dry tetrahydrofuran (150 mL). The reaction mixture is cooled to 0° C. and borane tetrahydrofuran complex (1 M in tetrahydrofuran, 27.78 mL, 27.78 mmol) is added dropwise. After stirring for 1 hour at 0° C., the mixture is stirred at room temperature overnight; then, it is concentrated under vacuum, partitioned between dichloromethane and water, dried (MgSO$_4$) and concentrated under vacuum to give the title compound (Yield: 1.70 g), which is used in the next step without any other purification.

Step 2: Methanesulfonic acid 1,1-dioxo-hexahydro-1-thiopyran-4-ylmethyl ester Methanesulfonyl chloride (0.88 mL, 11.39 mmol), (1,1-Dioxo-hexahydro-1-thiopyran-4-yl)-methanol (1.7 g, 10.35 mmol) and triethylamine (4.32 mL 31.06 mmol) are stirred at 0° C. in dry dichloromethane (100 mL). After 30 min, the reaction mixture is warmed to ambient temperature. After stirring for 2 hours, the reaction mixture is concentrated under vacuum. The crude product obtained is triturated with a solution of cyclohexane/ethylacetate 70/30 and the solid obtained is filtered and dried under vacuum. (Yield: 2.3 g)

Intermediate 71

Methanesulfonic acid 3-methanesulfonyl-propyl ester

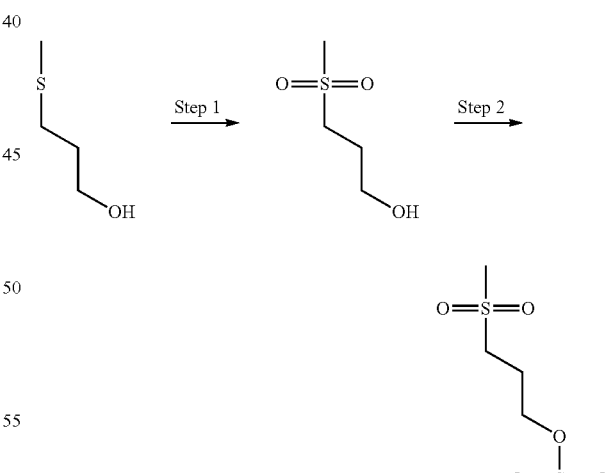

Step 1: 3-(Methylsulphonyl)-1-propanol

The title compound is prepared from 2-methylthiopropanol (2 g, 18.83 mmol) following a similar procedure to that reported in: patent US2003/225111 A1 (Yield: 600 mg).

Step 2: Methanesulfonic acid 3-methanesulfonyl-propyl ester

The title compound is prepared starting from 3-(methylsulphonyl)-1-propanol (600 mg, 4.34 mmol) following a similar procedure to that reported in: Journal of Medicinal Chemistry, 1995, vol. 38, #11 p. 2009-2017 (Yield: 210 mg).

Intermediate 72

(1S,2S)-2-(4-{(R)-5-Cyano-4-[4-(3-hydroxy-3-methyl-butoxy)-2,6-dimethyl-phenyl]-indan-1-yloxy}-phenyl)-cyclopropanecarboxylic acid ethyl ester

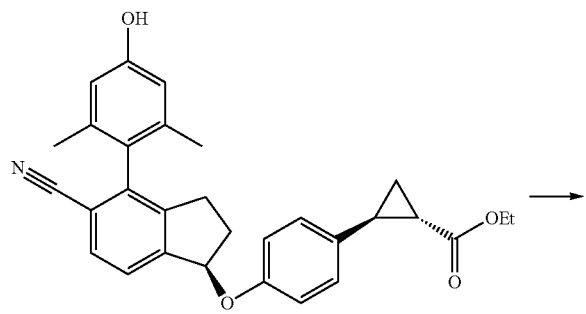

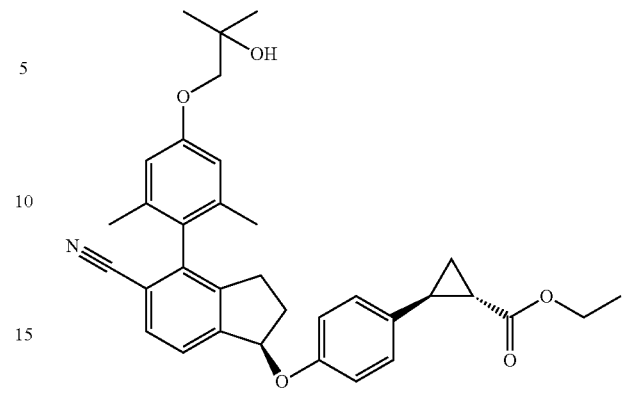

Intermediate 27 (95 mg, 0.16 mmol), toluene-4-sulfonic acid 3-hydroxy-3-methyl-butyl ester, (Intermediate 31 step 1, 63 mg, 0.24 mmol) and $CsCO_3$ (110 mg, 0.33 mmol) are suspended in 2 mL of N,N-dimethylformamide. The reaction mixture is stirred at 110° C. for 3 h, then it is concentrated under vacuum. The crude product obtained is dissolved in dichloromethane, the organic phase is washed with water, collected, dried over sodium sulfate and concentrated under vacuum. The crude product obtained is purified by flash chromatography (cyclohexane/ethyl acetate 100/01→70/30) to give the title compound (Yield: 45 mg).

LC (LC METHOD 1): $t_R$=1.55 min; Mass spectrum (ES+): m/z=572 $[M+NH_4]^+$.

The following intermediates are synthesised in analogy to Intermediate 72 starting from the correspondent intermediates as reported in the table below:

TABLE 5

| Intermediate | Structure | Name | Starting intermediates | Yield | Analysis |
|---|---|---|---|---|---|
| 73 | (structure shown) | (1S,2S)-2-(4-{(R)-5-Cyano-4-[4-(1,1-dioxo-hexahydro-thiopyran-4-ylmethoxy)-2,6-dimethyl-phenyl-indan-1-yloxy}-phenyl)-cyclopropanecarboxylic acid ethyl ester | Intermediate 27 (100 mg) and Intermediate 70 (62 mg) | 35 mg | LC (LC METHOD 1): $t_R$ = 1.48 min; Mass spectrum (ES+): m/z = 631 $[M + NH4]^+$. |

TABLE 5-continued

| Intermediate | Structure | Name | Starting intermediates | Yield | Analysis |
|---|---|---|---|---|---|
| 74 | 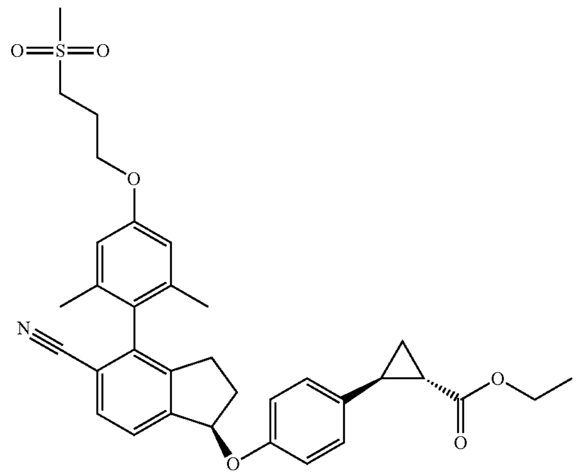 [SMILES: CCOC(=O)[C@H]1C[C@@H]1c1ccc(O[C@@H]2CCc3c2ccc(C#N)c3-c2c(C)cc(OCCCS(C)(=O)=O)cc2C)cc1] | (1S,2S)-2-(4-{(R)-5-Cyano-4-[4-(3-methanesulfonyl-propoxy)-2,6-dimethyl-phenyl]-indan-1-yloxy}-phenyl)-cyclopropane-carboxylic acid ethyl ester | Intermediate 27 (100 mg) and Intermediate 71 (56 mg) | 45 mg | LC (LC METHOD 1): $t_R$ = 1.43 min; Mass spectrum (ES+): m/z = 605 [M + NH4]+. |
| 75 | 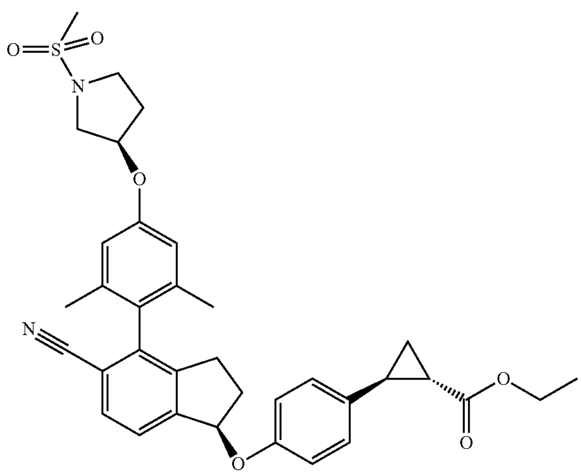 [SMILES: CCOC(=O)[C@H]1C[C@@H]1c1ccc(O[C@@H]2CCc3c2ccc(C#N)c3-c2c(C)cc(O[C@@H]3CCN(S(C)(=O)=O)C3)cc2C)cc1] | (1S,2S)-2-(4-{(R)-5-Cyano-4-[4-((R)-1-methanesulfonyl-pyrrolidin-3-yloxy)-2,6-dimethyl-phenyl]-indan-1-yloxy}-phenyl)-cyclopropanecarboxylic acid ethyl ester | Intermediate 27 (100 mg) and Intermediate 37 step 1 (62 mg) | 45 mg | LC (LC METHOD 7): $t_R$ = 4.19 min; Mass spectrum (ES+): m/z = 615 [M + H]+. |
| 76 | 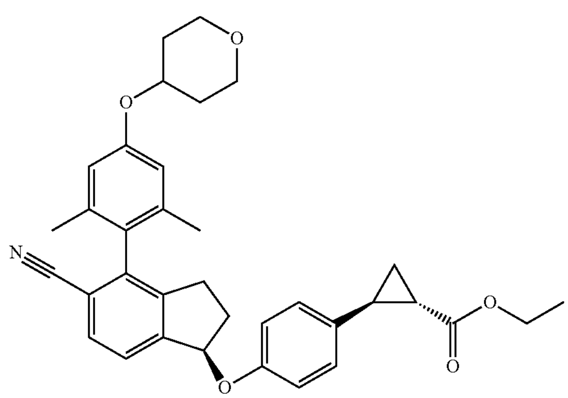 [SMILES: CCOC(=O)[C@H]1C[C@@H]1c1ccc(O[C@@H]2CCc3c2ccc(C#N)c3-c2c(C)cc(OC3CCOCC3)cc2C)cc1] | (1S,2S)-2-(4-{(R)-5-Cyano-4-[2,6-dimethyl-4-(tetrahydro-pyran-4-yloxy)-phenyl]-indan-1-yloxy}-phenyl)-cyclopropanecarboxylic acid ethyl ester | Intermediate 27 (100 mg) and toluene-4-sulfonic acid tetrahydro-pyran-4-yl ester (EP1367058, 62 mg) | 45 mg | TLC $R_f$ 0.7 (cyclohexane/ethyl acetate 7:3) |

Intermediate 77

4-(4-Bromo-3,5-dimethyl-phenoxymethyl)-1,1-dioxo-hexahydro-1-thiopyran-4-ol

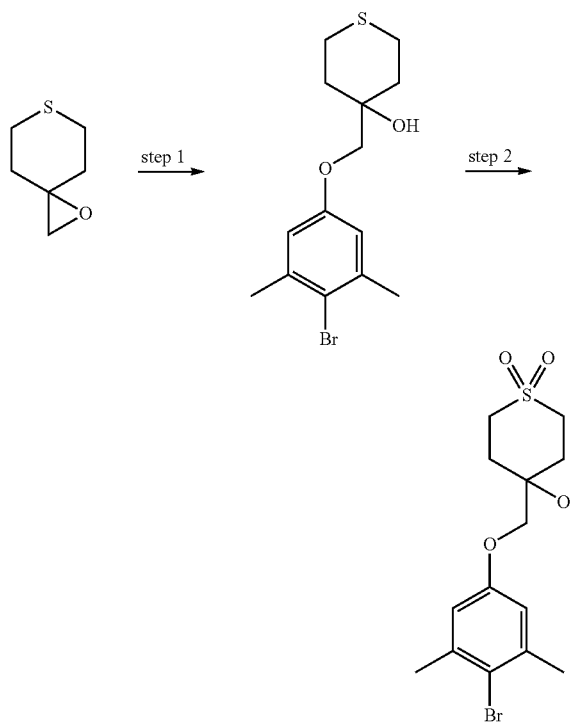

Step 1: 4-(4-Bromo-3,5-dimethyl-phenoxymethyl)-tetrahydro-thiopyran-4-ol

1-Oxa-6-thia-spiro[2.5]octane (EP1726580 A1, 750 mg, 80% content, 4.61 mmol), 4-bromo-3,5-dimethylphenol (2.32 g, 11.52 mmol) and cesium carbonate (3.0 g, 9.22 mmol) are suspended in dry N,N-dimethylformamide (20 mL) and stirred for 10 minutes at room temperature followed by 3 hours at 100° C. The mixture is concentrated under vacuum, partitioned between water and dichloromethane, the organic layer separated and concentrated under vacuum and the residue purified by flash chromatography (50-100% EtOAc in cyclohexane) to give the title compounds (820 mg).

GC (MIL__03__001): $t_R$=13.54 min; Mass spectrum (ES+): m/z=330, 332 [M]+.

Step 2: 4-(4-Bromo-3,5-dimethyl-phenoxymethyl)-1,1-dioxo-hexahydro-1-thiopyran-4-ol 4-(4-Bromo-3,5-dimethyl-phenoxymethyl)-tetrahydro-thiopyran-4-ol (819 mg), is suspended in tetrahydrofuran (2 mL) and Oxone® (4.33 g, 7.05 mmol) in water (2 mL) is added dropwise. The mixture is stirred at room temperature then diluted with water and dichloromethane, the phases separated and the organic phase evaporated under vacuum. The residue is purified by flash chromatography (20-100% EtOAc in cyclohexane) to give the title compound (Yield: 850 mg).

GC (MIL__03__004): $t_R$=9.35 min; Mass spectrum (ES+): m/z=362, 364 [M]+.

Intermediate 78

1-[3-(4-Bromo-3,5-dimethyl-phenyl)-5-methyl-[1,2,4]triazol-1-yl]-2-methyl-propan-2-ol

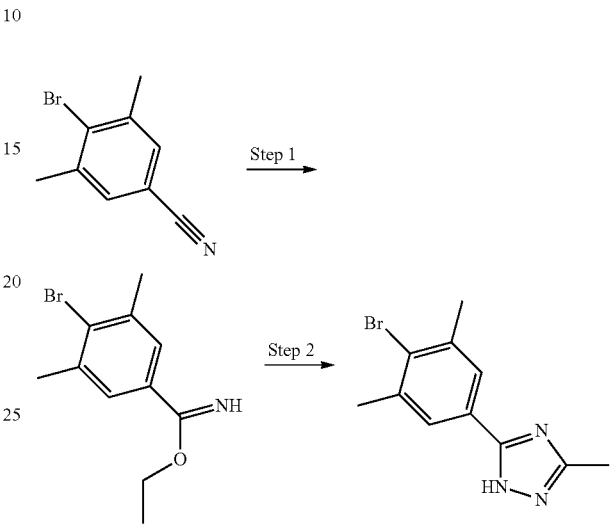

Step 1:

4-Bromo-3,5-dimethyl benzonitrile (5.0 g) is dissolved in HCl in dioxane (4 M, 17.3 mL) and EtOH (5 mL) added. After stirring for 16 h volatiles are evaporated in vacuo and the crude residue (6.5 g) used as such in the next step.

Step 2:

Acetic hydazide (3.7 g) is added to a stirred solution of the product from Step 1 (6.5 g) in triethylamine (3.6 g) and dioxane (15 mL). After 24 h the solvent is removed in vacuum, water (20 mL) added and the mixture extracted with EtOAc. The organic layer is dried (Na$_2$SO$_4$), concentrated and the residue chromatographed (silica gel, cyclohexane/ ethyl acetate 80:20 to 20:80) to give the desired intermediate (0.70 g).

LC (LC METHOD 1): $t_R$=0.98 min; Mass spectrum (ES+): m/z=266/268 [M+H]+.

Intermediate 79

1-[3-(4-Bromo-3,5-dimethyl-phenyl)-5-methyl-[1,2,4]triazol-1-yl]-2-methyl-propan-2-ol

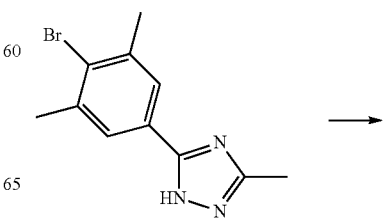

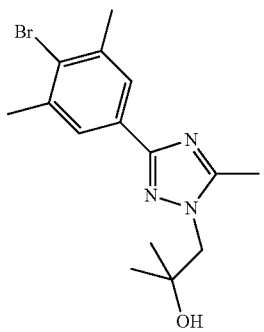

A mixture of Intermediate 78 (0.35 g), isobutylene oxide (0.13 mL) and cesium carbonate (0.81 g) in N,N-dimethylformamide (5 mL) in a closed vessel is stirred at 120° C. for 16 h.

Volatiles are removed under reduced pressure and the residue purified by chromatography (silica gel, cyclohexane/ethyl acetate 100:0 to 60:40) to give the title compound (0.16 g).

LC (LC METHOD 1): $t_R$=1.12 min; Mass spectrum (ES+): m/z=338/340 [M+H]$^+$.

Intermediate 80

3-(4-Bromo-3,5-dimethyl-phenyl)-1,5-dimethyl-1H-[1,2,4]-triazole

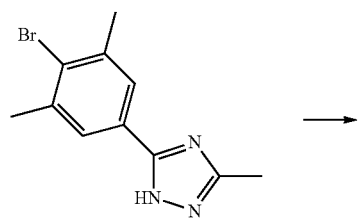

A mixture of Intermediate 78 (0.35 g), iodomethane (0.14 mL) and potassium hydroxide (85%, 0.087 g) in acetone (15 mL) are stirred for 16 h. Volatiles are removed under reduced pressure and the residue purified by chromatography (silica gel, cyclohexane/ethyl acetate 100:0 to 60:40) to give the title compound (0.27 g).

LC (LC METHOD 1): $t_R$=1.11 min; Mass spectrum (ES+): m/z=280/282 [M+H]$^+$.

Intermediate 81

3-(4-Bromo-3,5-dimethyl-phenyl)-1H-tetrazole

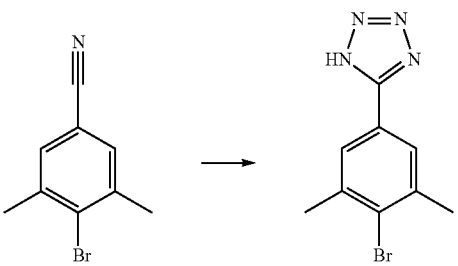

4-Bromo-3,5-dimethyl benzonitrile (3.0 g, 14.3 mmol), sodium azide (2.32 g, 35.7 mmol) and ammonium chloride (2.3 g, 42.84 mmol) are suspended in dry N,N-dimethylformamide and heated at 140° C. for 7 hours. The mixture is allowed to cool to room temperature, diluted with water and the precipitated solid collected by filtration, washed with water and dried to give the title compound (yield 1.74 g). The mother liquor was saturated with sodium chloride and repeatedly extracted with ethyl acetate. The organic extracts were combined and the solvent removed to give a second crop of title compound (yield 1.39 g, total yield 3.13 g).

LC (MIL__07__002): $t_R$=0.83 min; Mass spectrum (ES+): m/z=253/255 [M+H]$^+$.

Intermediate 82

1-[5-(4-Bromo-3,5-dimethyl-phenyl)-tetrazol-2-yl]-2-methyl-propan-2-ol

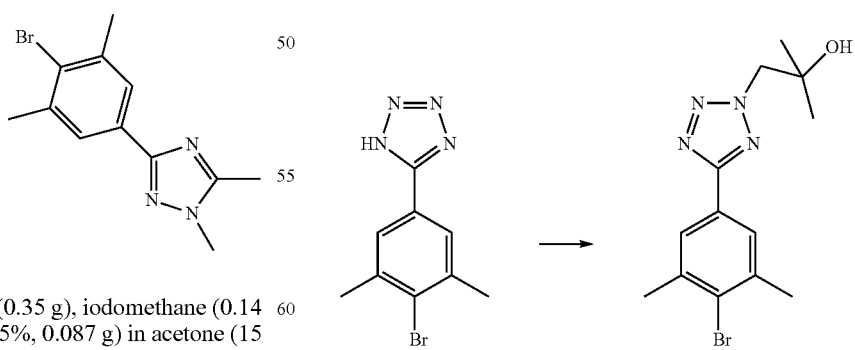

Intermediate 81 (400 mg, 1.58 mmol), cesium carbonate (103 mg, 0.32 mmol) and isobutylene oxide (2 mL) are placed in a microwave vial and heated under microwave irradiation at 100° C. for 1 hour. The residue is concentrated under vacuum and purified by flash chromatography (0-30% EtOAc in cyclohexane) to give the title compound (Yield 235 mg).

$^1$H NMR (500 MHz, d6 dmso) 1.20 (s, 6H), 2.46 (s, 6H), 4.63 (s, 2H), 4.92 (s, 1H), 7.86 (s, 2H).

Intermediates 83 and 84

5-(4-Bromo-3,5-dimethyl-phenyl)-1-methyl-tetrazole (Intermediate 83)

5-(4-Bromo-3,5-dimethyl-phenyl)-2-methyl-tetrazole (Intermediate 84)

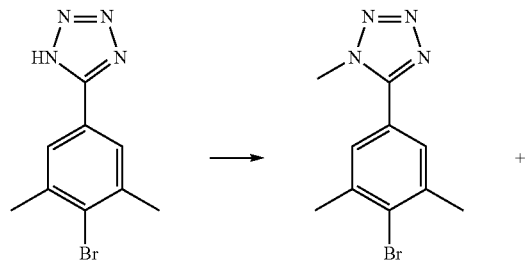

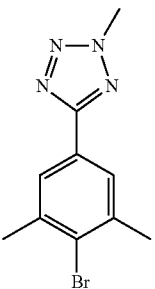

Intermediate 81 (1.7 g, 6.72 mmol), potassium hydroxide (942 mg, 16.79 mmol) and iodomethane (0.42 mL, 6.72 mmol) are suspended in N,N-dimethylformamide and stirred at room temperature for 4 hours. The mixture is diluted with water and extracted with dichloromethane. The organic phase is evaporated and the residue purified by flash chromatography (0-20% EtOAc in cyclohexane) to give 5-(4-Bromo-3,5-dimethyl-phenyl)-1-methyl-tetrazole (Intermediate 83, Yield 350 mg) and 5-(4-Bromo-3,5-dimethyl-phenyl)-2-methyl-tetrazole (Intermediate 84, Yield 1 g).

Intermediate 83:
$^1$H NMR (400 MHz, d6 dmso) 2.47 (s, 6H), 4.17 (s, 3H), 7.67 (s, 2H).

Intermediate 84:
$^1$H NMR (400 MHz, d6 dmso) 2.46 (s, 6H), 4.42 (s, 3H), 7.86 (s, 2H).

The Intermediates in the following table are prepared in analogy with the procedure used for the preparation of Intermediate 47 from the starting intermediates described:

TABLE 6

| Intermediate | Structure | Name | Starting intermediates | Yield | Analysis |
|---|---|---|---|---|---|
| 85 | (structure) | (1S,2S)-2-(4-{(R)-4-[4-(1,1-Dioxo-hexahydro-1-thiopyran-4-ylmethoxy)-2,6-dimethyl-phenyl]-7-fluoro-indan-1-yloxy}-phenyl)-cyclopropanecarboxylic acid ethyl ester | Intermediate 24 (200 mg) and intermediate 27 (156 mg) | 172 mg | LC (LC METHOD 1): $t_R$ = 1.46 min; Mass spectrum (ES+): m/z = 623 [M + H]$^+$. |

TABLE 6-continued

| Intermediate | Structure | Name | Starting intermediates | Yield | Analysis |
|---|---|---|---|---|---|
| 86 | 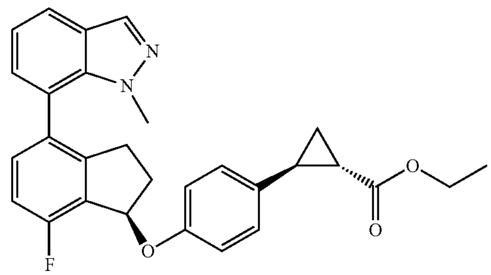 [SMILES: CCOC(=O)[C@H]1C[C@@H]1c1ccc(O[C@@H]2CCc3c(-c4cccc5cnn(C)c45)ccc(F)c32)cc1] | (1S,2S)-2-{4-[(R)-7-Fluoro-4-(1-methyl-1H-indazol-7-yl)-indan-1-yloxy]-phenyl}-cyclopropanecarboxylic acid ethyl ester | Intermediate 24 (150 mg) and 7-bromo-1-methyl-1H-indazole (65 mg) | 74 mg | LC (LC METHOD 1): $t_R$ = 1.57 min; Mass spectrum (ES+): m/z = 471 [M + H]+. |
| 87 | 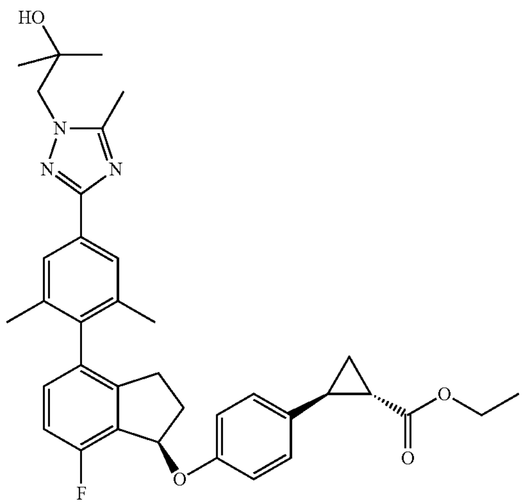 [SMILES: CCOC(=O)[C@H]1C[C@@H]1c1ccc(O[C@@H]2CCc3c(-c4c(C)cc(-c5nc(C)n(CC(C)(C)O)n5)cc4C)ccc(F)c32)cc1] | (1S,2S)-2-[4-((R)-7-Fluoro-4-{4-[1-(2-hydroxy-2-methyl-propyl)-5-methyl-1H-[1,2,4]triazol-3-yl]-2,6-dimethyl-phenyl}-indan-1-yloxy)-phenyl]-cyclopropane-carboxylic acid ethyl ester | Intermediate 24 (200 mg) and intermediate 79 (165 mg) | 300 mg (estimated content 60%) | LC (LC METHOD 1): $t_R$ = 1.44 min; Mass spectrum (ES+): m/z = 598 [M + H]+. |
| 88 | 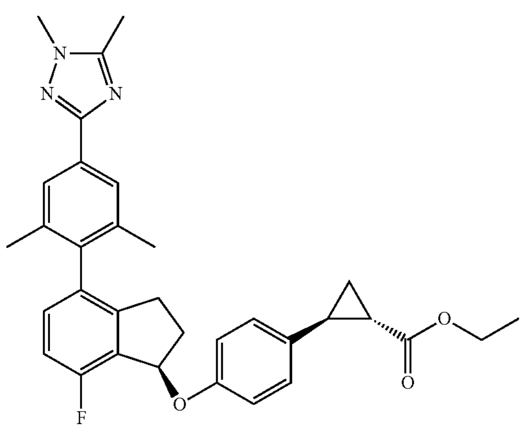 [SMILES: CCOC(=O)[C@H]1C[C@@H]1c1ccc(O[C@@H]2CCc3c(-c4c(C)cc(-c5nc(C)n(C)n5)cc4C)ccc(F)c32)cc1] | (1S,2S)-2-(4-{(R)-4-[4-(1,5-Dimethyl-1H-[1,2,4]triazol-3-yl)-2,6-dimethyl-phenyl]-7-fluoro-indan-1-yloxy}-phenyl)-cyclopropanecarboxylic acid ethyl ester | Intermediate 24 (200 mg) and intermediate 80 (144 mg) | 130 mg (estimated content 8%) | LC (LC METHOD 1): $t_R$ = 1.45 min; Mass spectrum (ES+): m/z = 540 [M + H]+. |

TABLE 6-continued

| Intermediate | Structure | Name | Starting intermediates | Yield | Analysis |
|---|---|---|---|---|---|
| 89 | 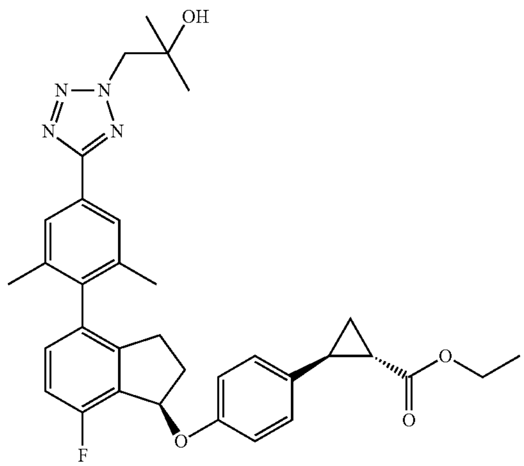 [SMILES: CCOC(=O)[C@H]1C[C@@H]1c1ccc(O[C@@H]2CCc3c(-c4c(C)cc(-c5nnn(CC(C)(C)O)n5)cc4C)ccc(F)c32)cc1] | (1S,2S)-2-[4-((R)-7-Fluoro-4-{4-[2-(2-hydroxy-2-methyl-propyl)-2H-tetrazol-5-yl]-2,6-dimethyl-phenyl}-indan-1-yloxy)-phenyl]-cyclopropanecarboxylic acid ethyl ester | Intermediate 24 (130 mg) and intermediate 82 (235 mg) | 95 mg | LC (LC METHOD 2): $t_R$ = 0.75 min; Mass spectrum (ES+): m/z = 585 [M + H]+. |
| 90 | 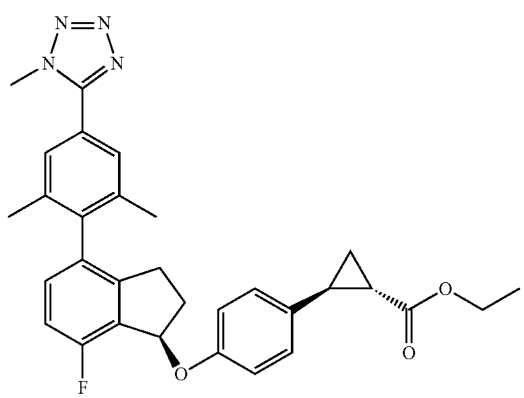 [SMILES: CCOC(=O)[C@H]1C[C@@H]1c1ccc(O[C@@H]2CCc3c(-c4c(C)cc(-c5nnnn5C)cc4C)ccc(F)c32)cc1] | (1S,2S)-2-(4-{(R)-4-[2,6-Dimethyl-4-(1-methyl-tetrazol-5-yl)-phenyl]-7-fluoro-indan-1-yloxy}-phenyl)-cyclopropanecarboxylic acid ethyl ester | Intermediate 24 (130 mg) and intermediate 83 (223 mg) | 80 mg | LC (LC METHOD 2): $t_R$ = 0.67 min; Mass spectrum (ES+): m/z = 527 [M + H]+. |
| 91 | 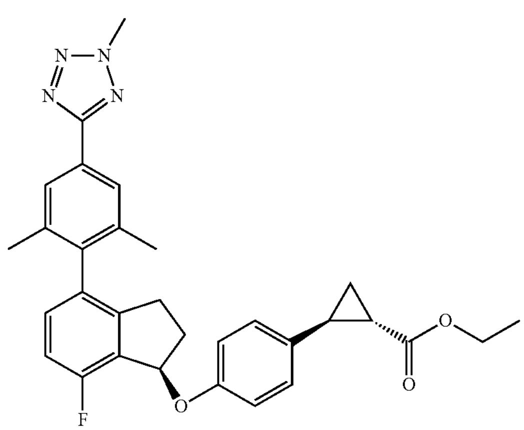 [SMILES: CCOC(=O)[C@H]1C[C@@H]1c1ccc(O[C@@H]2CCc3c(-c4c(C)cc(-c5nnn(C)n5)cc4C)ccc(F)c32)cc1] | (1S,2S)-2-(4-{(R)-4-[2,6-Dimethyl-4-(2-methyl-tetrazol-5-yl)-phenyl]-7-fluoro-indan-1-yloxy}-phenyl)-cyclopropanecarboxylic acid ethyl ester | Intermediate 24 (130 mg) and intermediate 84 (223 mg) | 80 mg | LC (LC METHOD 2): $t_R$ = 0.80 min; Mass spectrum (ES+): m/z = 527 [M + H]+. |

Intermediate 92

(1S,2S)-ethyl 2-(4-(((1R)-7-fluoro-4-(isoquinolin-4-yl)-2,3-dihydro-1H-inden-1-yloxy)phenyl)cyclopropanecarboxylate

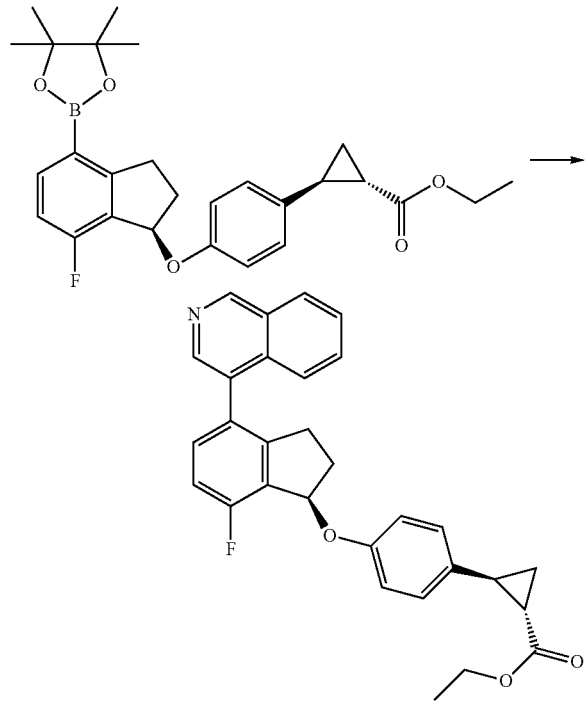

(1S,2S)-2-{4-[(R)-7-Fluoro-4-(4,4,5,5-tetramethyl-[1,3,2]dioxaborolan-2-yl)-indan-1-yloxy]-phenyl}-cyclopropanecarboxylic acid ethyl ester (Intermediate 24, 35 mg) is dissolved in a mixture of toluene (3 mL) and water (0.2 mL) and degassed with a flow of argon. 4-bromoisoquinoline (23.4 mg), tri-potassium phosphate (47.8 mg), 2-dicyclohexylphosphino-2',6'-dimethoxybiphenyl (S-Phos, 3.1 mg) and palladium (II) acetate (1.7 mg) are added and the mixture is heated at 100° C. for 7 hours and at 70° C. for 72 hours under argon. The reaction mixture is filtered over basic aluminium oxide and the filter material is washed with ethyl acetate. The organic phase is separated, concentrated and the crude product is purified by reversed phase chromatography to give the title compound (Yield 17.8 mg).

LC (LC METHOD 14): $t_R$=0.67 min; Mass spectrum (ES+): m/z=468.4 [M+H]$^+$.

The Intermediates in the following table are prepared in analogy with the procedure used for the preperation of intermediate 92 from the starting intermediates described:

TABLE 7

| Intermediate | Structure | Name | Starting intermediates | Yield | Analysis |
|---|---|---|---|---|---|
| 93 | 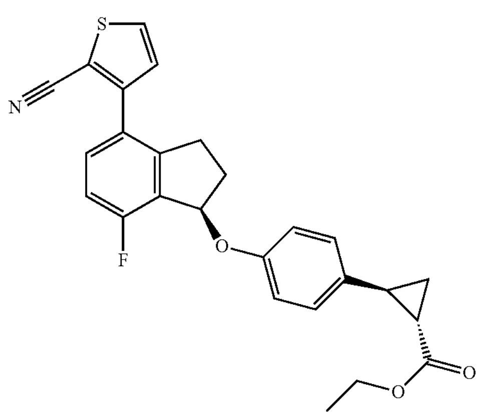 [SMILES: CCOC(=O)[C@H]1C[C@@H]1c1ccc(O[C@@H]2CCc3c(-c4ccsc4C#N)ccc(F)c32)cc1] | (1S,2S)-ethyl 2-(4-((1R)-4-(2-cyanothiophen-3-yl)-7-fluoro-2,3-dihydro-1H-inden-1-yloxy)-phenyl)cyclopropanecarboxylate | Intermediate 24 (35 mg) and 3-bromopthiophene-2-carbonitrile (21.2 mg) | 14.6 mg | LC (LC METHOD 14): $t_R$ = 0.91 min; Mass spectrum (ES+): m/z = 448.3 [M + H]$^+$. |

TABLE 7-continued

| Intermediate | Structure | Name | Starting intermediates | Yield | Analysis |
|---|---|---|---|---|---|
| 94 | 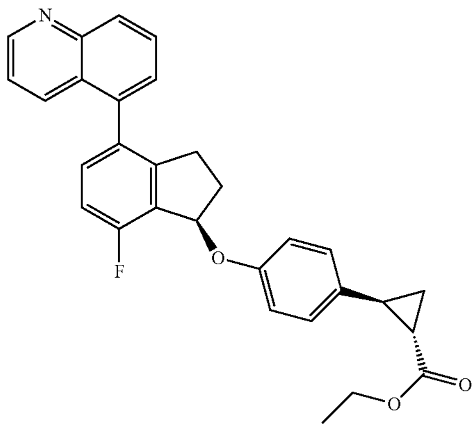 [SMILES: CCOC(=O)[C@H]1C[C@@H]1c1ccc(O[C@@H]2CCc3c(-c4cccc5ncccc45)ccc(F)c32)cc1] | (1S,2S)-ethyl 2-(4-((1R)-7-fluoro-4-(quinolin-5-yl)-2,3-dihydro-1H-inden-1-yloxy)phenyl)cyclopropanecarboxylate | Intermediate 24 (35 mg) and 5-bromoisoquinoline (23.4 mg) | 9.7 mg | LC (LC METHOD 15): $t_R$ = 1.06 min; Mass spectrum (ES+): m/z = 468.4 [M + H]$^+$. |
| 95 | 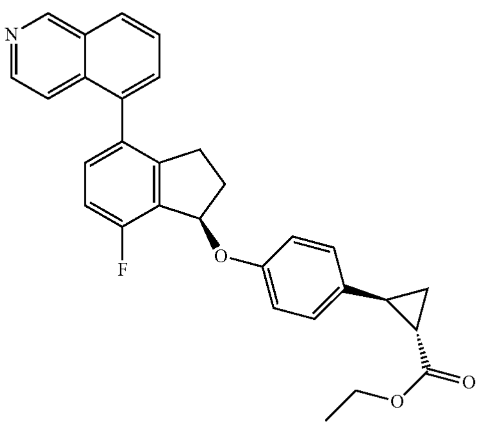 [SMILES: CCOC(=O)[C@H]1C[C@@H]1c1ccc(O[C@@H]2CCc3c(-c4cccc5cnccc45)ccc(F)c32)cc1] | (1S,2S)-ethyl 2-(4-((1R)-7-fluoro-4-(isoquinolin-5-yl)-2,3-dihydro-1H-inden-1-yloxy)phenyl)cyclopropanecarboxylate | Intermediate 24 (35 mg) and 5-bromoquinoline (23.4 mg) | 21.5 mg | LC (LC METHOD 15): $t_R$ = 1.13 min; Mass spectrum (ES+): m/z = 468.4 [M + H]$^+$. |
| 96 | 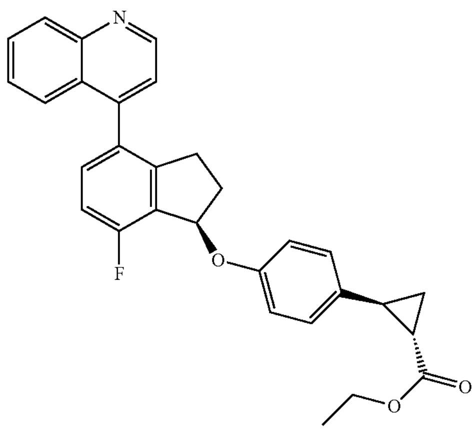 [SMILES: CCOC(=O)[C@H]1C[C@@H]1c1ccc(O[C@@H]2CCc3c(-c4ccnc5ccccc45)ccc(F)c32)cc1] | (1S,2S)-ethyl 2-(4-((1R)-7-fluoro-4-(quinolin-4-yl)-2,3-dihydro-1H-inden-1-yloxy)phenyl)cyclopropanecarboxylate | Intermediate 24 (35 mg) and 4-bromoquinoline (23.4 mg) | 4.5 mg | LC (LC METHOD 15): $t_R$ = 1.12 min; Mass spectrum (ES+): m/z = 468.4 [M + H]$^+$. |

Intermediate 97

(1S,2S)-ethyl 2-(4-((1R)-7-fluoro-4-(3-methoxypyridin-2-yl)-2,3-dihydro-1H-inden-1-yloxy)phenyl)cyclopropanecarboxylate

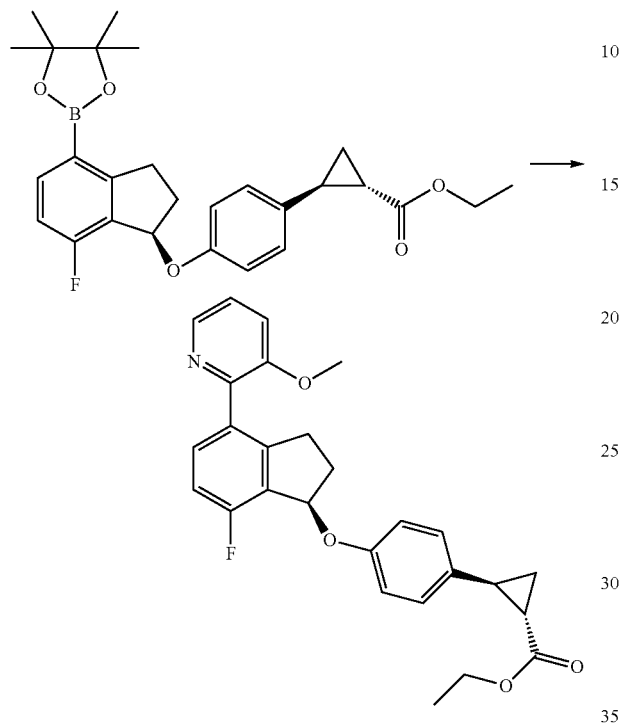

(1S,2S)-2-{4-[(R)-7-Fluoro-4-(4,4,5,5-tetramethyl-[1,3,2]dioxaborolan-2-yl)-indan-1-yloxy]-phenyl}-cyclopropanecarboxylic acid ethyl ester (Intermediate 24, 46.6 mg) and 2-bromo-3-methoxypyridine (28.2 mg) are dissolved N,N-dimethylformamide (1 mL) and degassed with a flow of argon. Aqueous 2M cesium carbonate solution (0.1 mL), 1,1'-bis(di-tert-butylphosphino)ferrocene palladium dichloride (6.5 mg, 0.1 equiv.) are added and the mixture is heated at 80° C. for 2.5 hours under argon. The reaction mixture is acidified with 50% aq. TFA, filtered over basic aluminium oxide and the filter material is washed with N,N-dimethylformamide. The crude product is purified by reversed phase chromatography to give the title compound (Yield 12.0 mg).

LC (LC METHOD 13): $t_R$=0.87 min; Mass spectrum (ES+): m/z=448.2 $[M+H]^+$.

The Intermediates in the following table are prepared in analogy with the procedure used for the preperation of Intermediate 97 from the starting intermediates described:

TABLE 8

| Intermediate | Structure | Name | Starting intermediates | Yield | Analysis |
|---|---|---|---|---|---|
| 98 | 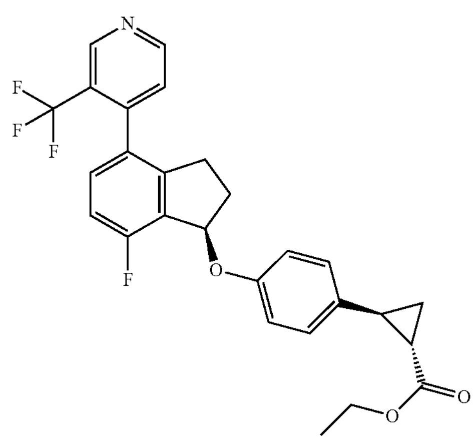 [SMILES: CCOC(=O)[C@H]1C[C@@H]1c1ccc(O[C@@H]2CCc3c(-c4ccncc4C(F)(F)F)ccc(F)c32)cc1] | (1S,2S)-ethyl 2-(4-((1R)-7-fluoro-4-(3-(trifluoromethyl)-pyridin-4-yl)-2,3-dihydro-1H-inden-1-yloxy)phenyl)cyclopropanecarboxylate | Intermediate 24 (46.6 mg) and 4-bromo-3-(trifluoromethyl)pyridine (33.9 mg) | 16.0 mg | LC (LC METHOD 13): $t_R$ = 1.1 min; Mass spectrum (ES+): m/z = 486.0 $[M + H]^+$. |

TABLE 8-continued

| Intermediate | Structure | Name | Starting intermediates | Yield | Analysis |
|---|---|---|---|---|---|
| 99 | 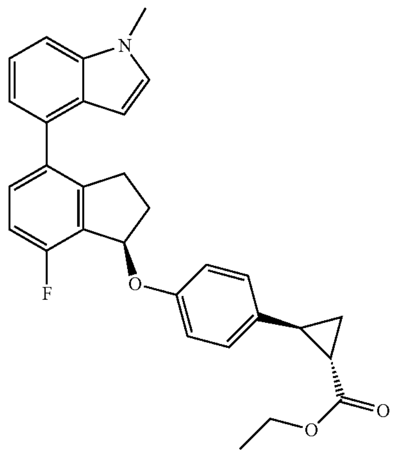 [SMILES: CCOC(=O)[C@H]1C[C@@H]1c1ccc(O[C@@H]2CCc3c(-c4cccc5c4ccn5C)ccc(F)c32)cc1] | (1S,2S)-ethyl 2-(4-((1R)-7-fluoro-4-(1-methyl-1H-indol-4-yl)-2,3-dihydro-1H-inden-1-yloxy)phenyl)cyclopropanecarboxylate | Intermediate 24 (46.6 mg) and 4-bromo-1-methyl-1H-indole (31.5 mg) | 6.7 mg | LC (LC METHOD 13): $t_R$ = 1.18 min; Mass spectrum (ES+): m/z = 470.0 [M + H]$^+$. |
| 100 | 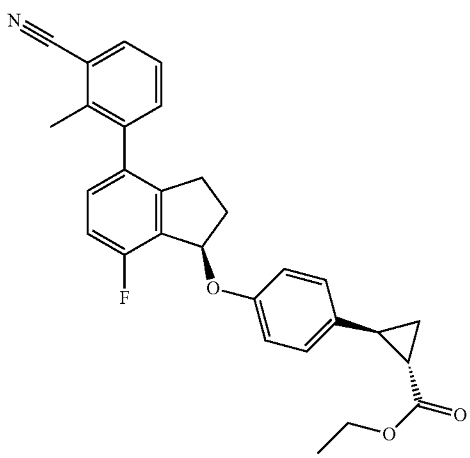 [SMILES: CCOC(=O)[C@H]1C[C@@H]1c1ccc(O[C@@H]2CCc3c(-c4cccc(C#N)c4C)ccc(F)c32)cc1] | (1S,2S)-ethyl 2-(4-((1R)-4-(3-cyano-2-methylphenyl)-7-fluoro-2,3-dihydro-1H-inden-1-yloxy)-phenyl)cyclopropanecarboxylate | Intermediate 24 (46.6 mg) and 3-bromo-2-methylbenzonitrile (29.4 mg) | 18.7 mg | LC (LC METHOD 13): $t_R$ = 1.16 min; Mass spectrum (ES+): m/z = 456.0 [M + H]$^+$. |
| 101 | 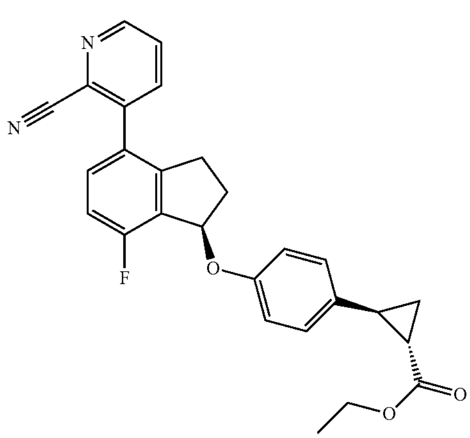 [SMILES: CCOC(=O)[C@H]1C[C@@H]1c1ccc(O[C@@H]2CCc3c(-c4cccnc4C#N)ccc(F)c32)cc1] | (1S,2S)-ethyl 2-(4-((1R)-4-(2-cyanopyridin-3-yl)-7-fluoro-2,3-dihydro-1H-inden-1-yloxy)-phenyl)cyclopropanecarboxylate | Intermediate 24 (46.6 mg) and 3-bromo-2-cyanopyridine (29.4 mg) | 28.4 mg | LC (LC METHOD 13): $t_R$ = 1.06 min; Mass spectrum (ES+): m/z = 443.0 [M + H]$^+$. |

TABLE 8-continued

| Intermediate | Structure | Name | Starting intermediates | Yield | Analysis |
|---|---|---|---|---|---|
| 102 | 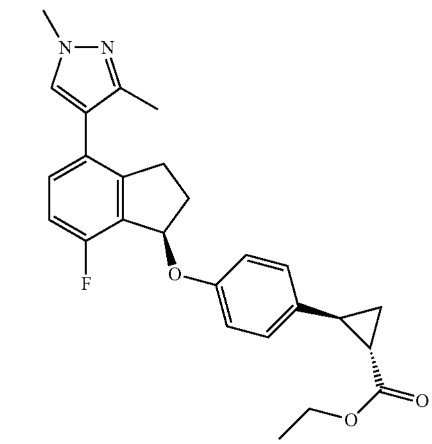 [SMILES: CCOC(=O)[C@H]1C[C@@H]1c1ccc(O[C@@H]2CCc3c(-c4cn(C)nc4C)ccc(F)c32)cc1] | (1S,2S)-ethyl 2-(4-((1R)-4-(1,3-dimethyl-1H-pyrazol-4-yl)-7-fluoro-2,3-dihydro-1H-inden-1-yloxy)phenyl)cyclopropane-carboxylate | Intermediate 24 (46.6 mg) and 4-bromo-1,3-dimethy1-1H-pyrazole (26.3 mg) | 16.6 mg | LC (LC METHOD 13): $t_R$ = 1.06 min; Mass spectrum (ES+): m/z = 435.2 [M + H]$^+$. |
| 103 | 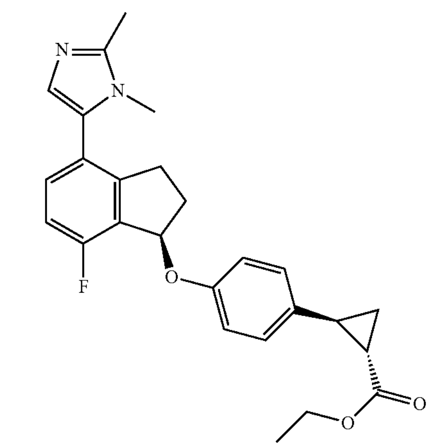 [SMILES: CCOC(=O)[C@H]1C[C@@H]1c1ccc(O[C@@H]2CCc3c(-c4cnc(C)n4C)ccc(F)c32)cc1] | (1S,2S)-ethyl 2-(4-((1R)-4-(1,2-dimethyl-1H-imidazol-5-yl)-7-fluoro-2,3-dihydro-1H-inden-1-yloxy)phenyl)cyclopropane-carboxylate | Intermediate 24 (46.6 mg) and 5-bromo-1,2-dimethyl-1H-imidazole (26.3 mg) | 9.1 mg | LC (LC METHOD 14): $t_R$ = 0.6 min; Mass spectrum (ES+): m/z = 435.4 [M + H]$^+$. |
| 104 | 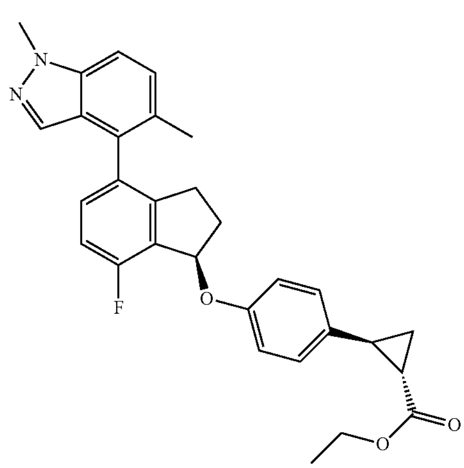 [SMILES: CCOC(=O)[C@H]1C[C@@H]1c1ccc(O[C@@H]2CCc3c(-c4c(C)ccc5c4cnn5C)ccc(F)c32)cc1] | (1S,2S)-ethyl 2-(4-((1R)-4-(1,5-dimethyl-1H-indazol-4-yl)-7-fluoro-2,3-dihydro-1H-inden-1-yloxy)phenyl)cyclopropane-carboxylate | Intermediate (46.6 mg) and 4-bromo-1,5-dimethyl-1H-indazole (33.8 mg) | 17.3 mg | LC (LC METHOD 13): $t_R$ = 1.15 min; Mass spectrum (ES+): m/z = 485.2 [M + H]$^+$. |

TABLE 8-continued

| Intermediate | Structure | Name | Starting intermediates | Yield | Analysis |
|---|---|---|---|---|---|
| 105 | 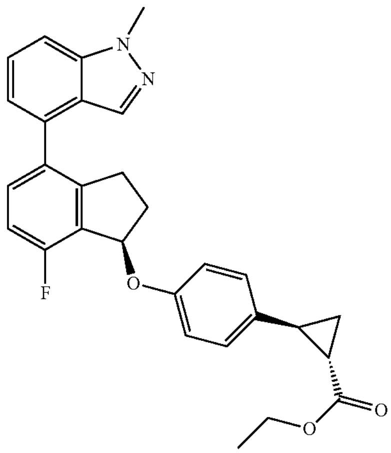 [SMILES: CCOC(=O)[C@H]1C[C@@H]1c1ccc(O[C@@H]2CCc3c(-c4cccc5c4cnn5C)ccc(F)c32)cc1] | (1S,2S)-ethyl 2-(4-((1R)-7-fluoro-4-(1-methyl-1H-indazol-4-yl-2,3-dihydro-1H-inden-1-yloxy)phenyl)cyclopropane-carboxylate | Intermediate 24 (46.6 mg) and 4-bromo-1-methyl-1H-indazole (31.6 mg) | 24.1 mg | LC (LC METHOD 13): $t_R$ = 1.13 min; Mass spectrum (ES+): m/z = 471 [M + H]+. |
| 106 | 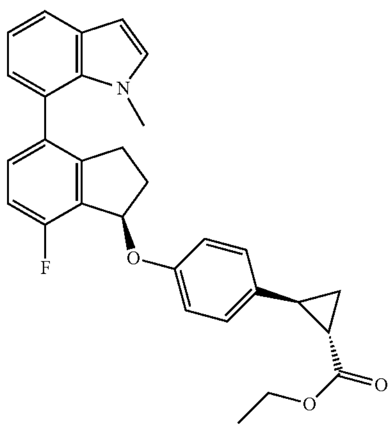 [SMILES: CCOC(=O)[C@H]1C[C@@H]1c1ccc(O[C@@H]2CCc3c(-c4cccc5ccn(C)c45)ccc(F)c32)cc1] | (1S,2S)-ethyl 2-(4-((1R)-7-fluoro-4-(1-methyl-1H-indol-7-yl)-2,3-dihydro-1H-inden-1-yloxy)phenyl)cyclopropane-carboxylate | Intermediate 24 (46.6 mg) and 7-bromo-1-methyl-1H-indole (31.5 mg) | 28.6 mg | LC (LC METHOD 13): $t_R$ = 1.19 min; Mass spectrum (ES+): m/z = 470 [M + H]+. |
| 107 | 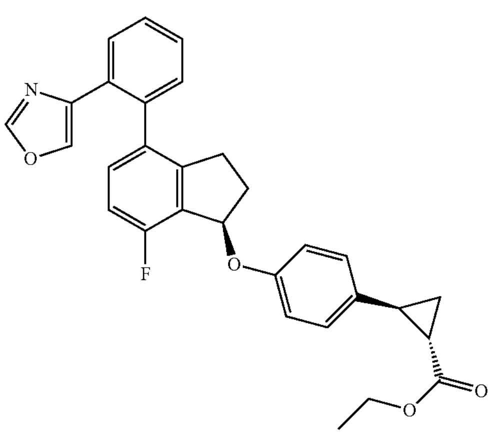 [SMILES: CCOC(=O)[C@H]1C[C@@H]1c1ccc(O[C@@H]2CCc3c(-c4ccccc4-c4cocn4)ccc(F)c32)cc1] | (1S,2S)-ethyl 2-(4-((1R)-7-fluoro-4-(2-(oxazol-4-yl)phenyl)-2,3-dihydro-1H-inden-1-yloxy)phenyl)cyclopropane-carboxylate | Intermediate 24 (46.6 mg) and 4-(2-Bromo-phenyl)-oxazole (33.6 mg) | 22.9 mg | LC (LC METHOD 14): $t_R$ = 0.93 min; Mass spectrum (ES+): m/z = 484.4 [M + H]+. |

TABLE 8-continued

| Intermediate | Structure | Name | Starting intermediates | Yield | Analysis |
|---|---|---|---|---|---|
| 108 | 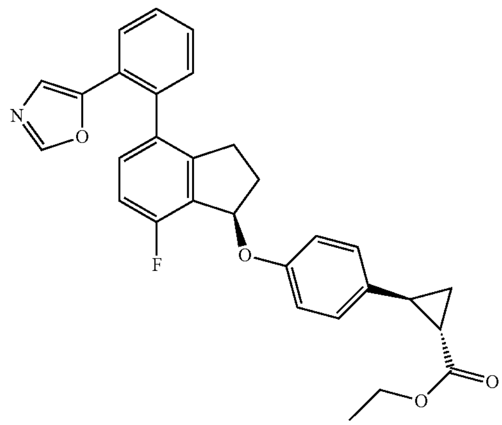 [SMILES: CCOC(=O)[C@H]1C[C@@H]1c1ccc(O[C@@H]2CCc3c(-c4ccccc4-c4cnco4)ccc(F)c32)cc1] | (1S,2S)-ethyl 2-(4-((1R)-7-fluoro-4-(2-(oxazol-5-yl)phenyl)-2,3-dihydro-1H-inden-1-yloxy)-phenyl)cyclopropanecarboxylate | Intermediate 24 (46.6 mg) and 5-(2-bromophenyl)-1,3-oxazole (33.6 mg) | 20.4 mg | LC (LC METHOD 13): $t_R$ = 1.15 min; Mass spectrum (ES+): m/z = 484.2 [M + H]$^+$. |

Intermediate 109

(S)-4-Bromo-5-trifluoromethyl-indan-1-ol

Note: Absolute stereochemistry assigned by analogy with Noyori et. al., J. Am. Chem. Soc., 1995, 117 (28), pp 7562-7563.

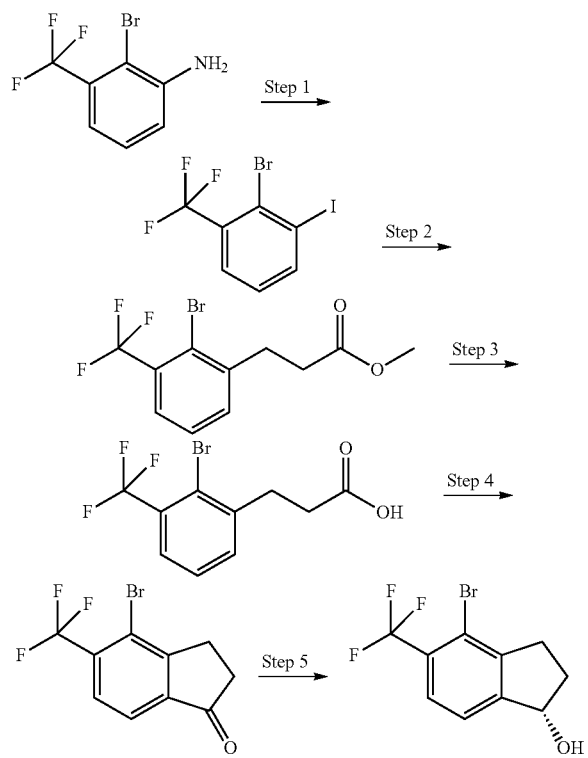

Step 1: 2-Bromo-3-trifluoromethyl-iodobenzene

2-Bromo-3-trifluoromethylaniline (8 g, 33.33 mmol) is suspended in water (90 mL) and cooled to 0° C. 96% $H_2SO_4$ (26.7 mL, 13.7 mmol) is added and the mixture stirred for 30 minutes. $NaNO_2$ (2.41 g, 35 mmol) is dissolved in a small quantity of water and added dropwise at 0° C. The mixture is stirred for 30 minutes then potassium iodide (9.24 g, 55.66 mmol) and iodine (9.31 g, 36.66 mmol) in water are added dropwise with cooling. The mixture is stirred until gas evolution ceases then warmed to 40° C. and allowed to cool to room temperature. The mixture is shaken with excess aqueous $Na_2SO_3$ solution and extracted with ethyl acetate. The organic extracts are evaporated and the residue purified by flash chromatography (eluent: cyclohexane) to give the title compound (Yield 10.0 g)

GC (GC METHOD 1): $t_R$=8.40 min; Mass spectrum (EI+): m/z=350 [M]$^+$.

Step 2: 3-(2-Bromo-3-trifluoromethyl-phenyl)-propionic acid methyl ester

2-Bromo-3-trifluoromethyl-iodobenzene (10 g, 28.5 mmol), acroleindimethyl acetal (8.73 mL, 85.5 mmol), tert-butylammonuim chloride (7.92 g, 28.5 mmol) and palladium (II) acetate (194 mg, 0.86 mmol) are combined in dry N,N-dimethylformamide under nitrogen and heated at 100° C. for 4 hours. The mixture is diluted with 1M HCl solution (100 mL) and extracted with diethyl ether. The organic extract is dried and concentrated under vacuum, the residue is purified by flash chromatography (eluent 1% EtOAc in cyclohexane) to give the title compound (yield 6.70 g).

GC (GC METHOD 1): $t_R$=9.69 min; Mass spectrum (EI+): m/z=279 [M–OMe]$^+$.

Step 3: 3-(2-Bromo-3-trifluoromethyl-phenyl)-propionic acid

2-Bromo-3-trifluoromethyl-phenyl)-propionic acid methyl ester is suspended in a mixture of methanol (25 mL), tetrahydrofuran (25 mL) and 32% sodium hydroxide (20.7 mL) and stirred overnight at room temperature. The solvent is removed, the mixture diluted with water and dichloromethane and the phases separated. The aqueous phase is acidified with 37% HCl solution and extracted with dichloromethane. The extracts are dried and the solvent removed to give the title compound (yield 6.0 g).

GC (GC METHOD 1): $t_R$=10.11 min; Mass spectrum (EI+): m/z=279 [M-OH]$^+$.

Step 4: 4-Bromo-5-trifluoromethyl-indan-1-one 3-(2-Bromo-3-trifluoromethyl-phenyl)-propionic acid (3.0 g, 10.1 mmol) is suspended in trifluoromethanesulfonic acid (30 mL)) under argon and heated at 85° C. for 4 hours. The mixture is added dropwise to iced water and then extracted with ethyl acetate. The organic extract is washed with saturated sodium bicarbonate solution, dried and concentrated under vacuum. The residue is purified by flash chromatography (Eluent 0-5% EtOAc in cyclohexane) to give the title compound.

GC (GC METHOD 1): $t_R$=9.49 min; Mass spectrum (EI+): m/z=278 [M]$^+$.

Step 5: (S)-4-Bromo-5-trifluoromethyl-indan-1-ol

Triethylamine (3.16 mL, 22.5 mmol) is dissolved in dichloromethane (40 mL) and cooled to 0° C. then formic acid (1.0 mL, 26.46 mmol) is added dropwise with cooling. After 20 minutes stirring 4-Bromo-5-trifluoromethyl-indan-1-one (2.1 g, 7.53 mmol) is added followed by Chloro([(1S,2S)-(–)-2-amino-1,2-diphenylethyl](4-toluenesulfonyl)amido)-(mesitylene)ruthenium(II) complex (220 mg, 0.35 mmol) and the mixture is stirred overnight under argon at room temperature. Water is added, the mixture shaken and the phases separated. The organic phase is dried and concentrated under vacuum. The residue is purified by flash chromatography (0-15% ethyl acetate in cyclohexane) to give the title compound (yield 2.0 g).

GC (GC METHOD 1): $t_R$=9.82 min; Mass spectrum (EI+): m/z=280 [M]$^+$.

Intermediate 110

(1S,2S)-2-[4-((R)-4-Bromo-5-trifluoromethyl-indan-1-yloxy)-phenyl]-cyclopropanecarboxylic acid ethyl ester

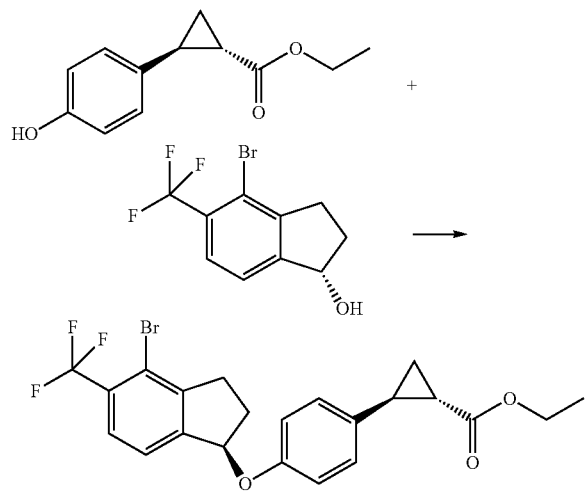

The title compound is prepared from intermediate 4 (242 mg) and intermediate 109 (300 mg) following a procedure analogous to that described for the preperation of intermediate 11 (yield 290 mg).

LC (LC METHOD 2): $t_R$=0.90 min; Mass spectrum (ES+): m/z=469/471 [M+H]$^+$.

Intermediate 111

(1S,2S)-2-(4-{(R)-4-[4-(4-Hydroxy-tetrahydro-pyran-4-ylmethoxy)-phenyl]-5-trifluoromethyl-indan-1-yloxy}-phenyl)-cyclopropanecarboxylic acid ethyl ester

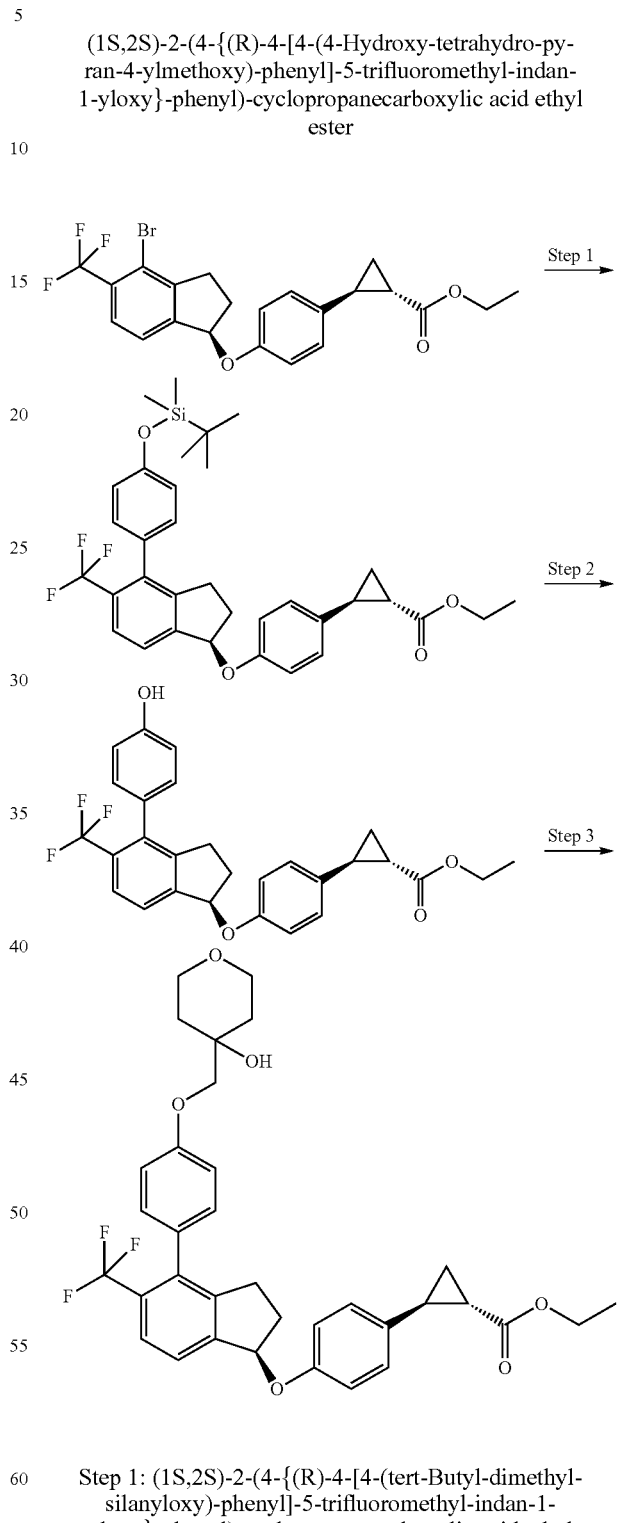

Step 1: (1S,2S)-2-(4-{(R)-4-[4-(tert-Butyl-dimethyl-silanyloxy)-phenyl]-5-trifluoromethyl-indan-1-yloxy}-phenyl)-cyclopropanecarboxylic acid ethyl ester (1S,2S)-2-[4-((R)-4-Bromo-5-trifluoromethyl-indan-1-yloxy)-phenyl]-cyclopropanecarboxylic acid ethyl ester (200 mg, 0.43 mmol), 4-(tertbutyldimethylsilyloxy)phenylboronic acid (118 mg, 0.47 mmol) potassium carbonate (176 mg, 1.28 mmol), 2,6-di-tert-butyl-4-methylphenol (47 mg, 0.21 mmol), tricyclohexylphosphine (10 mg, 0.03 mmol), and $Pd_2(dba)_3$ (16 mg, 0.02 mmol) are suspended in a mixture of dioxane (1.7 mL) and water (0.6 mL) in a sealed tube and heated at 110° C. for 4 hours. The mixture is diluted with saturated ammonium chloride solution and extracted with ethyl acetate. The organic phase is dried and concentrated under vacuum. The residue is purified by flash chromatography (eluent: 0-30% EtOAc in cyclohexane) to give the title compound (Yield 90 mg)

LC (LC METHOD 4): $t_R$=9.94 min; Mass spectrum (ES+): =597 $[M+H]^+$.

Step 2: ((1S,2S)-2-{4-[(R)-4-(4-Hydroxy-phenyl)-5-trifluoromethyl-indan-1-yloxy]-phenyl}-cyclopropanecarboxylic acid ethyl ester (1S,2S)-2-(4-{(R)-4-[4-(tert-Butyl-dimethyl-silanyloxy)-phenyl]-5-trifluoromethyl-indan-1-yloxy}-phenyl)-cyclopropanecarboxylic acid ethyl ester (90 mg, 0.15 mmol is suspended in dry tetrahydrofuran (4.5 mL) and tetrabutylammonium fluoride (1 M in tetrahydrofuran, 0.3 mL, 0.3 mmol) is added. The mixture stirred for 2 hours then diluted with saturated ammonium chloride solution and extracted with ethyl acetate. The organic phase is dried and concentrated under vacuum. The residue is purified by flash chromatography (eluent: 0-20% EtOAc in cyclohexane) to give an impure product which is used directly in the next step.

Step 3: (1S,2S)-2-(4-{(R)-4-[4-(4-Hydroxy-tetrahydro-pyran-4-ylmethoxy)-phenyl]-5-trifluoromethyl-indan-1-yloxy}-phenyl)-cyclopropanecarboxylic acid ethyl ester ((1S,2S)-2-{4-[(R)-4-(4-Hydroxy-phenyl)-5-trifluoromethyl-indan-1-yloxy]-phenyl}-cyclopro-panecarboxylic acid ethyl ester (crude from step 2), 1,6-dioxa-spiro[2.5]octane (US2012/46304, 44 mg) and cesium carbonate (198 mg) are suspended in dry N,N-dimethylformamide and heated at 100° C. for 3 hours. The mixture is diluted with water, acidified with 0.2 M HCl solution and extracted with ethyl acetate. The combined organic extracts are concentrated under vacuum and the residue purified by flash chromatography (0-30% EtOAc in cyclohexane) ti give the title compound (yield 50 mg).

LC (LC METHOD 11): $t_R$=4.52 min; Mass spectrum (ES+): m/z=597 $[M+H]^+$.

Intermediate 112

(1S,2S)-2-(4-{(R)-4-[4-(5-Methyl-[1,2,4]oxadiazol-3-yl)-phenyl]-5-trifluoromethyl-indan-1-yloxy}-phenyl)-cyclopropanecarboxylic acid ethyl ester

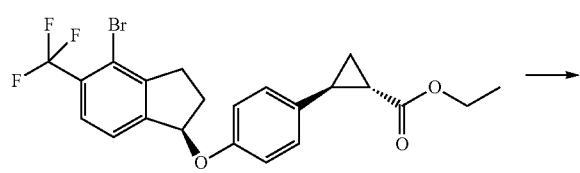

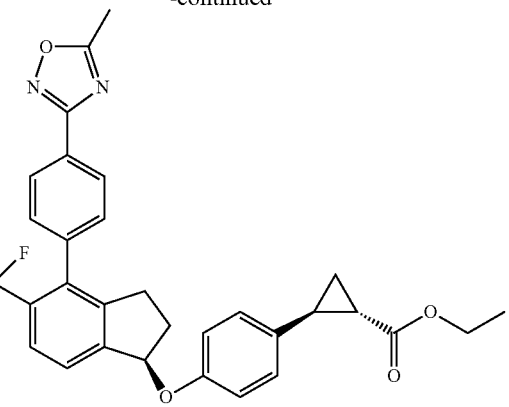

Intermediate 110 (90 mg, 0.19 mmol) is treated with 5-methyl-3-[4-(4,4,5,5-tetramethyl-[1,3,2]dioxaborolan-2-yl)-phenyl]-[1,2,4]oxadiazole (71 mg, 0.25 mmol) in conditions analogous to those described for intermediate 111 step 1 to give the title compound (50 mg)

LC (LC METHOD 2): $t_R$=0.86 min; Mass spectrum (ES+): m/z=549 $[M+H]^+$.

Synthesis of Examples

Method A:

The ester intermediate is dissolved in a mixture of tetrahydrofuran (5 mL) and methanol (5 mL) and aqueous sodium hydroxide solution (1 M, 1-3 equivalents) is added. The mixture is stirred overnight then concentrated under vacuum, acidified with 1 M hydrochloric acid and extracted with ethyl acetate. The organic extracts are washed with water and brine, dried and the solvent removed. If necessary the residue is purified by flash chromatography (0-50% ethyl acetate in cyclohexane or 0-10% methanol in dichloromethane) to give the title compound.

Method B:

The ester intermediate is dissolved in methanol or ethanol (5 mL) and aqueous sodium hydroxide solution (1 M, 1-5 equivalents) is added. The mixture is stirred overnight then concentrated under vacuum, acidified with 1 M hydrochloric acid and extracted with ethyl acetate. The organic extracts are washed with water and brine, dried and the solvent removed. If necessary the residue is purified by flash chromatography (0-50% ethyl acetate in cyclohexane or 0-10% methanol in dichloromethane) to give the title compound.

Method C:

The ester intermediate is dissolved in a mixture of tetrahydrofuran (5 mL) and methanol (5 mL) and water (5 mL) and lithium hydroxide monohydrate (1-3 equivalents) is added. The mixture is stirred overnight then concentrated under vacuum, acidified with 1 M hydrochloric acid and extracted with ethyl acetate. The organic extracts are washed with water and brine, dried and the solvent removed. If necessary the residue is purified by flash chromatography (0-50% ethyl acetate in cyclohexane or 0-10% methanol in dichloromethane) to give the title compound.

Method D:

The ester intermediate is dissolved in a mixture of ethanol (5 mL) and water (1 mL) and lithium hydroxide monohydrate (1-3 equivalents) is added. The mixture is stirred overnight then concentrated under vacuum, acidified with aqueous citric acid solution and extracted with ethyl acetate. The organic extracts are washed with water and brine, dried and the solvent removed. If necessary the residue is purified by flash chromatography (0-50% ethyl acetate in cyclohexane or 0-10% methanol in dichloromethane) to give the title compound.

Method E:

The ester intermediate in a mixture of tetrahydrofuran and water (4:1) is treated with lithium hydroxide monohydrate (5 equivalents). After 2 hours volatiles are evaporated in vacuo, the residue partitioned between $CH_2Cl_2$ and aqueous HCl (1 M), the organic phase collected, concentrated and purified on a PoraPak Rxn RP cartridge, eluting with a water to acetonitrile gradient to give the title compound.

Method F:

The ester intermediate is dissolved in $^iPrOH$ (7 mL) and aqueous sodium hydroxide solution (1 M, 2 mL) is added. The mixture is stirred overnight, acidified with saturated aqueous citric acid and extracted with $Et_2O$. The organic extracts are washed with brine, dried and the solvent removed. If necessary the residue is purified by flash chromatography (0-50% ethyl acetate in cyclohexane or 0-20% methanol in dichloromethane) to give the title compound.

Method G:

The ester intermediate in dioxane (5 mL) is treated with lithium hydroxide monohydrate (3 equivalents) in water (0.2 mL). After 20 hours excess HCl (1 M) is added at 0° C. and the mixture is extracted with diethyl ether. Solvents are removed from the organic extracts and the residue purified by chromatography as appropriate to give the title compound.

Method H:

The ester intermediate is suspended in tetrahydrofuran (2 mL) and treated with aqueous sodium hydroxide solution (2.7 equivalents) at room temperature overnight. Additional sodium hydroxide solution (2.7 equivalents) is added and the solution is stirred at 40° C. for 2 hours. The solution is acidified with 1 M hydrochloric acid, evaporated and purified by reversed phase chromatography to give the title compound.

Method I:

The ester intermediate is suspended in mixture of tetrahydrofuran and methanol (2 mL, 1:1) and treated with aqueous lithium hydroxide solution (2.5 mmol) at room temperature overnight. The solution is acidified with 4 M hydrochloric acid, evaporated and purified by reversed phase chromatography to give the title compound.

Method J:

The ester intermediate is dissolved in a mixture of dioxane (1 mL) and methanol (1 mL) and aqueous sodium hydroxide solution (1 M, 12 equivalents) is added. The mixture is stirred overnight then concentrated under vacuum, acidified with citric acid and extracted with dichloromethane. The organic extracts are washed with water and brine, dried and the solvent removed. The residue is purified by flash chromatography (0-30% ethyl acetate in cyclohexane) followed by reverse phase chromatography to give the title compound.

The Examples in the following table are prepared according to method A, B, C, D, E, F, G, H, I or J described above from the corresponding ester intermediates:

TABLE 9

| Example | Structure | Name | Ester intermediate | Method | Yield | Analysis |
|---|---|---|---|---|---|---|
| 1 | 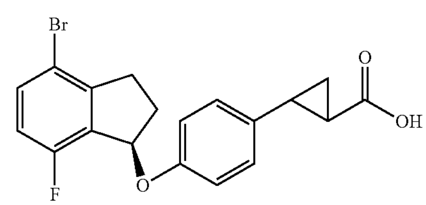 [SMILES: O=C(O)C1CC1c1ccc(O[C@@H]2CCc3c(Br)ccc(F)c32)cc1] | 2-[4-((R)-4-Bromo-7-fluoro-indan-1-yloxy)-2-methoxy-phenyl]-trans-cyclopropane-carboxylic acid | 14 (127 mg) | A | 60 mg | LC (LC METHOD 4): $t_R$ = 6.81 min; Mass spectrum (ES-): m/z = 389 [M − H]$^-$. |
| 2 | 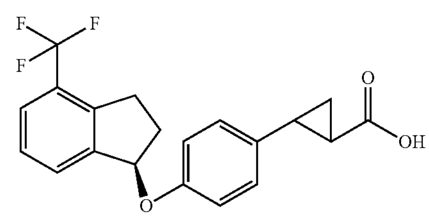 [SMILES: O=C(O)C1CC1c1ccc(O[C@@H]2CCc3c2cccc3C(F)(F)F)cc1] | 2-[4-((R)-4-Trifluoromethyl-indan-1-yloxy)-phenyl]-trans-cyclopropanecarboxylic acid | 15 (40 mg) | A | 24 mg | LC (LC METHOD 4): $t_R$ = 7.11 min; Mass spectrum (ES-): m/z = 361 [M − H]$^-$. |
| 3 | 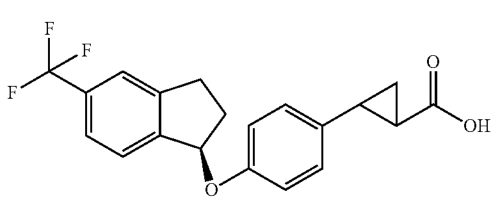 [SMILES: O=C(O)C1CC1c1ccc(O[C@@H]2CCc3cc(C(F)(F)F)ccc32)cc1] | 2-[4-((R)-5-Trifluoromethyl-indan-1-yloxy)-phenyl]-trans-cyclopropanecarboxylic acid | 16 (124 mg) | A | 64 mg | LC (LC METHOD 4): $t_R$ = 6.91 min; Mass spectrum (ES-): m/z = 361 [M − H]$^-$. |

TABLE 9-continued

| Example | Structure | Name | Ester intermediate | Method | Yield | Analysis |
|---|---|---|---|---|---|---|
| 4 | 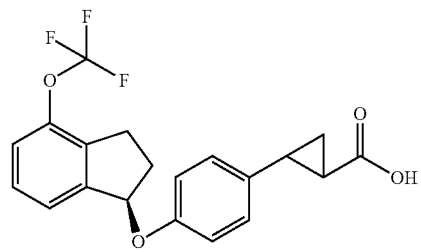 [SMILES: O=C(O)C1CC1c1ccc(O[C@@H]2CCc3c(OC(F)(F)F)cccc32)cc1] | 2-[4-((R)-4-Trifluoromethoxy-indan-1-yloxy)-phenyl]-trans-cyclopropanecarboxylic acid | 17 (55 mg) | B | 45 mg | LC (LC METHOD 4): $t_R$ = 7.14 min; Mass spectrum (ES−): m/z = 377 [M − H]−. |
| 5 | 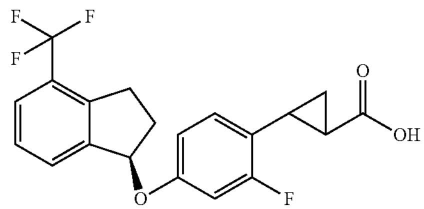 [SMILES: O=C(O)C1CC1c1ccc(O[C@@H]2CCc3c2cccc3C(F)(F)F)cc1F] | 2-[4-((R)-4-Trifluoromethyl-indan-1-yloxy)-2-fluorophenyl]-trans-cyclopropanecarboxylic acid | 18 (31 mg) | B | 22 mg | LC (LC METHOD 4): $t_R$ = 7.21 min; Mass spectrum (ES+): m/z = 381 [M + H]+. |
| 6 | 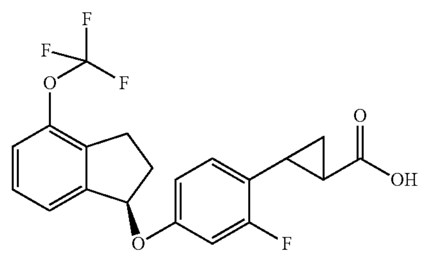 [SMILES: O=C(O)C1CC1c1ccc(O[C@@H]2CCc3c(OC(F)(F)F)cccc32)cc1F] | 2-[4-((R)-4-Trifluoromethoxy-indan-1-yloxy)-2-fluorophenyl]-trans-cyclopropanecarboxylic acid | 19 (50 mg) | C | 48 mg | LC (LC METHOD 4): $t_R$ = 6.77 min; Mass spectrum (ES−): m/z = 395 [M − H]−. |
| 7 | 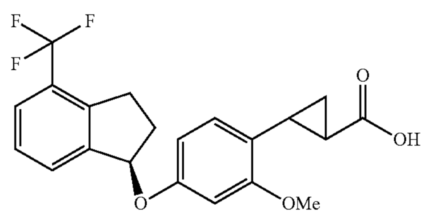 [SMILES: COc1cc(O[C@@H]2CCc3c2cccc3C(F)(F)F)ccc1C1CC1C(=O)O] | 2-[4-((R)-4-Trifluoromethyl-indan-1-yloxy)-2-methoxyphenyl]-trans-cyclopropanecarboxylic acid | 20 (50 mg) | D | 37 mg | LC (LC METHOD 4): $t_R$ = 7.20 min; Mass spectrum (ES−): m/z = 391 [M − H]−. |
| 8 | 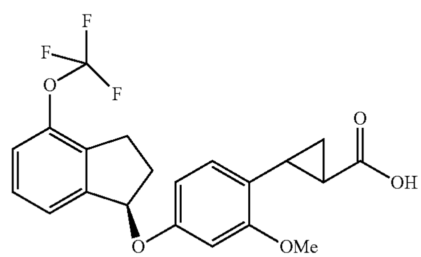 [SMILES: COc1cc(O[C@@H]2CCc3c(OC(F)(F)F)cccc32)ccc1C1CC1C(=O)O] | 2-[4-((R)-4-Trifluoromethoxy-indan-1-yloxy)-2-methoxy-phenyl]-trans-cyclopropanecarboxylic acid | 21 (50 mg) | D | 43 mg | LC (LC METHOD 4): $t_R$ = 7.33 min; Mass spectrum (ES−): m/z = 407 [M − H]−. |
| 9 | 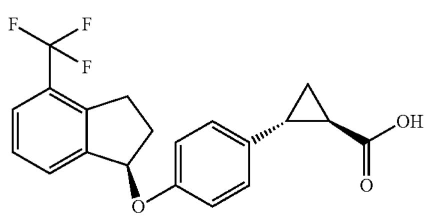 [SMILES: O=C(O)[C@@H]1C[C@H]1c1ccc(O[C@@H]2CCc3c2cccc3C(F)(F)F)cc1] | (1R,2R)-2-[4-((R)-4-Trifluoromethyl-indan-1-yloxy)-phenyl]-cyclopropanecarboxylic acid | 22 (166 mg) | D | 143 mg | LC (LC METHOD 4): $t_R$ = 6.63 min; Mass spectrum (ES−): m/z = 361 [M − H]− e.e. 100% by chiral HPLC |

TABLE 9-continued

| Example | Structure | Name | Ester intermediate | Method | Yield | Analysis |
|---|---|---|---|---|---|---|
| 10 | 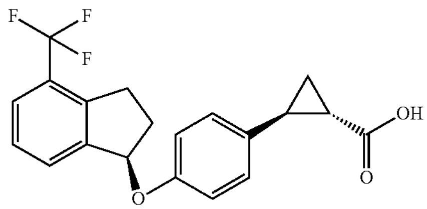 [SMILES: O=C(O)[C@H]1C[C@@H]1c1ccc(O[C@@H]2CCc3c2cccc3C(F)(F)F)cc1] | (1S,2S)-2-[4-((R)- 4-Trifluoro-methyl-indan-1-yloxy)-phenyl]-cyclopropanecarboxylic acid | 23 (166 mg) | D | 130 mg | LC (LC METHOD 4): $t_R$ = 6.65 min; Mass spectrum (ES−): m/z = 361 [M − H]⁻ e.e. 100% by chiral HPLC |
| 11 | 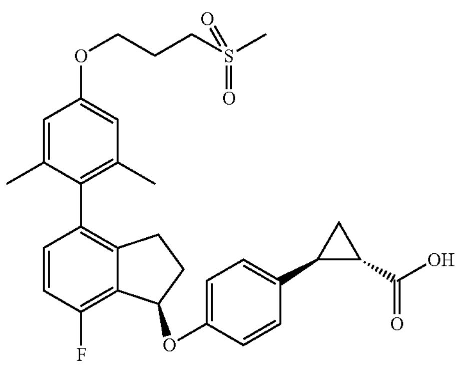 [SMILES: Cc1cc(OCCCS(C)(=O)=O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(3-methanesulfonyl-pro-poxy)-2,6-dimethyl-phenyl]-indan-1-yloxy}-phenyl)-cyclopropanecarboxylic acid | 47 (308 mg) | C | 166 mg | LC (LC METHOD 4): $t_R$ = 6.75 min; Mass spectrum (ES−): m/z = 551 [M − H]⁻. e.e. >95% by chiral HPLC |
| 12 | 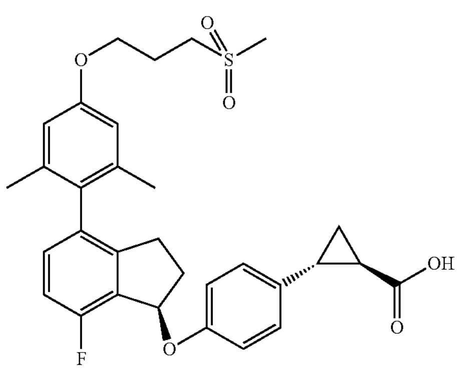 [SMILES: Cc1cc(OCCCS(C)(=O)=O)cc(C)c1-c1ccc(F)c2c1CC[C@H]2Oc1ccc([C@@H]2C[C@H]2C(=O)O)cc1] | (1R,2R)-2-(4-{(R)-7-Fluoro-4-[4-(3-methanesulfonyl-propoxy)-2,6-dimethyl-phenyl]-indan-1-yloxy}-phenyl)-cyclopropanecarboxylic acid | 48 (960 mg) | C | 280 mg | LC (LC METHOD 4): $t_R$ = 6.78 min; Mass spectrum (ES−): m/z = 551 [M − H]⁻. e.e. >95% by chiral HPLC |
| 13 | 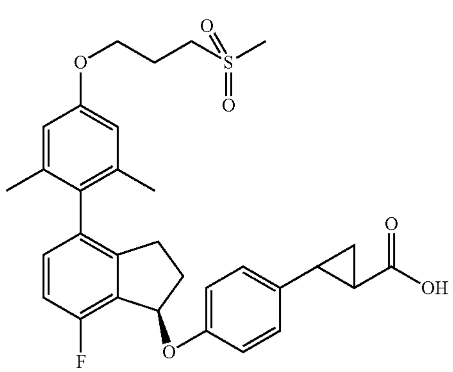 [SMILES: Cc1cc(OCCCS(C)(=O)=O)cc(C)c1-c1ccc(F)c2c1CC[C@H]2Oc1ccc(C2CC2C(=O)O)cc1] | 2-(4-{(R)-7-Fluoro-4-[4-(3-methanesulfonyl-propoxy)-2,6-dimethyl-phenyn-indan-1-yloxy}-phenyl)-trans-cyclopropanecarboxylic acid | 49 (24 mg) | D | 22 mg | LC (LC METHOD 4): $t_R$ = 6.32 min; Mass spectrum (ES−): m/z = 551 [M − H]. |

TABLE 9-continued

| Example | Structure | Name | Ester intermediate | Method | Yield | Analysis |
|---|---|---|---|---|---|---|
| 14 | 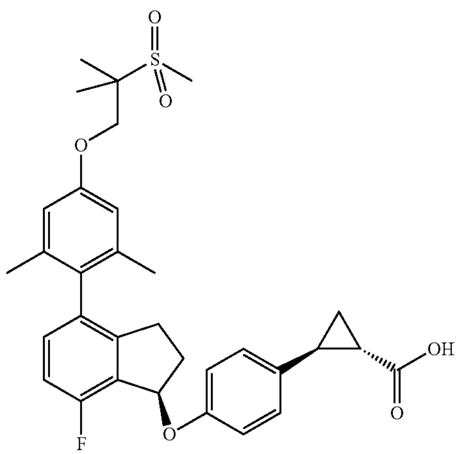 [SMILES: Cc1cc(OCC(C)(C)S(C)(=O)=O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(2-methanesulfonyl-2-methyl-propoxy)-2,6-dimethyl-phenyl]-indan-1-yloxy}-phenyl)-cyclopropanecarboxylic acid | 50 (96 mg) | C | 81 mg | LC (LC METHOD 4): $t_R$ = 7.05 min; Mass spectrum (ES−): m/z = 565 [M − H]⁻. |
| 15 | 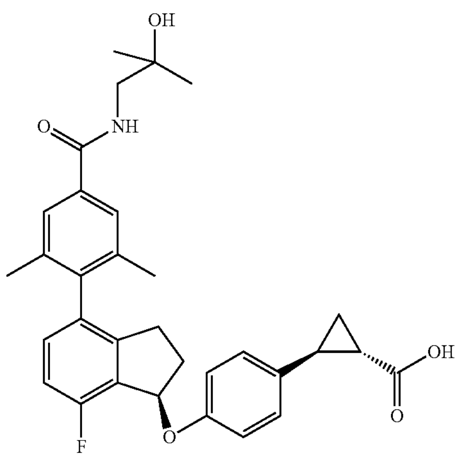 [SMILES: Cc1cc(C(=O)NCC(C)(C)O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(2-hydroxy-2-methyl-propylcarbamoyl)-2,6-dimethyl-phenyl]-indan-1-yloxy}-phenyl)-cyclopropanecarboxylic acid | 51 (35 mg) | D | 25 mg | LC (LC METHOD 4): $t_R$ = 6.13 min; Mass spectrum (ES+): m/z = 532 [M + H]⁺. |
| 16 | 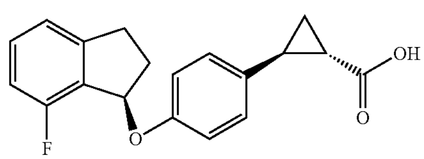 [SMILES: O=C(O)[C@H]1C[C@@H]1c1ccc(O[C@@H]2CCc3cccc(F)c32)cc1] | (1S,2S)-2-[4-((R)-7-Fluoro-indan-1-yloxy)-phenyl]-cyclopropanecarboxylic acid | 52 (45 mg) | B | 27 mg | LC (LC METHOD 4): $t_R$ = 6.12 min; Mass spectrum (ES+): m/z = 311 [M + H]⁺. |
| 17 | 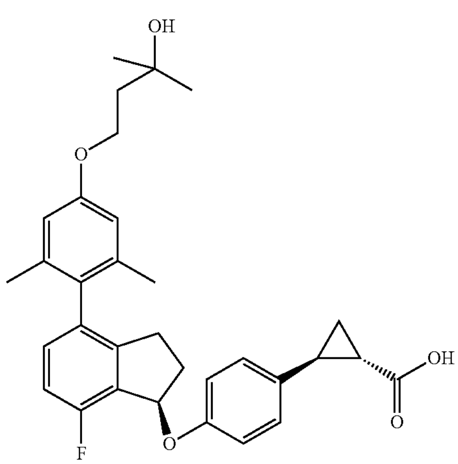 [SMILES: Cc1cc(OCCC(C)(C)O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(3-hydroxy-3-methyl-butoxy)-2,6-dimethyl-phenyl]-indan-1-yloxy}-phenyl)-cyclopropanecarboxylic acid | 53 (30 mg) | D | 25 mg | LC (LC METHOD 4): $t_R$ = 7.41 min; Mass spectrum (ES−): m/z = 517 [M − H]⁻. |

TABLE 9-continued

| Example | Structure | Name | Ester intermediate | Method | Yield | Analysis |
|---|---|---|---|---|---|---|
| 18 | 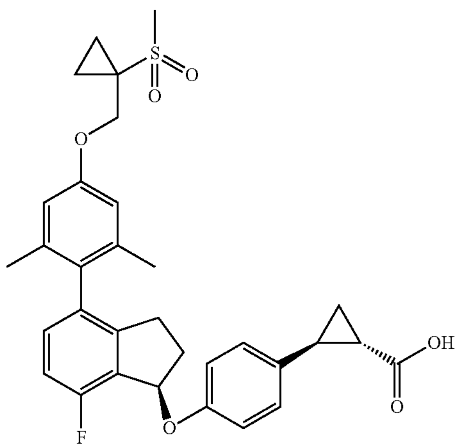 [SMILES: Cc1cc(OCC2(S(C)(=O)=O)CC2)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(1-methanesulfonyl-cyclopropylmethoxy)-2,6-dimethyl-phenyl]-indan-1-yloxy}-phenyl)-cyclopropane-carboxylic acid | 54 (80 mg) | C | 71 mg | LC (LC METHOD 4): $t_R$ = 7.18 min; Mass spectrum (ES−): m/z = 563 [M − H]−. |
| 19 | 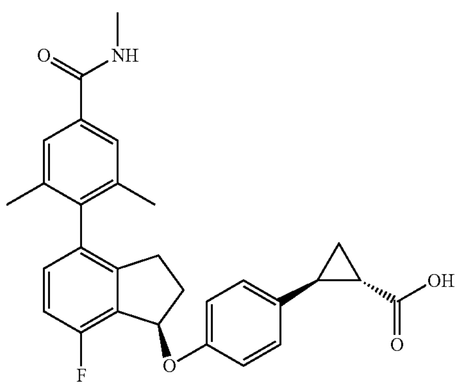 [SMILES: CNC(=O)c1cc(C)c(-c2ccc(F)c3c2CC[C@H]3Oc2ccc([C@H]3C[C@@H]3C(=O)O)cc2)c(C)c1] | (1S,2S)-2-{4-[(R)-4-(2,6-Dimethyl-4-methylcarbamoyl-phenyl)-7-fluoro-indan-1-yloxy]-phenyl}-cyclopropane-carboxylic acid | 55 (40 mg) | D | 25 mg | LC (LC METHOD 4): $t_R$ = 6.23 min; Mass spectrum (ES+): m/z = 474 [M + H]+. |
| 20 | 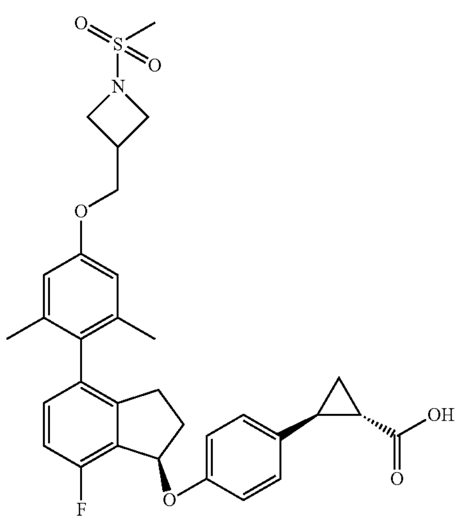 [SMILES: Cc1cc(OCC2CN(S(C)(=O)=O)C2)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(1-methanesulfonyl-azetidin-3-ylmethoxy)-2,6-dimethyl-phenyl]-indan-1-yloxy}-phenyl)-cyclopropanecarboxylic acid | 56 (131 mg) | C | 50 mg | LC (LC METHOD 4): $t_R$ = 7.13 min; Mass spectrum (ES+): m/z = 580 [M + H]+. |

TABLE 9-continued

| Example | Structure | Name | Ester intermediate | Method | Yield | Analysis |
|---|---|---|---|---|---|---|
| 21 | 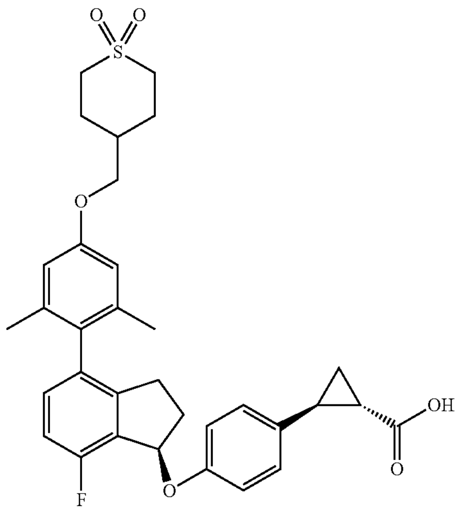 [SMILES: Cc1cc(OCC2CCS(=O)(=O)CC2)cc(C)c1-c1ccc(F)c2c1CC[C@H]2Oc1ccc([C@H]2C[C@@H]2C(=O)O)cc1] | (1S,2S)-2-(4-{(R)-4-[4-(1,1-Dioxo-hexahydro-1-thiopyran-4-ylmethoxy)-2,6-dimethyl-phenyl]-7-fluoro-indan-1-yloxy}-phenyl)-cyclopropane-carboxylic acid | 57 (114 mg) | C | 76 mg | LC (LC METHOD 4): $t_R$ = 7.28 min; Mass spectrum (ES−): m/z = 577 [M − H]−. |
| 22 | 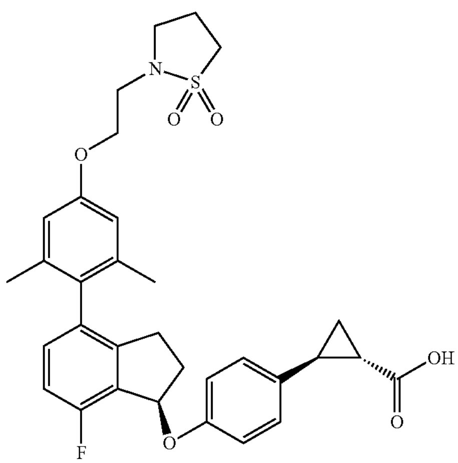 [SMILES: Cc1cc(OCCN2CCCS2(=O)=O)cc(C)c1-c1ccc(F)c2c1CC[C@H]2Oc1ccc([C@H]2C[C@@H]2C(=O)O)cc1] | (1S,2S)-2-[4-((R)-4-{4-[2-(1,1-Dioxo-1-isothiazolidin-2-yl)-ethoxy]-2,6-dimethyl-phenyl}-7-fluoro-indan-1-yloxy)-phenyl]-cyclopropanecarboxylix acid | 58 (56 mg) | C | 31 mg | LC (LC METHOD 4): $t_R$ = 7.18 min; Mass spectrum (ES−): m/z = 578 [M − H]−. |
| 23 | 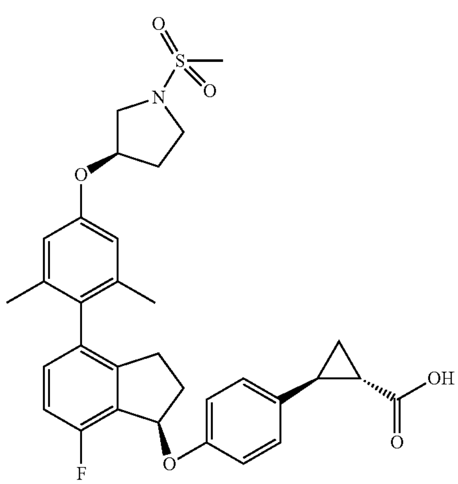 [SMILES: Cc1cc(O[C@@H]2CCN(S(C)(=O)=O)C2)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-((R)-1-methanesulfonyl-pyrrolidin-3-yloxy)-2,6-dimethyl-phenyl]-indan-1-yloxy}-phenyl)-cyclopropanecarboxylic acid | 59 (34 mg) | C | 22 mg | LC (LC METHOD 4): $t_R$ = 7.14 min; Mass spectrum (ES+): m/z = 580 [M + H]+. |

TABLE 9-continued

| Example | Structure | Name | Ester intermediate | Method | Yield | Analysis |
|---|---|---|---|---|---|---|
| 24 | 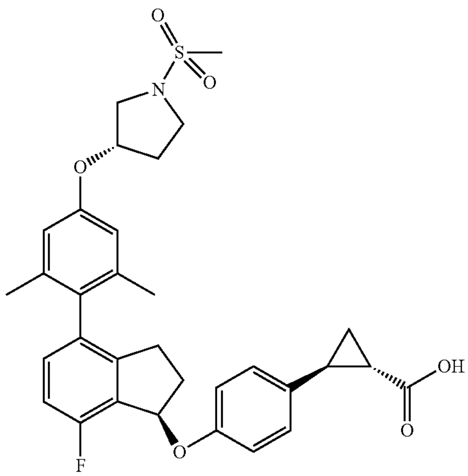 [SMILES: Cc1cc(O[C@H]2CCN(S(C)(=O)=O)C2)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-((S)-1-methanesulfonyl-pyrrolidin-3-yloxy)-2,6-dimethyl-phenyl]-indan-1-yloxy}-phenyl)-cyclopropanecarboxylic acid | 60 (66 mg) | C | 62 mg | LC (LC METHOD 4): $t_R$ = 7.32 min; Mass spectrum (ES−): m/z = 578 [M − H]−. |
| 25 | 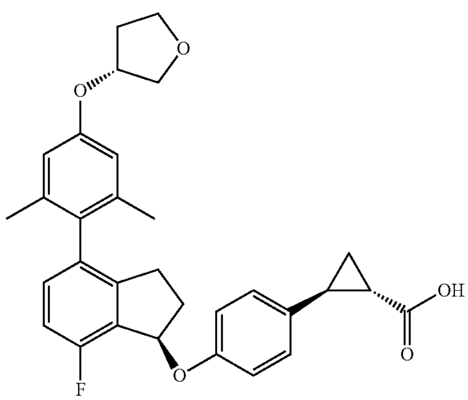 [SMILES: Cc1cc(O[C@@H]2CCOC2)cc(C)c1-c1ccc(F)c2c1CC[C@H]2Oc1ccc([C@H]2C[C@@H]2C(=O)O)cc1] | (1S,2S)-2-[4-((R)-4-{2,6-Dimethyl-4-[(R)-(tetrahydro-furan-3-yl)oxy]-phenyl}-7-fluoro-indan-1-yloxy)-phenyl]-cyclopropanecarboxylic acid | 61 (76 mg) | E | 64 mg | LC (LC METHOD 4): $t_R$ = 7.65 min; Mass spectrum (ES−): m/z = 501 [M − H]−. |
| 26 | 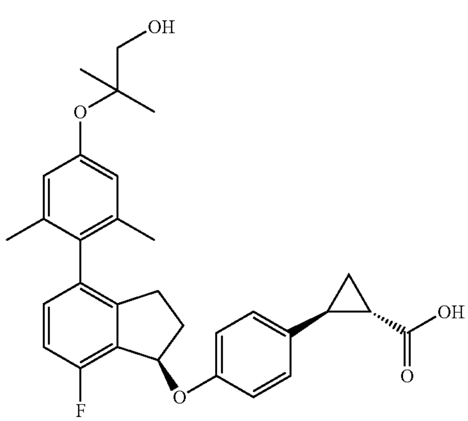 [SMILES: Cc1cc(OC(C)(C)CO)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(2-hydroxy-1,1-dimethyl-ethoxy)-2,6-dimethyl-phenyl]-indan-1-yloxyl-phenyl)-cyclopropanecarboxylic acid | 62 (90 mg) | C | 81 mg | LC (LC METHOD 4): $t_R$ = 7.17 min; Mass spectrum (ES−): m/z = 503 [M − H]−. |

TABLE 9-continued

| Example | Structure | Name | Ester intermediate | Method | Yield | Analysis |
|---|---|---|---|---|---|---|
| 27 | 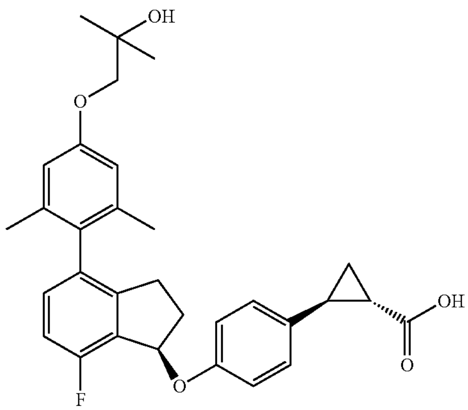 [SMILES: Cc1cc(OCC(C)(C)O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(2-hydroxy-2-methyl-propoxy)-2,6-dimethyl-phenyl]-indan-1-yloxy}-phenyl)-cyclopropanecarboxylic acid | 63 (130 mg) | C | 91 mg | LC (LC METHOD 4): $t_R$ = 7.38 min; Mass spectrum (ES+): m/z = 487 [M − OH]$^-$. |
| 28 | 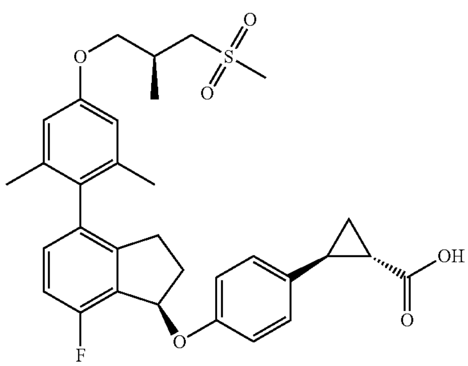 [SMILES: Cc1cc(OC[C@H](C)CS(C)(=O)=O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-((S)-3-methanesulfonyl-2-methyl-propoxy)-2,6-dimethyl-phenyl]-indan-1-yloxy}-phenyl)-cyclopropanecarboxylic acid | 64 (71 mg) | F | 25 mg | LC (LC METHOD 4): $t_R$ = 7.37 min; Mass spectrum (ES−): m/z = 565 [M − H]$^-$. |
| 29 | 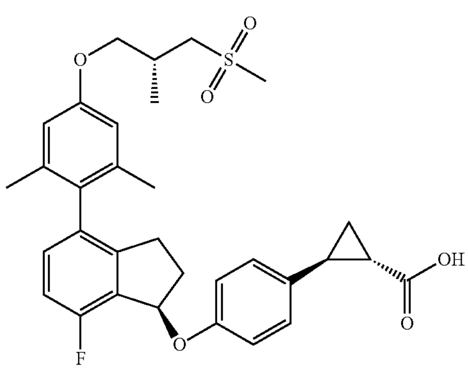 [SMILES: Cc1cc(OC[C@@H](C)CS(C)(=O)=O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-((R)-3-methanesulfonyl-2-methyl-propoxy)-2,6-dimethyl-phenyl]-indan-1-yloxy}-phenyl)-cyclopropanecarboxylic acid | 65 (160 mg) | C | 75 mg | LC (LC METHOD 4): $t_R$ = 7.31 min; Mass spectrum (ES−): m/z = 565 [M − H]$^-$. |
| 30 | 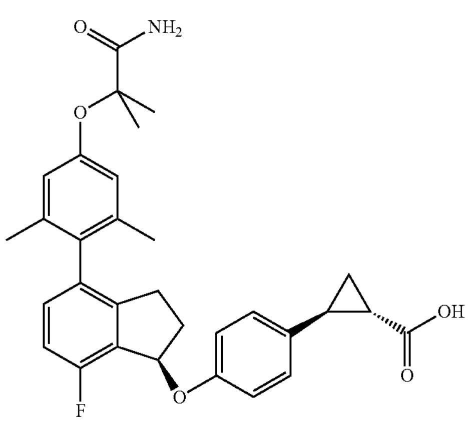 [SMILES: Cc1cc(OC(C)(C)C(N)=O)cc(C)c1-c1ccc(F)c2c1CC[C@H]2Oc1ccc([C@H]2C[C@@H]2C(=O)O)cc1] | (1S,2S)-2-(4-{(R)-4-[4-(1-Carbamoyl-1-methyl-ethoxy)-2,6-dimethyl-phenyl]-7-fluoro-indan-1-yloxy}-phenyl)-cyclopropanecarboxylic acid | 66 (50 mg) | C | 41 mg | LC (LC METHOD 4): $t_R$ = 6.86 min; Mass spectrum (ES+): m/z = 518 [M + H]$^+$. |

TABLE 9-continued

| Example | Structure | Name | Ester intermediate | Method | Yield | Analysis |
|---|---|---|---|---|---|---|
| 31 | 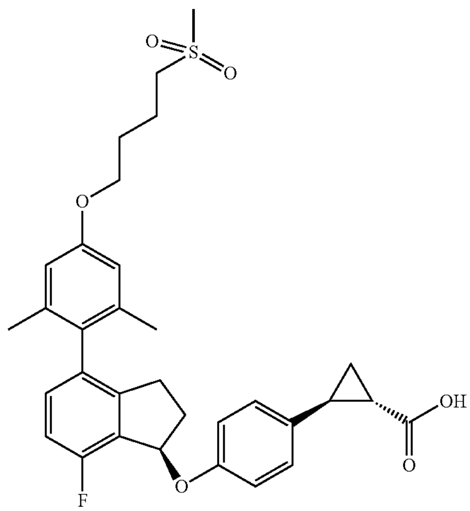 [SMILES: Cc1cc(OCCCCS(C)(=O)=O)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(4-methanesulfonyl-butoxy)-2,6-dimethyl-phenyl]-indan-1-yloxy}-phenyl)-cyclopropanecarboxylic acid | 67 (80 mg) | B | 40 mg | LC (LC METHOD 4): $t_R$ = 7.14 min; Mass spectrum (ES+): m/z = 567 [M + H]⁺. |
| 32 | 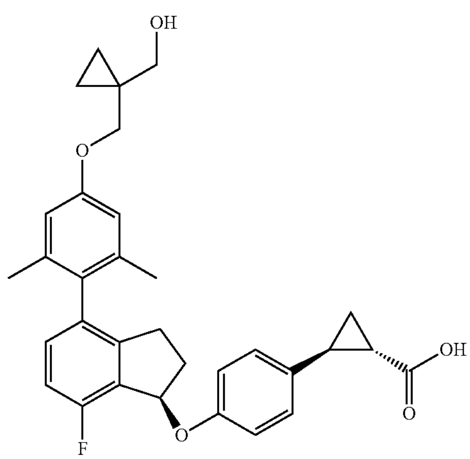 | (1S,2S)-2-(4-{(R)-7-Fluoro-4-[4-(1-hydroxymethyl-cyclopropylmethoxy)-2,6-dimethyl-phenyn-indan-1-yloxy}-phenyl)-cyclopropane-carboxylic acid | 68 (65 mg) | C | 26 mg | LC (LC METHOD 4): $t_R$ = 7.14 min; Mass spectrum (ES+): m/z = 567 [M + H]⁺. |
| 33 | 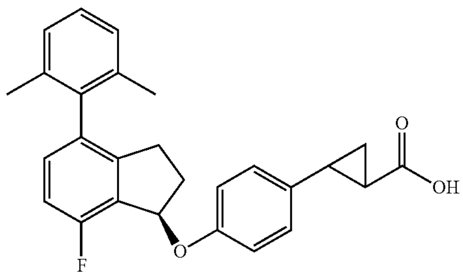 [SMILES: Cc1cccc(C)c1-c1ccc(F)c2c1CC[C@H]2Oc1ccc(C2CC2C(=O)O)cc1] | 2-{4-[(R)-4-(2,6-Dimethyl-phenyl)-7-fluoro-indan-1-yloxy]-phenyl}-trans-cyclopropanecarboxylic acid | 69 (80 mg) | D | 25 mg | LC (LC METHOD 4): $t_R$ = 7.87 min; Mass spectrum (ES-): m/z = 415 [M − H]⁻. |

TABLE 9-continued

| Example | Structure | Name | Ester intermediate | Method | Yield | Analysis |
|---|---|---|---|---|---|---|
| 34 | 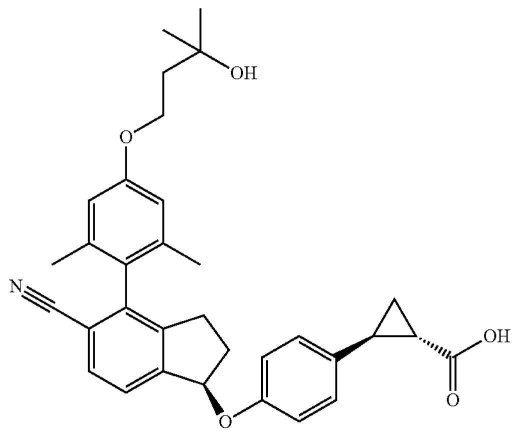 [SMILES: Cc1cc(OCCC(C)(C)O)cc(C)c1-c1c(C#N)ccc2c1CC[C@H]2Oc1ccc([C@H]2C[C@@H]2C(=O)O)cc1] | 1S,2S)-2-(4-{(R)-5-Cyano-4-[4-(3-hydroxy-3-methyl-butoxy)-2,6-dimethyl-phenyl]-indan-1-yloxy}-phenyl)-cyclopropane-carboxylic acid | 72 (45 mg) | F | 30 mg | LC (LC METHOD 4): $t_R$ = 7.02 min; Mass spectrum (ES−): m/z = 524 [M − H]⁻. |
| 35 | 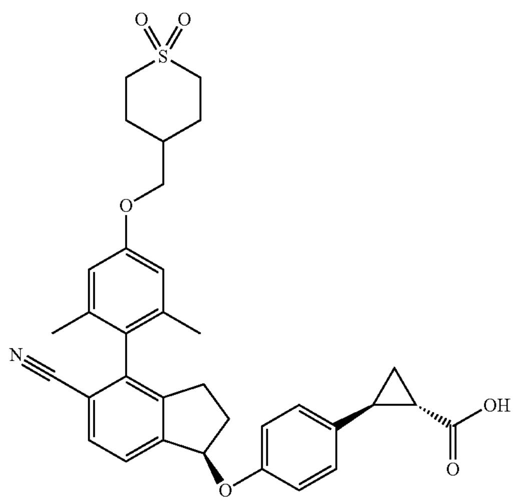 [SMILES: Cc1cc(OCC2CCS(=O)(=O)CC2)cc(C)c1-c1c(C#N)ccc2c1CC[C@H]2Oc1ccc([C@H]2C[C@@H]2C(=O)O)cc1] | 1S,2S)-2-(4-{(R)-5-Cyano-4-[4-(1,1-dioxo-hexahydro-thio-pyran-4-ylmethoxy)-2,6-dimethyl-phenyl]-indan-1-yloxy}-phenyl)-cyclopropane-carboxylic acid | 73 (95 mg) | F | 19 mg | LC (LC METHOD 4): $t_R$ = 6.82 min; Mass spectrum (ES−): m/z = 584 [M − H]⁻. |
| 36 | 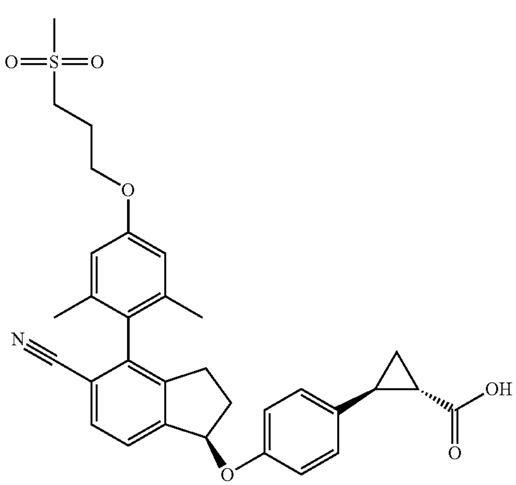 [SMILES: Cc1cc(OCCCS(C)(=O)=O)cc(C)c1-c1c(C#N)ccc2c1CC[C@H]2Oc1ccc([C@H]2C[C@@H]2C(=O)O)cc1] | (1S,2S)-2-(4-{(R)-5-Cyano-4-[4-(3-methanesulfonyl-propoxy)-2,6-dimethyl-phenyl]-indan-1-yloxy}-phenyl)-cyclopropanecarboxylic acid | 74 (45 mg) | F | 2 mg | LC (LC METHOD 9): $t_R$ = 5.00 min; Mass spectrum (ES+): m/z = 560 [M + H]⁺; approx 90% purity at 254 nm |

TABLE 9-continued

| Example | Structure | Name | Ester intermediate | Method | Yield | Analysis |
|---|---|---|---|---|---|---|
| 37 | 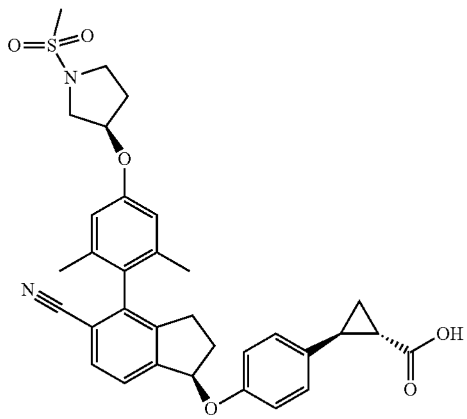 | 1S,2S)-2-(4-{(R)-5-Cyano-4-[4-((R)-1-methanesulfonyl-pyrrolidin-3-yloxy)-2,6-dimethyl-phenyl]-indan-1-yloxy}-phenyl)-cyclopropane-carboxylic acid | 75 (45 mg) | F | 20 mg | LC (LC METHOD 7): $t_R$ = 12.50 min; Mass spectrum (ES+): m/z = 587 [M + H]+. |
| 38 | 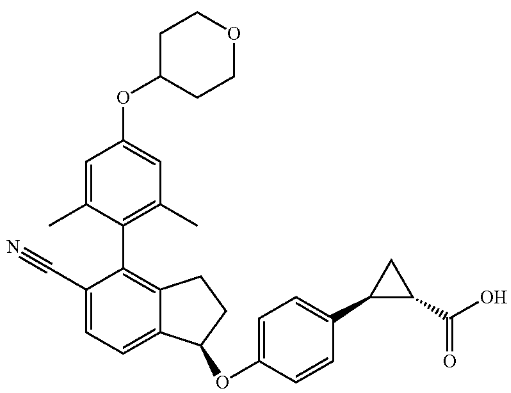 [SMILES: Cc1cc(OC2CCOCC2)cc(C)c1-c1c(C#N)ccc2c1CC[C@H]2Oc1ccc([C@H]2C[C@@H]2C(=O)O)cc1] | (1S,2S)-2-(4-{(R)-5-Cyano-4-[2,6-dimethyl-4-(tetrahydro-pyran-4-yloxy)-phenyl]-indan-1-yloxy}-phenyl)-cyclopropane-carboxylic acid | 76 (45 mg) | F | 5 mg | LC (LC METHOD 12): $t_R$ = 3.50 min; Mass spectrum (ES+): m/z = 524 [M + H]+. |
| 39 | 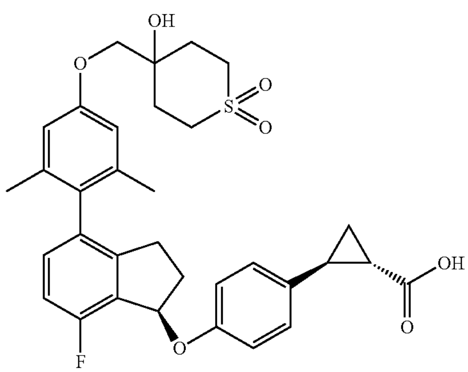 [SMILES: Cc1cc(OCC2(O)CCS(=O)(=O)CC2)cc(C)c1-c1ccc(F)c2c1CC[C@H]2Oc1ccc([C@H]2C[C@@H]2C(=O)O)cc1] | (1S,2S)-2-(4-{(R)-7-Fluoro-4-[4-(4-hydroxy-1,1-dioxo-hexahydro-1-thiopyran-4-ylmethoxy)-2,6-dimethyl-phenyl]-indan-1-yloxy}-phenyl)-cyclopropanecarboxylic acid | 85 (165 mg) | C | 50 mg | LC (LC METHOD 11): $t_R$ = 3.93 min; Mass spectrum (ES+): m/z = 577 [M − OH]+. |
| 40 | 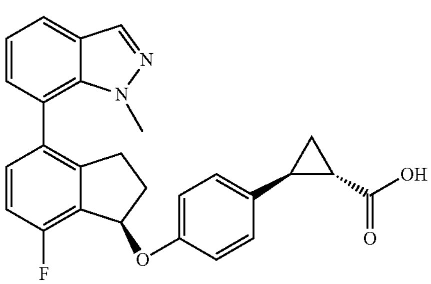 [SMILES: Cn1ncc2cccc(-c3ccc(F)c4c3CC[C@H]4Oc3ccc([C@H]4C[C@@H]4C(=O)O)cc3)c21] | (1S,2S)-2-{4-[(R)-7-Fluoro-4-(1-methyl-1H-indazol-7-yl)-indan-1-yloxyl-phenyl}-cyclopropanecarboxylic acid | 86 (74 mg) | C | 17 mg | LC (LC METHOD 11): $t_R$ = 4.11 min; Mass spectrum (ES+): m/z = 443 [M + H]+. |

TABLE 9-continued

| Example | Structure | Name | Ester intermediate | Method | Yield | Analysis |
|---|---|---|---|---|---|---|
| 41 | 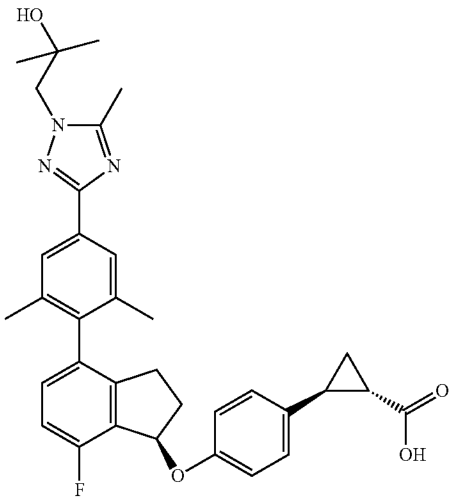 [SMILES: Cc1cc(-c2nc(C)n(CC(C)(C)O)n2)cc(C)c1-c1ccc(F)c2c1CC[C@H]2Oc1ccc([C@H]2C[C@@H]2C(=O)O)cc1] | (1S,2S)-2-[4-((R)-7-Fluoro-4-{4-[1-(2-hydroxy-2-methyl-propyl)-5-methyl-1H-[1,2,4]triazol-3-yl]-2,6-dimethyl-phenyl}-indan-1-yloxy)-phenyl]-cyclopropanecarboxylic acid | 87 (300 mg) | G | 14 mg | LC (LC METHOD 10): $t_R$ = 6.87 min; Mass spectrum (ES+): m/z = 570 [M + H]$^+$. |
| 42 | 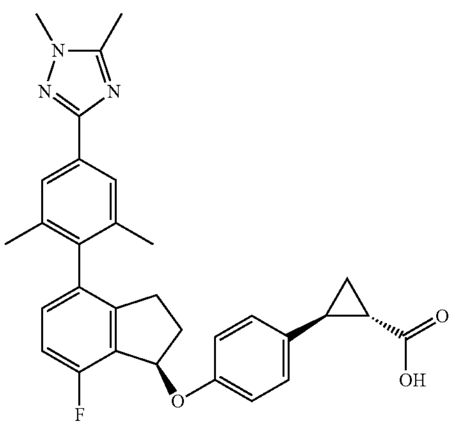 [SMILES: Cc1cc(-c2nc(C)n(C)n2)cc(C)c1-c1ccc(F)c2c1CC[C@H]2Oc1ccc([C@H]2C[C@@H]2C(=O)O)cc1] | (1S,2S)-2-(4-{(R)-4-[4-(1,5-Dimethyl-1H-[1,2,4]triazol-3-yl)-2,6-dimethyl-phenyl]-7-fluoro-indan-1-yloxy}-phenyl)-cyclopropanecarboxylic acid | 88 (130 mg) | G | 7 mg | LC (LC METHOD 11): $t_R$ = 3.84/3.89 min; Mass spectrum (ES+): m/z = 512 [M + H]$^+$. |
| 43 | 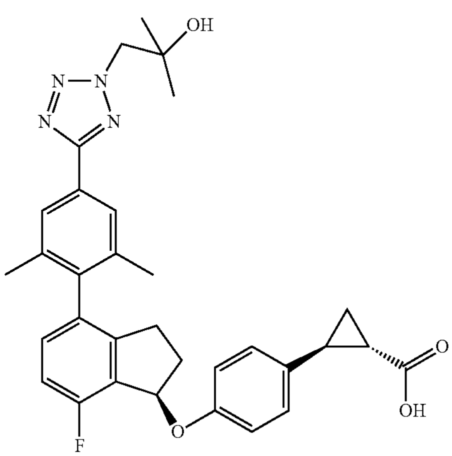 [SMILES: Cc1cc(-c2nnn(CC(C)(C)O)n2)cc(C)c1-c1ccc(F)c2c1CC[C@H]2Oc1ccc([C@H]2C[C@@H]2C(=O)O)cc1] | (1S,2S)-2-[4-((R)-7-Fluoro-4-{4-[2-(2-hydroxy-2-methyl-propyl)-2H-tetrazol-5-yl]-2,6-dimethyl-phenyl}-indan-1-yloxy)-phenyl]-cyclopropanecarboxylic acid | 89 (95 mg) | B | 80 mg | LC (LC METHOD 11): $t_R$ = 4.13 min; Mass spectrum (ES+): m/z = 557 [M + H]$^+$. |

TABLE 9-continued

| Example | Structure | Name | Ester intermediate | Method | Yield | Analysis |
|---|---|---|---|---|---|---|
| 44 | 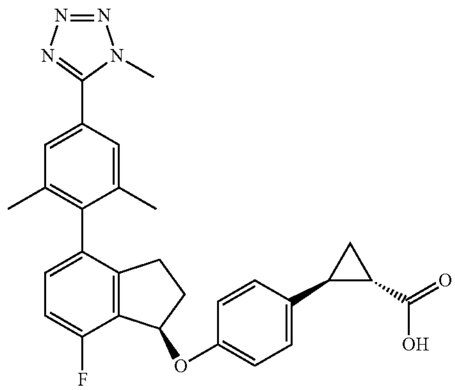 [SMILES: Cc1cc(-c2nnnn2C)cc(C)c1-c1ccc(F)c2c1CC[C@H]2Oc1ccc([C@H]2C[C@@H]2C(=O)O)cc1] | (1S,2S)-2-(4-{(R)-4-[2,6-Dimethyl-4-(1-methyl-tetrazol-5-yl)-phenyl]-7-fluoro-indan-1-yloxy}-phenyl)-cyclopropane-carboxylic acid | 90 (80 mg) | B | 22 mg | LC (LC METHOD 9): $t_R$ = 4.46 min; Mass spectrum (ES+): m/z = 499 [M + H]⁺. |
| 45 | 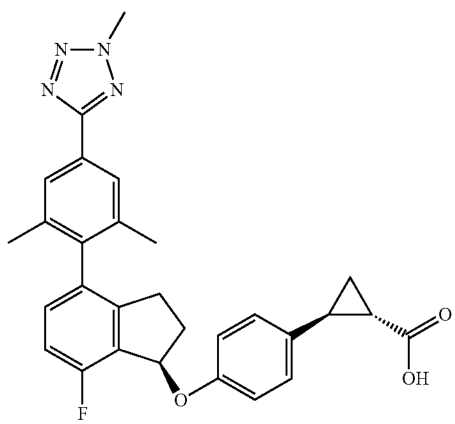 [SMILES: Cc1cc(-c2nnn(C)n2)cc(C)c1-c1ccc(F)c2c1CC[C@H]2Oc1ccc([C@H]2C[C@@H]2C(=O)O)cc1] | (1S,2S)-2-(4-{(R)-4-[2,6-Dimethyl-4-(2-methyl-tetrazol-5-yl)-phenyl]-7-fluoro-indan-1-yloxy}-phenyl)-cyclopropane-carboxylic acid | 91 (80 mg) | B | 22 mg | LC (LC METHOD 12): $t_R$ = 3.65 min; Mass spectrum (ES+): m/z = 499 [M + H]⁺. |
| 46 | 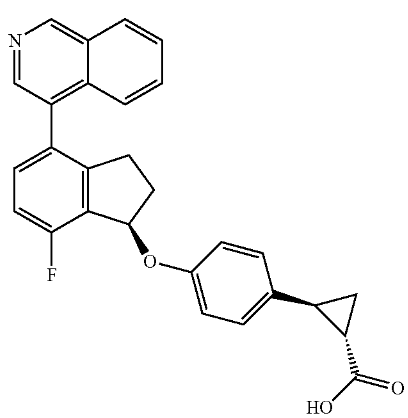 [SMILES: O=C(O)[C@H]1C[C@@H]1c1ccc(O[C@@H]2CCc3c(-c4cncc5ccccc45)ccc(F)c32)cc1] | (1S,2S)-2-(4-((1R)-7-fluoro-4-(isoquinolin-4-yl)-2,3-dihydro-1H-inden-1-yloxy)phenyl)cyclopropanecarboxylic acid | 92 (17.8 mg) | H | 10.9 mg | LC (LC METHOD 13): $t_R$ = 0.77 min; Mass spectrum (ES+): m/z = 440 [M + H]⁺. |

TABLE 9-continued

| Example | Structure | Name | Ester intermediate | Method | Yield | Analysis |
|---|---|---|---|---|---|---|
| 47 | 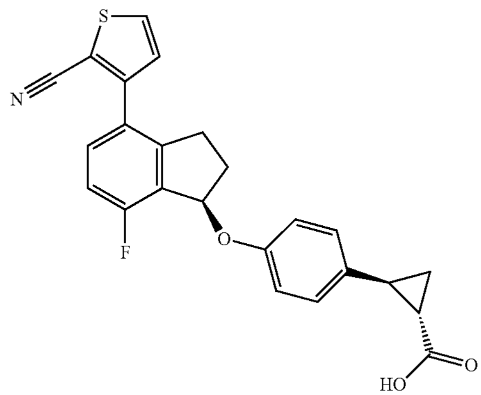 [SMILES: N#Cc1sccc1-c1ccc(F)c2c1CC[C@H]2Oc1ccc([C@H]2C[C@@H]2C(=O)O)cc1] | (1S,2S)-2-(4-((1R)-4-(2-cyanothiophen-3-yl)-7-fluoro-2,3-dihydro-1H-inden-1-yloxy)phenyl)cyclopropanecarboxylic acid | 93 (14.6 mg) | H | 4.0 mg | LC (LC METHOD 13): $t_R$ = 0.77 min; Mass spectrum (ES+): m/z = 440 [M + H]+. |
| 48 | 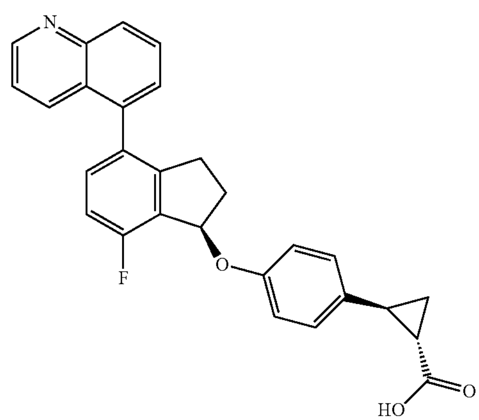 [SMILES: O=C(O)[C@H]1C[C@@H]1c1ccc(O[C@@H]2CCc3c(-c4cccc5ncccc45)ccc(F)c32)cc1] | (1S,2S)-2-(4-((1R)-7-fluoro-4-(quinolin-5-yl)-2,3-dihydro-1H-inden-1-yloxy)phenyl)cyclopropanecarboxylic acid | 94 (21.5 mg) | I | 14.0 mg | LC (LC METHOD 14): $t_R$ = 0.56 min; Mass spectrum (ES+): m/z = 440 [M + H]+. |
| 49 | 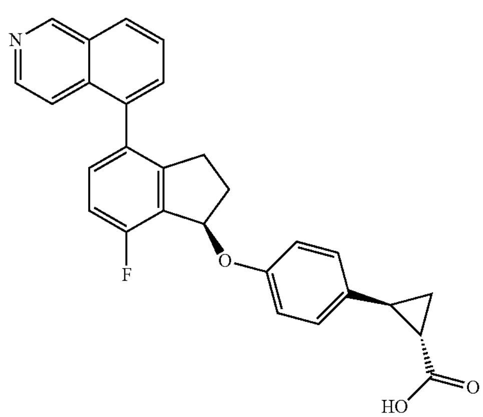 [SMILES: O=C(O)[C@H]1C[C@@H]1c1ccc(O[C@@H]2CCc3c(-c4cccc5cnccc45)ccc(F)c32)cc1] | (1S,2S)-2-(4-((1R)-7-fluoro-4-(isoquinolin-5-yl)-2,3-dihydro-1H-inden-1-yloxy)phenyl)cyclopropanecarboxylic acid | 95 (9.7 mg) | I | 8.5 mg | LC (LC METHOD 14): $t_R$ = 0.55 min; Mass spectrum (ES+): m/z = 440 [M + H]+. |

TABLE 9-continued

| Example | Structure | Name | Ester intermediate | Method | Yield | Analysis |
|---|---|---|---|---|---|---|
| 50 | 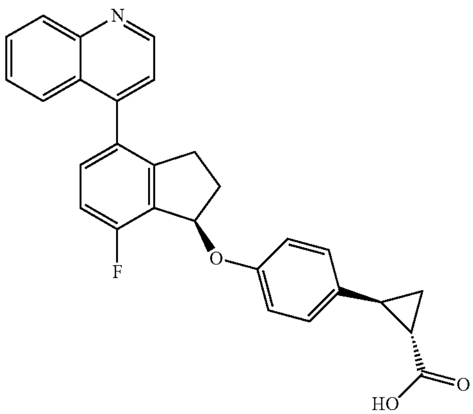 [SMILES: O=C(O)[C@H]1C[C@@H]1c1ccc(O[C@@H]2CCc3c(-c4ccnc5ccccc45)ccc(F)c32)cc1] | (1S,2S)-2-(4-((1R)-7-fluoro-4-(quinolin-4-yl)-2,3-dihydro-1H-inden-1-yloxy)phenyl)cyclopropanecarboxylic acid | 96 (4.5 mg) | I | 4.0 mg | LC (LC METHOD 14): $t_R$ = 0.56 min; Mass spectrum (ES+): m/z = 440 [M + H]$^+$. |
| 51 | 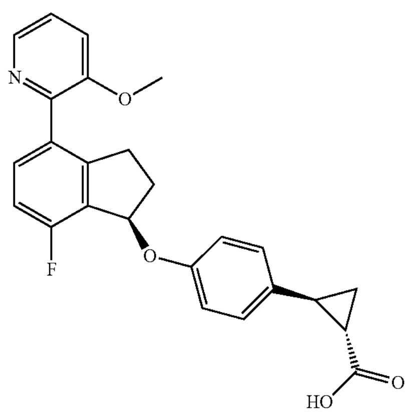 [SMILES: COc1cccnc1-c1ccc(F)c2c1CC[C@H]2Oc1ccc([C@H]2C[C@@H]2C(=O)O)cc1] | (1S,2S)-2-(4-((1R)-7-fluoro-4-(3-methoxypyridin-2-yl)-2,3-dihydro-1H-inden-1-yloxy)phenyl)cyclopropanecarboxylic acid | 97 (12.9 mg) | I | 5.0 mg | LC (LC METHOD 13): $t_R$ = 0.73 min; Mass spectrum (ES+): m/z = 420 [M + H]$^+$. |
| 52 | 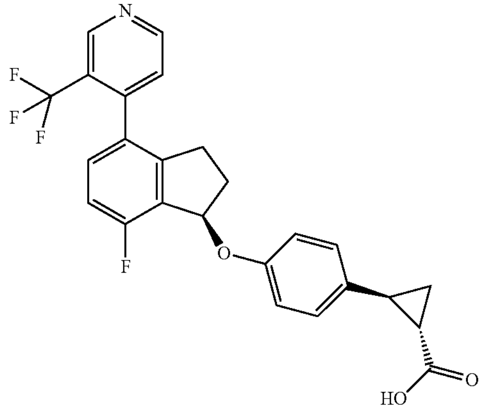 [SMILES: O=C(O)[C@H]1C[C@@H]1c1ccc(O[C@@H]2CCc3c(-c4ccncc4C(F)(F)F)ccc(F)c32)cc1] | (1S,2S)-2-(4-((1R)-7-fluoro-4-(3-(trifluoromethyl)pyridin-4-yl)-2,3-dihydro-1H-inden-1-yloxy)phenyl)cyclopropanecarboxylic acid | 98 (16.0 mg) | I | 11.3 mg | LC (LC METHOD 13): $t_R$ = 1.02 min; Mass spectrum (ES+): m/z = 458 [M + H]$^+$. |

TABLE 9-continued

| Example | Structure | Name | Ester intermediate | Method | Yield | Analysis |
|---|---|---|---|---|---|---|
| 53 | 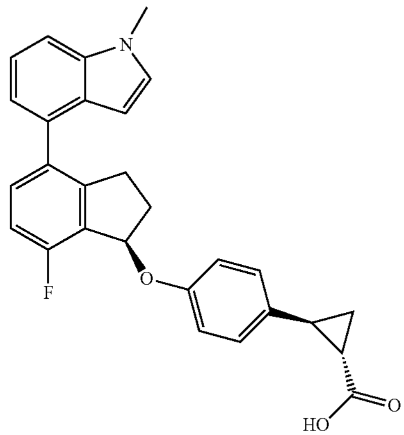 [SMILES: Cn1ccc2c(-c3ccc(F)c4c3CC[C@H]4Oc3ccc([C@H]4C[C@@H]4C(=O)O)cc3)cccc21] | (1S,2S)-2-(4-((1R)-7-fluoro-4-(1-methyl-1H-indol-4-yl)-2,3-dihydro-1H-inden-1-yloxy)phenyl)cyclopropanecarboxylic acid | 99 (6.7 mg) | I | 3.9 mg | LC (LC METHOD 13): $t_R$ = 1.07 min; Mass spectrum (ES+): m/z = 442 [M + H]$^+$. |
| 54 | 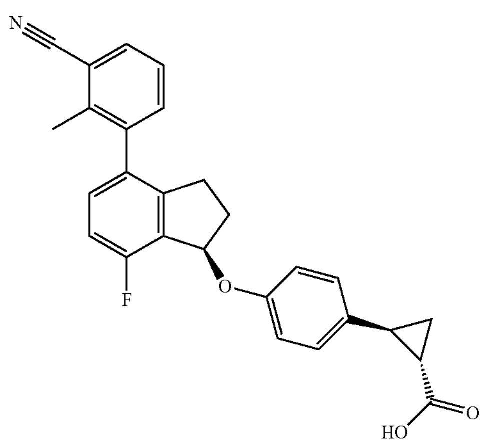 [SMILES: Cc1c(C#N)cccc1-c1ccc(F)c2c1CC[C@H]2Oc1ccc([C@H]2C[C@@H]2C(=O)O)cc1] | (1S,2S)-2-(4-((1R)-4-(3-cyano-2-methylphenyl)-7-fluoro-2,3-dihydro-1H-inden-1-yloxy)phenyl)cyclopropanecarboxylic acid | 100 (18.7 mg) | I | 15.5 mg | LC (LC METHOD 13): $t_R$ = 1.02 min; Mass spectrum (ES−): m/z = 426.0 [M − H]$^-$. |
| 55 | 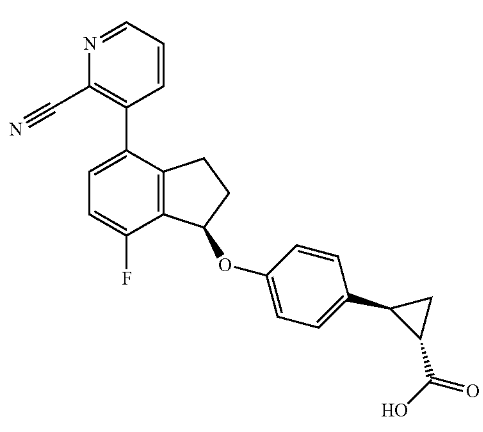 [SMILES: N#Cc1ncccc1-c1ccc(F)c2c1CC[C@H]2Oc1ccc([C@H]2C[C@@H]2C(=O)O)cc1] | (1S,2S)-2-(4-((1R)-4-(2-cyanopyridin-3-yl)-7-fluoro-2,3-dihydro-1H-inden-1-yloxy)phenyl)cyclopropanecarboxylic acid | 101 (28.4 mg) | I | 16.8 mg | LC (LC METHOD 13): $t_R$ = 0.90 min; Mass spectrum (ES−): m/z = 413.0 [M − H]$^-$. |

TABLE 9-continued

| Example | Structure | Name | Ester intermediate | Method | Yield | Analysis |
|---|---|---|---|---|---|---|
| 56 | 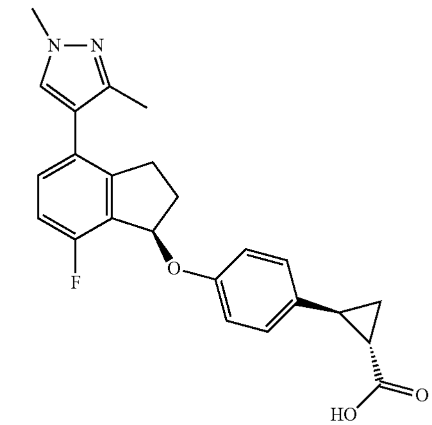 [SMILES: Cc1nn(C)cc1-c1ccc(F)c2c1CC[C@H]2Oc1ccc([C@H]2C[C@@H]2C(=O)O)cc1] | (1S,2S)-2-(4-((1R)-4-(1,3-dimethyl-1H-pyrazol-4-yl)-7-fluoro-2,3-dihydro-1H-inden-1-yloxy)phenyl)cyclopropanecarboxylic acid | 102 (16.6 mg) | I | 12.9 mg | LC (LC METHOD 13): $t_R$ = 0.90 min; Mass spectrum (ES+): m/z = 407 [M + H]$^+$. |
| 57 | 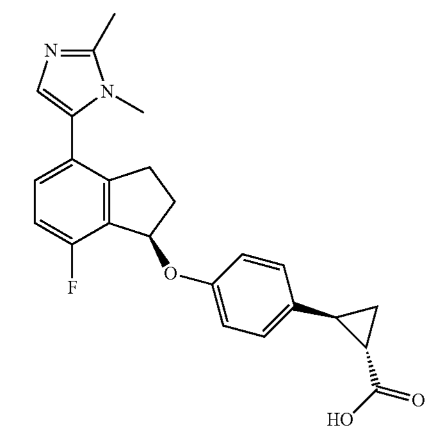 [SMILES: Cc1ncc(-c2ccc(F)c3c2CC[C@H]3Oc2ccc([C@H]3C[C@@H]3C(=O)O)cc2)n1C] | (1S,2S)-2-(4-((1R)-4-(1,2-dimethyl-1H-imidazol-5-yl)-7-fluoro-2,3-dihydro-1H-inden-1-yloxy)phenyl)cyclopropanecarboxylic acid | 103 (9.1 mg) | I | 5.3 mg | LC (LC METHOD 13): $t_R$ = 0.69 min; Mass spectrum (ES+): m/z = 407 [M + H]$^+$. |
| 58 | 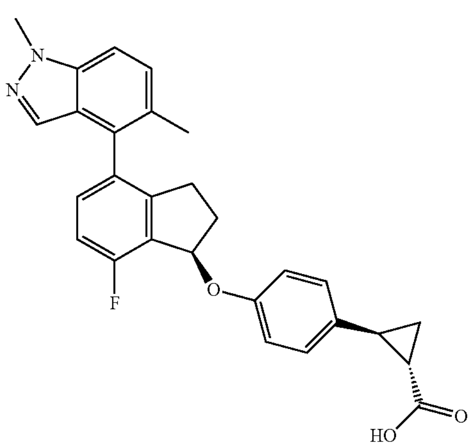 [SMILES: Cc1ccc2c(cnn2C)c1-c1ccc(F)c2c1CC[C@H]2Oc1ccc([C@H]2C[C@@H]2C(=O)O)cc1] | (1S,2S)-2-(4-((1R)-4-(1,5-dimethyl-1H-indazol-4-yl)-7-fluoro-2,3-dihydro-1H-inden-1-yloxy)phenyl)cyclopropanecarboxylic acid | 104 (17.3 mg) | I | 9.0 mg | LC (LC METHOD 13): $t_R$ = 1.0 min; Mass spectrum (ES+): m/z = 457 [M + H]$^+$. |

TABLE 9-continued

| Example | Structure | Name | Ester intermediate | Method | Yield | Analysis |
|---|---|---|---|---|---|---|
| 59 | 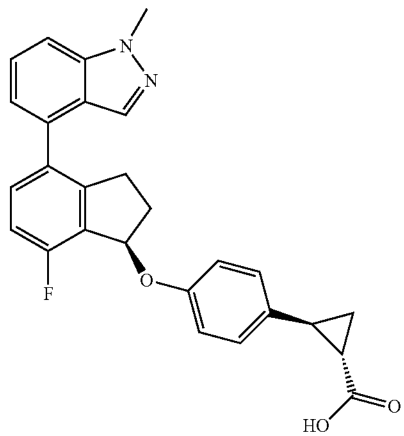 [SMILES: Cn1ncc2c(-c3ccc(F)c4c3CC[C@H]4Oc3ccc([C@H]4C[C@@H]4C(=O)O)cc3)cccc21] | (1S,2S)-2-(4-((1R)-7-fluoro-4-(1-methyl-1H-indazol-4-yl)-2,3-dihydro-1H-inden-1-yloxy)phenyl)cyclopropanecarboxylic acid | 105 (24.1 mg) | I | 16.9 mg | LC (LC METHOD 13): $t_R$ = 1.05 min; Mass spectrum (ES+): m/z = 465 [M + Na]+. |
| 60 | 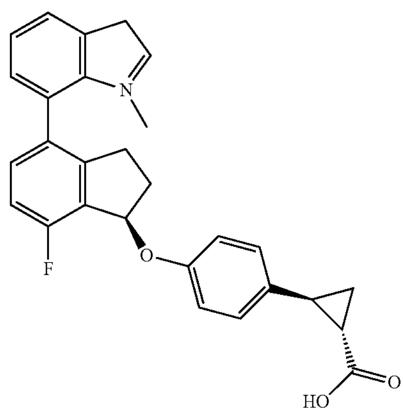 | (1S,2S)-2-(4-((1R)-7-fluoro-4-(1-methyl-1H-indol-7-yl)-2,3-dihydro-1H-inden-1-yloxy)-phenyl)cyclopropanecarboxylic acid | 106 (28.6 mg) | I | 21.4 mg | LC (LC METHOD 13): $t_R$ = 1.07 min; Mass spectrum (ES+): m/z = 442 [M + H]+. |
| 61 | 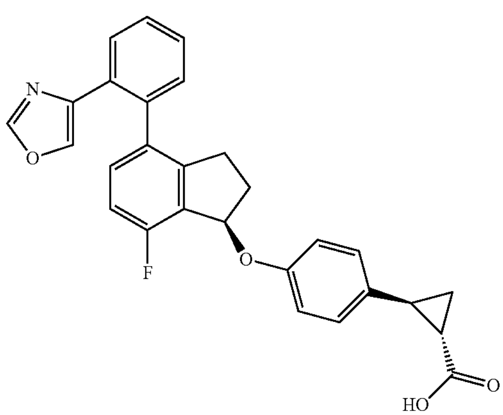 [SMILES: O=C(O)[C@H]1C[C@@H]1c1ccc(O[C@@H]2CCc3c(-c4ccccc4-c4cocn4)ccc(F)c32)cc1] | (1S,2S)-2-(4-((1R)-7-fluoro-4-(2-(oxazol-4-yl)phenyl)-2,3-dihydro-1H-inden-1-yloxy)-phenyl)cyclopropanecarboxylic acid | 107 (22.9 mg) | I | 13.8 mg | LC (LC METHOD 13): $t_R$ = 1.01 min; Mass spectrum (ES+): m/z = 456 [M + H]+. |

TABLE 9-continued

| Example | Structure | Name | Ester intermediate | Method | Yield | Analysis |
|---|---|---|---|---|---|---|
| 62 | 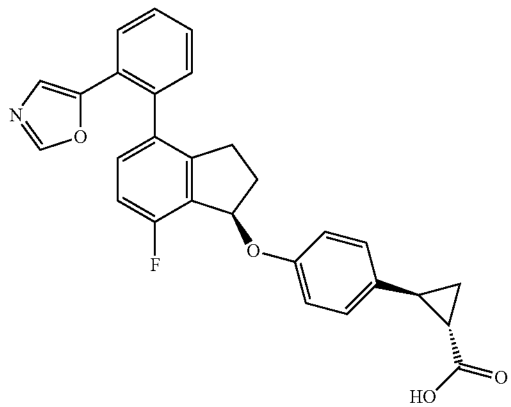 [SMILES: O=C(O)[C@H]1C[C@@H]1c1ccc(O[C@@H]2CCc3c(-c4ccccc4-c4cnco4)ccc(F)c32)cc1] | (1S,2S)-2-(4-((1R)-7-fluoro-4-(2-(oxazol-5-yl)phenyl)-2,3-dihydro-1H-inden-1-yloxy)phenyl)cyclopropanecarboxylic acid | 108 (20.4 mg) | I | 16.5 mg | LC (LC METHOD 13): $t_R$ = 1.15 min; Mass spectrum (ES+): m/z = 456 [M + H]+. |
| 63 | 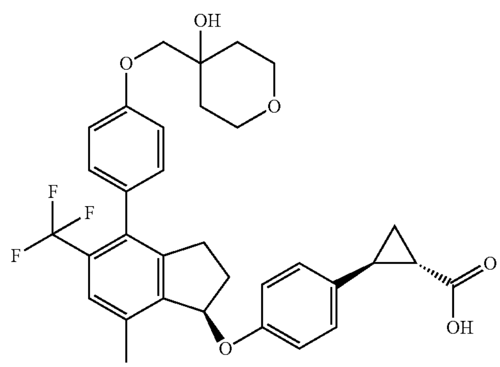 | (1S,2S)-2-(4-{(R)-4-[4-(4-Hydroxy-tetrahydro-pyran-4-ylmethoxy)-phenyl]-5-trifluoromethyl-indan-1-yloxy}-phenyl)-cyclopropanecarboxylic acid | 111 (50 mg) | J | 40 mg | LC (LC METHOD 12): $t_R$ = 3.32 min; Mass spectrum (ES−): m/z =567 [M − H]−. |
| 64 | 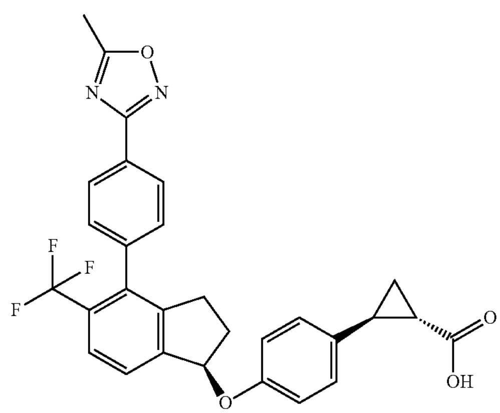 [SMILES: Cc1nc(-c2ccc(-c3c(C(F)(F)F)ccc4c3CC[C@H]4Oc3ccc([C@H]4C[C@@H]4C(=O)O)cc3)cc2)no1] | (1S,2S)-2-(4-{(R)-4-[4-(5-Methyl-[1,2,4]oxadiazol-3-yl)-phenyl]-5-trifluoromethyl-indan-1-yloxy}-phenyl)-cyclopropanecarboxylic acid | 112 (50 mg) | J | 20 mg | LC (LC METHOD 12): $t_R$ = 3.63 min; Mass spectrum (ES+): m/z = 521 [M + H]+. |

The invention claimed is:

1. A compound of formula (I)

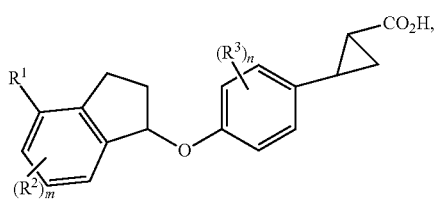

wherein:

R[1] is selected from the group R[1]-G1 consisting of a phenyl ring, a tetrazolyl ring,
  a 5-membered heteroaromatic ring containing 1 —NH—, or —S— group,
  a 5-membered heteroaromatic ring containing 1 —NH—, or —S— group and additionally 1 or 2 =N— atoms,
  a 6-membered heteroaromatic ring containing 1, 2 or 3 =N— atoms,
  wherein: optionally a second ring is annulated to the phenyl ring or to the 5- or 6-membered heteroaromatic rings and the second ring is 5- or 6-membered, unsaturated or aromatic and may contain 1, 2, or 3 heteroatoms independently selected from =N—, —NH—, and —S— with the proviso that only up to two of the heteroatoms are O and S and no O—O, S—S, and S—O bond is formed, and wherein in the second ring independently of the presence of heteroatoms 1 or 2 $CH_2$ groups are optionally replaced by —C(O)—, —S(O)—, or —S(O)$_2$—, the phenyl ring, tetrazolyl ring, 5- or 6-membered heteroaromatic ring, annulated phenyl ring, and annulated 5- or 6-membered heteroaromatic ring are optionally substituted at a carbon atom with one group $R^{1a}$, the phenyl ring, tetrazolyl ring, 5- or 6-membered heteroaromatic ring, annulated phenyl ring, and annulated 5- or 6-membered heteroaromatic ring are optionally additionally substituted at carbon atoms with 1 to 3 groups independently selected from $R^{1b}$, and wherein the H-atom in one or more NH groups present in the tetrazolyl ring, 5- or 6-membered heteroaromatic ring, annulated phenyl ring, or annulated 5- or 6-membered heteroaromatic ring optionally is replaced by $R^M$, H, F, Cl, Br, I, NC—, $C_{1-8}$-alkyl, $C_{2-6}$-alkenyl, $C_{2-6}$-alkynyl, $C_{3-8}$-cycloalkyl, $C_{3-8}$ cycloalkyl $C_{1-4}$-alkyl, $C_{5-12}$-bicycloalkyl-, $C_{5-6}$-cycloalkenyl, $C_{5-6}$-cyclo $C_{1-8}$-alkyloxy, $C_{3-6}$-cycloalkyl-oxy, $C_{3-6}$-cycloalkyl-$C_{1-4}$-alkyloxy, —NHR$^N$, HNR$^M$—C(O)—, $C_{1-4}$-alkyl-NR$^M$—C(O)—, wherein any of the saturated and unsaturated aliphatic and carbocyclic groups and submoieties within the groups mentioned are optionally independently substituted with one or more F atoms and/or 1 to 3 $R^{1c}$ groups, $R^2$ is selected from the group $R^2$-G1 consisting of F, Cl, Br, I, $C_{1-4}$-alkyl, $C_{3-6}$-cycloalkyl, NC—, $H_2N$—C(O)—, $C_{1-4}$-alkyl-NR$^M$—C(O)—, HO—C(O)—, $C_{1-4}$-alkyl-O—C(O)—, $C_{1-4}$-alkyloxy, and $C_{1-4}$-alkyl-S(O)$_2$—, wherein any alkyl and cycloalkyl group or sub-group within the groups mentioned is optionally substituted with one or more F atoms, and wherein multiple $R^2$ are identical or different, if m is 2 or 3;

$R^3$ is selected from the group $R^3$-G1 consisting of F, Cl, Br, I, NC—, $C_{1-6}$-alkyl, $C_{2-6}$-alkenyl, $C_{2-6}$-alkynyl, $C_{3-6}$-cycloalkyl-, $C_{1-4}$-akyl-NH—, $(C_{1-4}$-alkyl)$_2$N—, $C_{1-6}$-alkyl-O—, $C_{3-6}$-cycloalkyl-O—, $C_{1-4}$-alkyl-S—, $C_{1-4}$-alkyl-S(O)—, and $C_{1-4}$-alkyl-S(O)$_2$, wherein each alkyl and cycloalkyl group and each alkyl and cycloalkyl sub-group within the groups mentioned is optionally substituted with 1 or more F atoms;

m is 0, 1, 2, and or 3;

n is 0, 1, 2, and or 3;

$R^{1a}$ is selected from the group $R^{1a}$-G1 consisting of $C_{1-6}$ alkyl, $C_{2-6}$-alkenyl, $C_{2-6}$-alkynyl, $C_{3-6}$-cycloalkyl-, $C_{3-6}$-cycloalkyl-$C_{1-6}$-alkyl, $C_{1-4}$-alkyl-NH—, $(C_{1-4}$-alkyl)$_2$N—, —NHR$^N$, HNR$^M$—C(O)—, $C_{1-4}$-alkyl-NR$^M$—C(O)—, $C_{1-6}$-alky-O—, $C_{3-6}$-cycloalkyl-O—, $C_{3-6}$-cycloalkyl-$C_{1-6}$-alkyl-O—, $C_{1-4}$-alkyl-S—, $C_{1-4}$-alkyl-S(O)—, and $C_{1-4}$-alkyl-S(O)$_2$, wherein: a —$CH_2$— member within a $C_{4-6}$-cycloalkyl- group or sub-group within the groups mentioned optionally is replaced by —NR$^N$—, —O—, —S—, —S(O)—, or —S(O)$_2$—, or a >CH—$CH_2$— member or a —$CH_2$—$CH_2$— member within a $C_{5-6}$-cycloalkyl- group or sub-group within the groups mentioned optionally is replaced by >N—C(O)—, >N—S(O)—, >N—S(O)$_2$—, —N(R$^M$)—C(O)—, —N(R$^M$)—S(O)—, or —N(R$^M$)—S(O)$_2$—, and each alkyl and cycloalkyl group and each alkyl and cycloalkyl sub-group within the groups mentioned optionally is substituted with HO—, HO—$C_{1-4}$-alkyl-, $C_{1-4}$-alkyl-oxy, $C_{1-4}$-alkyl-oxy-$C_{1-4}$-alkyl-, $C_{1-4}$-alkyl-sulfanyl, $C_{1-4}$-alkyl-sulfinyl, $C_{1-4}$-alkyl-sulfonyl, $H_2N$—C(O)—, $C_{1-4}$-alkyl-NH—C(O)—, $(C_{1-4}$-alkyl)$_2$N—C(O)—, or $C_{3-6}$-cycloalkyl-NR$^M$—C(O)— and/or optionally substituted with 1 or more F atoms;

a phenyl ring, a tetrazolyl ring, a 5-membered heteroaromatic ring containing 1 —NH—, —O—, or —S— group, a 5-membered heteroaromatic ring containing 1 —NH—, —O—, or —S— group and additionally 1 or 2 =N— atoms, a 6-membered heteroaromatic ring containing 1, 2, or 3 =N— atoms, wherein the rings are optionally substituted with one or more groups selected from $R^{1b}$; and wherein the H-atom in one or more NH groups present in the tetrazolyl ring or 5-membered heteroaromatic ring is replaced by $R^M$, $R^{1b}$ is selected from the group $R^{1b}$-G1 consisting of F, Cl, Br, I, CN, —OH, $C_{1-4}$-alkyl, $C_{3-6}$-cycloalkyl-, HO—$C_{1-4}$-alkyl, $C_{1-4}$-alkyl-O—$C_{1-4}$-alkyl, —NR$^N$H, $C_{1-4}$-alkyl-NR$^N$—, $C_{1-4}$-alkyl-O—, $C_{3-6}$-cycloalkyl-O—, $C_{1-4}$-alkyl-O—$C_{1-4}$-alkyl-O—, $C_{1-4}$-alkyl-S—, $C_{1-4}$-alkyl-S(O)—, and $C_{1-4}$-alkyl-S(O)$_2$—, wherein any alkyl and cycloalkyl group or sub-group within the groups mentioned is optionally substituted with 1 or more F atoms;

$R^{1c}$ is selected from the group $R^{1c}$-G1 consisting of F, Cl, Br, I, CN, —OH, $C_{1-3}$-alkyl, HO—$C_{1-3}$-alkyl, $C_{1-4}$-alkyl-O—, and $C_{1-3}$-alkyl-O—$C_{1-3}$-alkyl, wherein any alkyl group or sub-group within the groups mentioned is optionally substituted with 1 or more F atoms; and $R^N$ is independently selected from the group $R^N$-G1 consisting of H, $C_{1-4}$-alkyl, HO—$C_{2-4}$-alkyl (with the proviso that at least 2 carbon atoms are between the HO-group and an NH), $C_{1-4}$-alkyl-O—$C_{2-4}$-alkyl- (with the proviso that at least 2 carbon atoms are between an O-group and an NH), $C_{1-4}$-alkyl-C(O)—, $C_{1-4}$-alkyl-O—C(O)—, and $C_{1-4}$-alkyl-S(O)$_2$, wherein any alkyl group or sub-group within the groups mentioned is optionally substituted with 1 or more F atoms;

$R^M$ is independently selected from the group $R^M$-G1 consisting of H, $C_{1-4}$ alkyl, HO—$C_{2-4}$-alkyl (with the proviso that at least 2 carbon atoms are between the HO-group and an NH), and $C_{1-4}$-alkyl-O—$C_{2-4}$-alkyl- (with the proviso that at least 2 carbon atoms are between an O-group and an NH), wherein any alkyl group or sub-group within the groups mentioned is optionally substituted with 1 or more F atoms;

wherein in any definition mentioned hereinbefore and if not specified otherwise, any alkyl group or sub-group may be straight-chained or branched, or a salt thereof.

2. The compound according to claim 1, wherein:

$R^1$ is selected from the group $R^1$-G2 consisting of
  a phenyl ring, a tetrazolyl ring,
  a 5-membered heteroaromatic ring containing 1 —NH— or —O-group,
  a 5-membered heteroaromatic ring containing 1 —NH— or 1-O— group and additionally 1 or 2 =N— atoms,
  a 6-membered heteroaromatic ring containing 1, or 3 =N— atoms,
    wherein: the phenyl ring, tetrazolyl ring and 5- or 6-membered heteroaromatic ring are substituted at a carbon atom with one group $R^{1a}$; and
    the phenyl ring, tetrazolyl ring, 5- or 6-membered heteroaromatic ring are optionally additionally substituted at carbon atoms with 1 to 3 groups independently selected from $R^{1b}$; and
    the H-atom in one or more NH groups present in the tetrazolyl ring, 5- or 6-membered heteroaromatic ring optionally is replaced by $R^M$,
  H, F, Cl, Br, J, NC—, $C_{1-6}$-alkyl, $C_{2-4}$-alkenyl, $C_{2-4}$-alkynyl, $C_{3-6}$-cycloalkyl, $C_{3-6}$-cycloalkyl-$C_{1-3}$-alkyl, $C_{5-10}$-bicycloalkyl-, $C_{5-10}$-bicycloalkyl-$C_{1-4}$-alkyl-, $C_{1-4}$-alkyloxy, $C_{3-6}$-cycloalkyl-oxy, $C_{3-6}$-cycloalkyl-$C_{1-3}$-alkyloxy, $C_{1-3}$-alkyl-C(O)—, —$NHR^N$, $HNR^M$—C(O)—, $C_{1-4}$-alkyl-$NR^M$—C(O)—, wherein any of the saturated and unsaturated aliphatic and carbocyclic groups and submoieties within the groups mentioned are optionally independently substituted with 1 to 3 fluorine atoms and/or 1 $R^{1c}$ group, m is 1 or 2,
n is 0 or 1, $R^{1a}$ is selected from the group $R^{1a}$-G2a consisting of
  $C_{1-4}$-alkyl, $C_{2-4}$-alkenyl, $C_{2-4}$-alkynyl, $C_{3-6}$-cycloalkyl-, $C_{3-6}$-cycloalkyl-$C_{1-4}$-alkyl, $C_{1-4}$-alkyl-NH—, ($C_{1-4}$-alkyl)$_2$N—, —$NHR^N$, $HNR^M$—C(O)—, $C_{1-4}$-alkyl-$NR^M$—C(O)—, $C_{1-6}$-alkyl-O—, $C_{3-6}$-cycloalkyl-O—, $C_{3-6}$-cycloalkyl-$C_{1-4}$-alkyl-O—, and $C_{1-4}$-alkyl-S(O)$_2$,
    wherein: a —CH$_2$— member within a $C_{4-6}$-cycloalkyl- group or sub-group within the groups mentioned optionally is replaced by —$NR^N$—, —O—, or —S(O)$_2$—, or
    a >CH—CH$_2$— member or a —CH$_2$—CH$_2$— member within a $C_{5-6}$-cycloalkyl- group or sub-group within the groups mentioned optionally is replaced by >N—C(O)—, >N—S(O)$_2$—, —N($R^M$)—C(O)—, or —N($R^M$)—S(O)$_2$—, and
    each alkyl and cycloalkyl group and each alkyl and cycloalkyl sub-group within the groups mentioned optionally is substituted with HO—, HO—$C_{1-3}$-alkyl-, $C_{1-3}$-alkyl-oxy, $C_{1-3}$-alkyloxy-$C_{1-4}$-alkyl-, $C_{1-4}$-alkyl-sulfonyl, $H_2N$—C(O)—, $C_{1-4}$-alkyl-NH—C(O)—, or ($C_{1-4}$-alkyl)$_2$N—C(O)— and/or optionally substituted with 1 to 3 F atoms, $R^{1b}$ is selected from the group $R^{1b}$-G2 consisting of F, Cl, Br, I, CN, —OH, $C_{1-3}$-alkyl, $C_{3-6}$-cycloalkyl-, HO—$C_{1-3}$-alkyl, $C_{1-3}$-alkyl-O—, and $C_{3-6}$-cycloalkyl-O—, wherein any alkyl and cycloalkyl group or sub-group within the groups mentioned is optionally substituted with 1 to 3 F atoms, $R^{1c}$ is selected from the group $R^{1c}$-G2 consisting of F, Cl, Br, —OH, $C_{1-3}$-alkyl, HO—$C_{1-3}$-alkyl, and $C_{1-4}$-alkyl-O—, wherein any alkyl group or sub-group within the groups mentioned is optionally substituted with 1 to 3 F atoms, $R^N$ is selected from the group $R^N$-G2 consisting of H, $C_{1-4}$-alkyl, HO—$C_{1-4}$-alkyl (with the proviso that at least 2 carbon atoms are between the HO-group and an NH), $C_{1-4}$-alkyl-C(O)—, $C_{1-3}$-alkyl-O—C(O)—, and $C_{1-3}$-alkyl-S(O)$_2$—, wherein any alkyl group or sub-group within the groups mentioned is optionally substituted with 1 to 3 F atoms, $R^M$ is selected from the group $R^M$-G2 consisting of H, $C_{1-3}$-alkyl, HO—$C_{2-4}$-alkyl (with the proviso that at least 2 carbon atoms are between the HO-group and an NH), and $C_{1-3}$-alkyl-O—$C_{2-3}$-alkyl- (with the proviso that at least 2 carbon atoms are between an O-group and an NH), wherein any alkyl group or sub-group within the groups mentioned is optionally substituted with 1 to 5 F atoms, or a salt thereof.

3. The compound according to claim 2, wherein:

$R^{1a}$ is selected from the group $R^{1a}$-G2b consisting of
  a phenyl ring, a tetrazolyl ring,
  a 5-membered heteroaromatic ring containing 1 —NH— or —O— group,
  a 5-membered heteroaromatic ring containing 1 —NH— or —O— group and additionally 1 or 2 =N— atoms,
  a 6-membered heteroaromatic ring containing 1 or 2 =N— atoms,
    wherein: the rings are optionally substituted with one to three groups selected from $R^{1b}$, and the H-atom in one or more NH groups present in the tetrazolyl ring or 5-membered heteroaromatic ring is replaced by $R^M$, or a salt thereof.

4. The compound according to claim 1, wherein:

$R^2$ is selected from the group $R^2$-G2 consisting of F, Cl, Br, I, $C_{1-3}$-alkyl, $C_{3-6}$-cycloalkyl, NC—, $H_2N$—C(O)—, $C_{1-3}$-alkyl-$NR^M$—C(O)—, HO—C(O)—, $C_{1-3}$-alkyl-O—C(O)—, and $C_{1-3}$-alkyloxy, wherein any alkyl and cycloalkyl group or sub-group within the groups mentioned is optionally substituted with 1 to 3 F atoms, and wherein multiple $R^2$ are identical or different, if m is 2 or 3, or a salt thereof.

5. The compound according to claim 1, wherein:

$R^3$ is selected from the group $R^3$-G2 consisting of F, Cl, Br, NC—, $C_{1-4}$-alkyl, $C_{2-4}$-alkenyl, $C_{2-4}$-alkynyl, $C_{3-6}$-cycloalkyl-, $C_{1-3}$-alkyl-NH—, ($C_{1-3}$-alkyl)$_2$N—, $C_{1-4}$-alkyl-O—, $C_{3-6}$-cycloalkyl-O—, and $C_{1-3}$-alkyl-S(O)$_2$, wherein each alkyl and cycloalkyl group and each alkyl and cycloalkyl sub-group within the groups mentioned is optionally substituted with 1 to 3 F atoms, or a salt thereof.

6. The compound according to claim 1 selected from embodiments E2 to E44 disclosed in table 1, or a salt thereof.

7. The compound according to claim 1, with the stereochemistry shown in formula I.1 or I.2

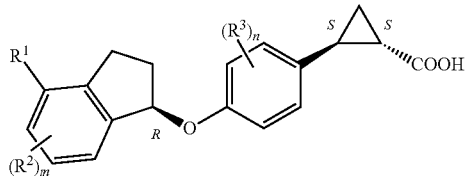

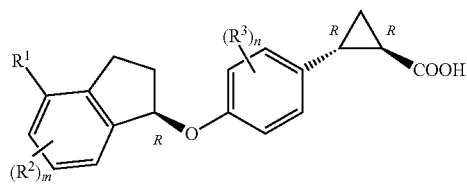

or a salt thereof.

8. A pharmaceutically acceptable salt of a compound according to claim 1.

9. A pharmaceutical composition comprising one or more compounds according to claim 1 or a pharmaceutically acceptable salts thereof, and an inert carriers or diluents.

10. A method for palliatively treating diseases or conditions which are influenced by modulation of the GPR40 receptor, in a patient in need thereof, said method comprising administering to the patient an effective amount of the compound according to claim 1 or a pharmaceutically acceptable salt thereof.

11. The compound according to claim 1, wherein n is 0.

12. A method for palliatively treating diseases which are influenced by modulation of the GPR40 receptor, wherein the diseases are metabolic diseases, in a patient in need thereof, the method comprising administering to the patient an effective amount of the compound according to claim 1 or a pharmaceutically acceptable salt thereof.

13. The pharmaceutical composition according to claim 1, further comprising an additional therapeutic agent.

14. The pharmaceutical composition according to claim 13, wherein the additional therapeutic agent is selected from the group consisting of antidiabetic agents, agents for the treatment of overweight and/or obesity, and agents for the treatment of high blood pressure, heart failure, and/or atherosclerosis.

15. A compound compound of formula

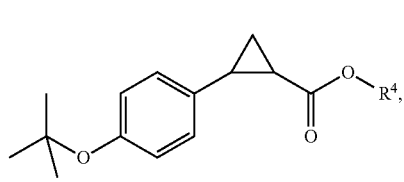

in racemic form, or the following enantiomers thereof

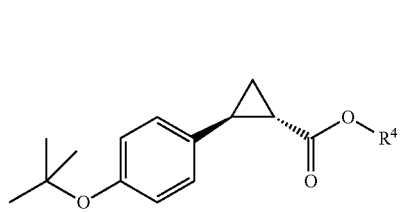

or

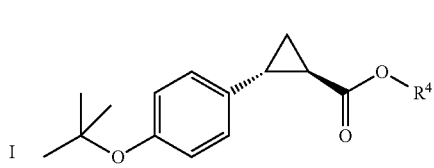

wherein $R^4$ is $C_{1-4}$-alkyl or phenyl-$CH_2$—.

16. A process for the preparation of an intermediate of formula XVa or XVb via intermediates XIVa or XIVb, comprising reacting 4-tert-butyloxystyrene with a diazo acetate ester following the reaction scheme

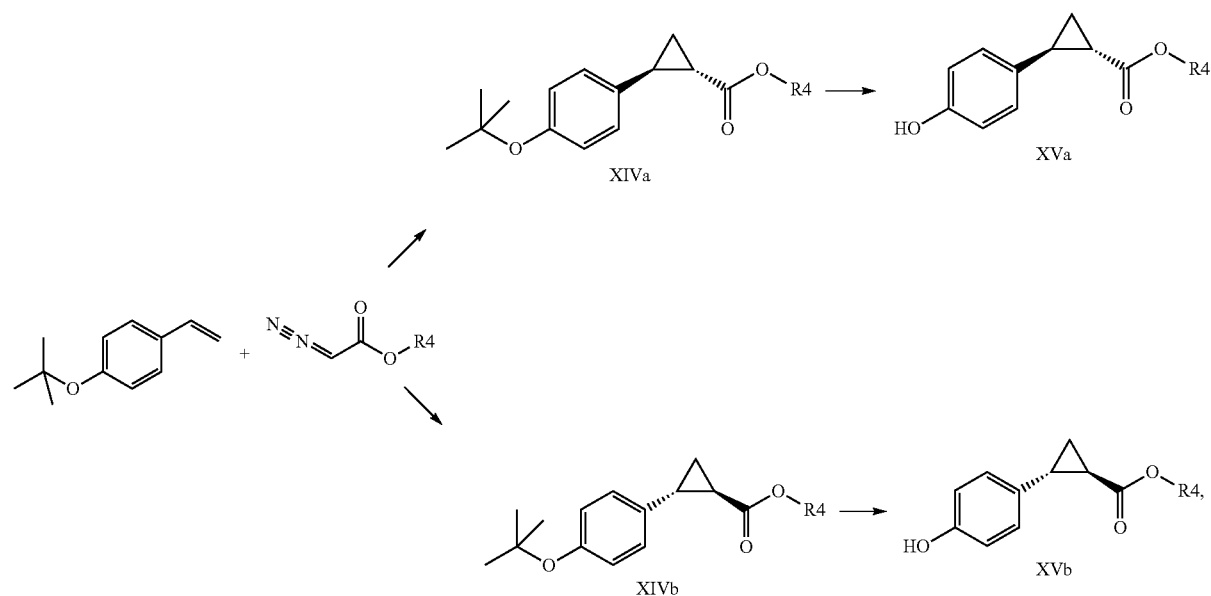

wherein $R^4$ is $C_{1-4}$-alkyl or phenyl-$CH_2$—, in the presence of a catalyst, and the resulting compounds of formula XVa or XVb are obtained in enantiomerically enriched form.

17. The process according to claim 16, wherein the catalyst used for preparation of an intermediate of formula XIVa is a complex of copper (I) trifluoromethanesulfonate benzene complex and (R,R)-2,2'-isopropylidenebis(4-tert-butyl-2-oxazoline) or the catalyst used for preparation of an intermediate of formula XIVb is a complex of copper (I) trifluoromethanesulfonate benzene complex and (S,S)-2,2'-isopropylidenebis(4-tert-butyl-2-oxazoline).

\* \* \* \* \*